(12) United States Patent
Khan

(10) Patent No.: US 10,940,097 B2
(45) Date of Patent: Mar. 9, 2021

(54) RESIN COMPOSITE AND RESTORATION CONTAINING BIOACTIVE GLASS FILLERS

(71) Applicant: Imam Abdulrahman Bin Faisal University, Dammam (SA)

(72) Inventor: Abdul Samad Khan, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 86 days.

(21) Appl. No.: 16/164,333

(22) Filed: Oct. 18, 2018

(65) Prior Publication Data

US 2020/0121562 A1   Apr. 23, 2020

(51) Int. Cl.

| | | |
|---|---|---|
| C03C 25/40 | (2006.01) |
| A61K 6/77 | (2020.01) |
| C03C 13/00 | (2006.01) |
| C03C 25/66 | (2006.01) |
| C03C 25/621 | (2018.01) |
| C03C 25/47 | (2018.01) |
| C03C 25/42 | (2006.01) |
| C03C 25/16 | (2006.01) |
| C03C 25/64 | (2006.01) |
| A61K 6/17 | (2020.01) |
| A61K 6/75 | (2020.01) |
| A61K 6/887 | (2020.01) |

(52) U.S. Cl.
CPC .................. *A61K 6/77* (2020.01); *A61K 6/17* (2020.01); *A61K 6/75* (2020.01); *A61K 6/887* (2020.01); *C03C 13/00* (2013.01); *C03C 25/16* (2013.01); *C03C 25/40* (2013.01); *C03C 25/42* (2013.01); *C03C 25/47* (2018.01); *C03C 25/621* (2018.01); *C03C 25/64* (2013.01); *C03C 25/66* (2013.01); *C03C 2213/02* (2013.01)

(58) Field of Classification Search
CPC ...................................................... A61L 27/46
See application file for complete search history.

(56) References Cited

U.S. PATENT DOCUMENTS

| | | | | |
|---|---|---|---|---|
| 6,270,562 | B1 * | 8/2001 | Jia | A61K 6/77 106/35 |
| 7,906,564 | B2 * | 3/2011 | Jia | A61K 6/30 523/116 |
| 2004/0166304 | A1 * | 8/2004 | Vallittu | A61L 27/16 428/313.3 |
| 2004/0241609 | A1 | 12/2004 | Jia et al. | |
| 2008/0065123 | A1 | 3/2008 | Yli-Urpo et al. | |
| 2008/0145820 | A1 * | 6/2008 | Karmaker | A61C 13/0003 433/220 |
| 2016/0243283 | A1 * | 8/2016 | Karhi | A61F 2/34 |
| 2016/0346435 | A1 | 12/2016 | D'Agostino et al. | |

FOREIGN PATENT DOCUMENTS

| | | |
|---|---|---|
| CN | 104129926 A | 11/2014 |
| CN | 103585672 B | 1/2015 |
| WO | 02/078646 A1 | 10/2002 |

OTHER PUBLICATIONS

Wu, et al. ; Study on the mechanical and biological property of PMMA bone cement modified with ultra-fine glass fibers and nano-hydroxyapatite ; Front. Mater. Sci. China 1 (3) ; pp. 247-251 ; 2007.*

Safronova, et al. ; Densification additives for hydroxyapatite ceramics ; ScienceDirect ; Journal of the European Ceramic Society 29 ; pp. 1925-1932 ; 2009 ; 8 pages.

Wu, et al. ; Study on the mechanical and biological property of PMMA bone cement modified with ultra-fine glass fibers and nano-hydroxyapatite ; Front. Mater. Sci. China 1 (3) ; pp. 247-251 ; 2007 ; 2 pages.

Domingo, et al ; Dental composites reinforced with hydroxyapatite: Mechanical behavior and absorption/elution characteristics ; Mar. 5, 2001 ; 9 pages.

Khalid, et al ; Microwave-assisted synthesis and in vitro osteogenic analysis of novel bioactive glass fibers for biomedical and dental applications ; BioMedical Materials ; 2018 ; 29 Pages.

* cited by examiner

*Primary Examiner* — Michael F Pepitone

(74) *Attorney, Agent, or Firm* — Oblon, McClelland, Maier & Neustadt, L.L.P.

(57) ABSTRACT

A glass based fibrous filler having bioactive particles such as hydroxyapatite deposited on a surface of glass fibers. Methods of preparing the fibrous filler are specified. A resin composite containing a polymerizable system reinforced with the fibrous filler, as well as a biomedical restoration based on the cured resin composite are also provided.

16 Claims, 31 Drawing Sheets
Specification includes a Sequence Listing.

RESIN COMPOSITE AND RESTORATION CONTAINING BIOACTIVE GLASS FILLERS

REFERENCE TO A SEQUENCE LISTING

In accordance with 37 CFR § 1.52(e)(5), the present specification makes reference to a Sequence Listing (submitted electronically as a .txt file named "512784US_version1_ST25.txt". The .txt file was generated on Jan. 11, 2021 and is 1,388 bytes in size. The entire contents of the Sequence Listing are herein incorporated by reference.

Aspects of this technology are described in an article "Microwave-assisted synthesis and in vitro osteogenic analysis of novel bioactive glass fibers for biomedical and dental applications" published in Biomedical Materials on Sep. 25, 2018, which is incorporated herein by reference in its entirety.

BACKGROUND OF THE INVENTION

Technical Field

The present disclosure relates to a fibrous filler involving bioactive apatite (e.g. hydroxyapatite) coated glass fibers, a resin composite reinforced with the fibrous filler, a method for making the fibrous fibers, and a biomedical restoration based on the cured resin composite.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Since their introduction about 50 years ago, resin based composites gained popularity as dental restorative materials. Compared to dental amalgam, resin based dental composites are safer and more aesthetically appealing [Streza M, Belean B, Hodisan I, Prejmerean C. Improving lock-in thermography detection of microgaps located at the tooth-filling interface using a phase versus amplitude image signal extraction approach. Measurement 2017;104:21-8]. Advantages of resin composites include minimal cavity preparation, mechano-chemical bonding to the tooth, and application in anterior as well as posterior restorations. A cross sectional study in 2005 reported that more than 95% of all anterior tooth direct restorations and about 50% of all posterior tooth direct restorations were placed using resin composites [Stein P S, Sullivan J, Haubenreich J E, Osborne P B. Composite resin in medicine and dentistry. Journal of long-term effects of medical implants 2005;15:641-54]. However, some remaining problems such as poor wear resistance, micro leakage due to polymerization shrinkage of the resin composite, which is responsible for secondary caries, are affecting long-term performance of resin composites [da Rosa Rodolpho P A, Cenci M S, Donassollo T A, Loguercio A D, Demarco F F. A clinical evaluation of posterior composite restorations: 17-year findings. Journal of dentistry 2006;34: 427-35; and Brunthaler A, Konig F, Lucas T, Sperr W, Schedle A. Longevity of direct resin composite restorations in posterior teeth. Clinical oral investigations 2003;7:63-70]. In addition, restoration failures of resin composites with inadequate mechanical properties occur under masticatory forces [Bayne S C, Heymann H O, Swift E J, Jr. Update on dental composite restorations. Journal of the American Dental Association (1939) 1994;125:687-701; and Wang X, Cai Q, Zhang X, Wei Y, Xu M, Yang X, et al. Improved performance of Bis-GMA/TEGDMA dental composites by net-like structures formed from $SiO_2$ nanofiber fillers. Materials science & engineering C, Materials for biological applications 2016;59:464-70]. Over the years, filler modifications such as optimization of filler concentration and/or sizes along with the development of hybrid fillers have been identified as effective approaches to increase the longevity of composites. Since the advent of nanotechnology, researchers have developed several nanomaterials that have more favorable properties than those of traditional fillers [Adabo G L, dos Santos Cruz C A, Fonseca R G, Vaz L G. The volumetric fraction of inorganic particles and the flexural strength of composites for posterior teeth. Journal of dentistry 2003;31:353-9; Habib E, Wang R, Wang Y, Zhu M, Zhu X X. Inorganic Fillers for Dental Resin Composites: Present and Future. ACS Biomaterials Science & Engineering 2016;2:1-11; Xia Y, Zhang F, Xie H, Gu N. Nanoparticle-reinforced resin-based dental composites. Journal of dentistry 2008;36:450-5; and Manhart J, Kunzelmann K H, Chen H Y, Hickel R. Mechanical properties and wear behavior of light-cured packable composite resins. Dental materials, 2000;16:33-40, each incorporated herein by reference in their entirety].

Fallis et al. introduced a short glass fiber which can be used in a dental restorative resin composite [Fallis D, Kusy R. Novel esthetic bonded retainers: a blend of art and science. Clinical orthodontics and research 1999;2:200-8, incorporated herein by reference in its entirety]. The purpose of fabricating this composite biomaterial is to develop a base filling dental material applicable in the areas bearing high stress such as large cavities within molar and premolar teeth. Advantages of short glass fiber based composites include enhanced flexural strength, flexural modulus, and higher fracture toughness than traditional biomaterials [Garoushi S, Tanner J, Vallittu P, Lassila L. Preliminary clinical evaluation of short fiber-reinforced composite resin in posterior teeth: 12-months report. The open dentistry journal 2012;6: 41, incorporated herein by reference in its entirety]. U.S. Pat. No. 2,477,268 to Saffir and U.S. Pat. No. 2,514,076 to Kelly disclosed uses of randomly dispersed short glass fibers in dental resin materials [U.S. Pat. Nos 2,477,268, and 2,514, 076, each incorporated herein by reference in their entirety]. U.S. Pat. Nos. 4,894,102 to Goldberg et al. disclosed the use of long, fully wetted fibers as structural components for dental restorations [U.S. Pat. No. 4,894,102, incorporated herein by reference in its entirety]. However, none of these patents disclosed a composite with satisfactory mechanical properties. U.S. Pat. Nos. 4,381,918 and 4,392,828 to Ehmnford disclosed a filler comprising porous inorganic particles which were completely or partially impregnated in a resin material [U.S. Pat. No. 4,381,918; and U.S. Pat. No. 4,392, 828, each incorporated herein by reference in their entirety]. The porous inorganic particles were formed by heating inorganic fibers under pressure to fuse the fibers at their points of contact, thereby forming a rigid three-dimensional network of inorganic fibers. U.S. Pat. No. 5,621,035 to Lyles et al. disclosed fused fibrous fillers comprising silica fibers fused with either alumina or aluminosilicate fibers in the presence of a fusion source such as boron nitride [U.S. Pat. No. 5,621,035, incorporated herein by reference in its entirety]. The fused network was then ground to particles having a size of about 180 microns, thereby forming fillers usable in dental composites. U.S. Pat No. 6,013,694 A disclosed a composition involving ground, densified, and brittle glass fibers together with other fillers and a polymeric matrix precursor [U.S. Pat. No. 6,013,694, incorporated herein by reference in its entirety]. The ground, densified, embrittled glass fibers were obtained by grinding glass fibers which have been densified and embrittled by heating glass fibers at a temperature substantially below the softening point of the glass fibers, without significant fusing or melting of the fibers.

Modern dentistry has been focusing on the incorporation of bioactive constituents like apatite to increase the bonding efficacy and marginal adaptation to prevent the occurrence of dental caries. Once incorporated in the resin matrix of composite restorations, bioactive fillers capable of sustained release of supersaturated calcium and phosphate ions may enhance the longevity of restorations and reduce the chance of secondary caries by sealing the tooth-material interface [Skrtic D, Antonucci J, Eanes E. Amorphous Calcium Phosphate-Based Bioactive Polymeric Composites for Mineralised Tissue Regeneration. J Res Nat Inst Stand Technol 2003;108:167-82; and Kessler S, Lee S. Use of bioactive glass in dental filling material, US patent application No. 2004/0065228, each incorporated herein by reference in their entirety]. Bioactive fillers can bond with the living tissue chemically by forming a calcium phosphate layer at the tooth-material interface, which makes the restoration durable and prevents it from bacterial ingression [Khan A, Ahmed Z, Edirisinghe M, Wong F, Rehman I. Preparation and characterization of a novel bioactive restorative composite based on covalently coupled polyurethane—nanohydroxyapatite fibres. Acta Biomaterialia 2008;4:1275-87, incorporated herein by reference in its entirety].

In view of the forgoing, one objective of the present disclosure is to provide a fibrous filler having bioactive calcium phosphate material disposed on glass fibers. Another objective of the present disclosure is to provide a resin composite and a biomedical restoration that contains the fibrous filler, polymerizable monomers, and polymerization initiators. The incorporation of fibrous fillers can provide mechanical strength to the composite structure. In the present disclosure, a bioactive fibrous filler involving nHA coated on a surface of glass fibers is prepared via in situ synthesis. Resin composites containing polymer matrix reinforced with the bioactive fibrous filler are also developed for dental restoratives and implant materials.

BRIEF SUMMARY OF THE INVENTION

According to a first aspect, the present disclosure relates to a fibrous filler comprising (i) glass fibers having a diameter of 5-100 μm and a length of 50-2,000 μm, (ii) bioactive particles comprising hydroxyapatite disposed on a surface of the glass fibers, and (iii) a silane coating that coats at least a portion of a surface of the glass fibers, bioactive particles, or both, wherein the glass fibers are present in an amount of 15-65 wt % relative to a total weight of the fibrous filler.

In one embodiment, the glass fibers are E-glass fibers.

In one embodiment, the bioactive particles have an average particle size of 5-500 nm.

In one embodiment, the bioactive particles further comprise fluorapatite, amorphous calcium phosphate, or both.

According to a second aspect, the present disclosure relates to a resin composite comprising a polymerizable monomer, a polymerization initiator system, and the fibrous filler of the first aspect.

In one embodiment, the fibrous filler is present in an amount ranging from 25 wt % to 75 wt % relative to a total weight of the resin composite.

In one embodiment, the polymerizable monomer is at least one selected from the group consisting of a methacrylate monomer, an acrylate monomer, an epoxy monomer, and a vinyl monomer.

In one embodiment, the polymerizable monomer is a methacrylate monomer.

In one embodiment, the methacrylate monomer is at least one selected from the group consisting of bisphenol A-glycidyl methacrylate (bis-GMA), urethane dimethacrylate (UDMA), and triethylene glycol dimethacrylate (TEGDMA).

In one embodiment, the methacrylate monomer is a mixture of bisphenol A-glycidyl methacrylate (bis-GMA), urethane dimethacrylate (UDMA), and triethylene glycol dimethacrylate (TEGDMA).

In one embodiment, a weight ratio of bisphenol A-glycidyl methacrylate (bis-GMA) to urethane dimethacrylate (UDMA) ranges from 2:1 to 1:2, and a weight ratio of bisphenol A-glycidyl methacrylate (bis-GMA) to triethylene glycol dimethacrylate (TEGDMA) ranges from 3:1 to 1:1.

In one embodiment, the polymerization initiator system comprises a free radical initiator.

In one embodiment, the polymerization initiator system consists of camphorquinone and ethyl 4-(dimethylamino) benzoate.

According to a third aspect, the present disclosure relates to a biomedical restoration comprising the resin composite of the second aspect in cured form.

In one embodiment, the biomedical restoration has a Vickers hardness number HV of 45-70.

In one embodiment, the biomedical restoration has a push-out bond strength to dentin of 15-60 MPa.

According to a fourth aspect, the present disclosure relates to a method of preparing the fibrous filler of the first aspect. The method involves (i) heating the glass fibers in an acidic solution to form acid activated glass fibers, (ii) washing and drying the acid activated glass fibers to form surface activated glass fibers, (iii) mixing the surface activated glass fibers with an aqueous solution comprising a Ca(II) salt and $NH_4OH$ to form a first mixture, (iv) mixing an aqueous solution of $(NH_4)_2HPO_4$ with the first mixture to form a second mixture, (v) microwave irradiating the second mixture to form a third mixture, (vi) aging the third mixture to produce a crude fibrous filler, and (vii) treating the crude fibrous filler with a silanization agent, thereby forming the fibrous filler.

In one embodiment, the Ca(II) salt is calcium(II) nitrate.

In one embodiment, the first mixture and the second mixture each have a pH of 9-11.

In one embodiment, microwave irradiating the second mixture is performed at 500-2000 W for 1-30 minutes.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
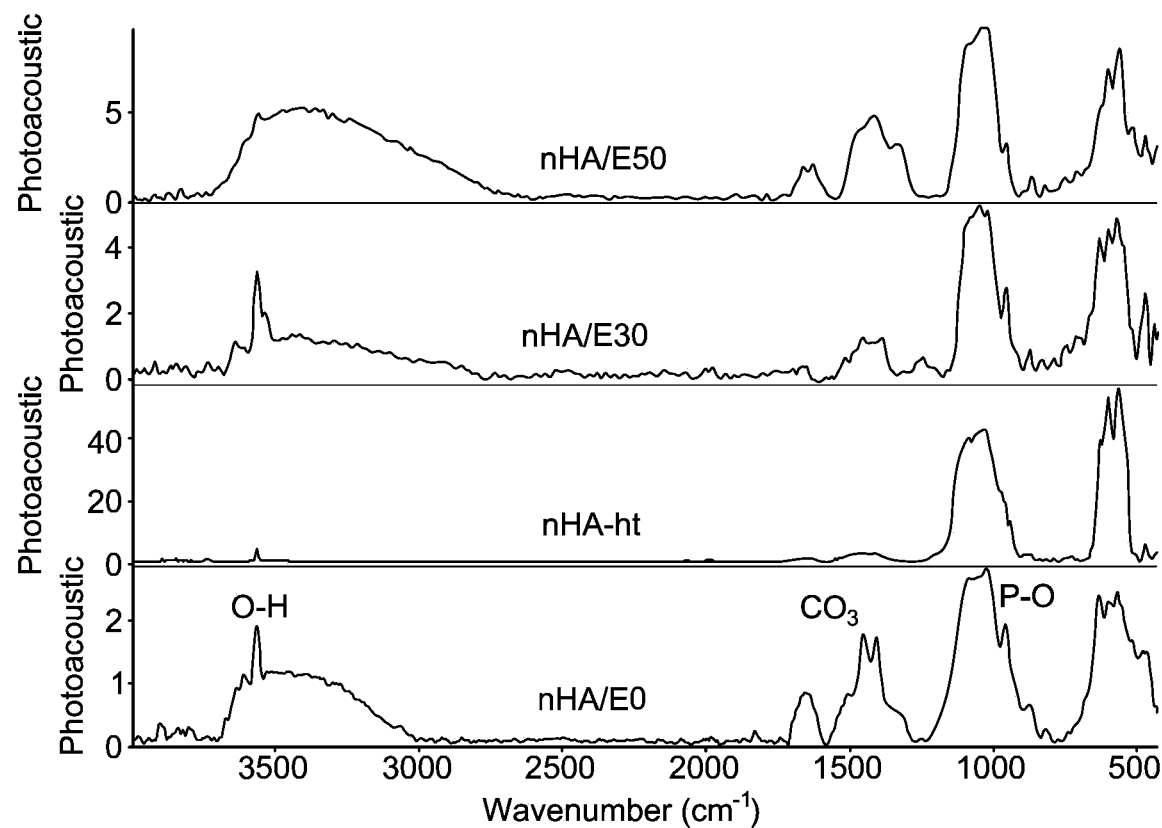
FIG. 1 is an overlay of Fourier transform Infrared (FTIR) spectra of nano hydroxyapatite (nHA/E0, or nHA), heat treated nano hydroxyapatite (nHA-ht), a fibrous material containing 30 wt % E-glass fibers and nano hydroxyapatite disposed on the E-glass fibers (nHA/E30), and a fibrous material containing 50 wt % E-glass fibers and nano hydroxyapatite disposed on the E-glass fibers (nHA/E50).
Figure 2A:
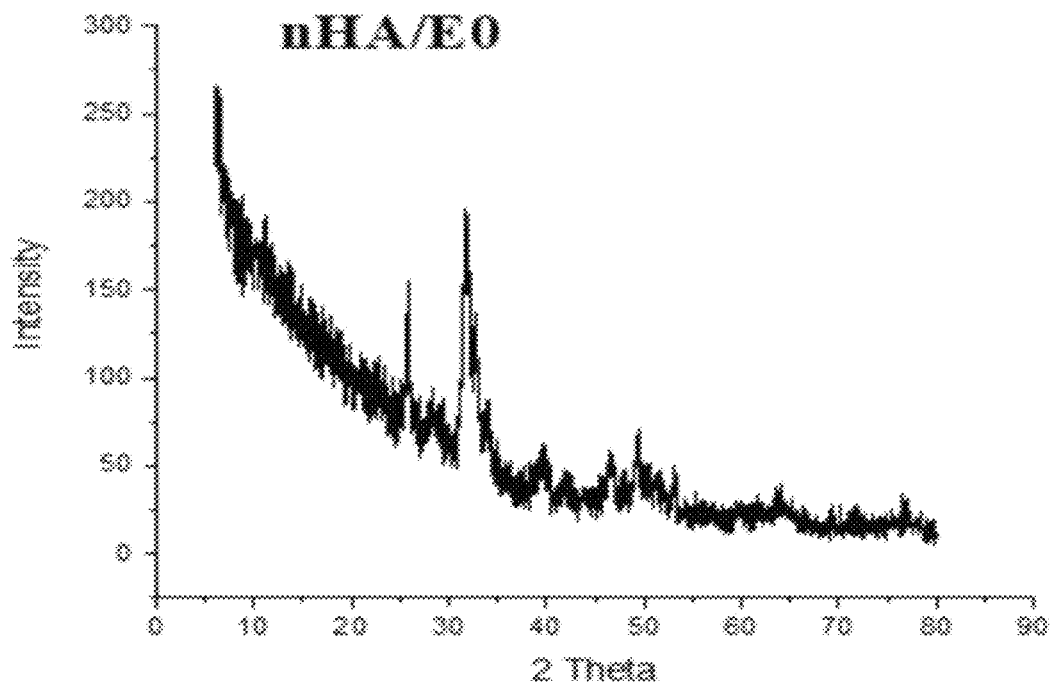
FIG. 2A shows the X-ray diffraction (XRD) pattern of nHA/E0 (or nHA).
Figure 2B:
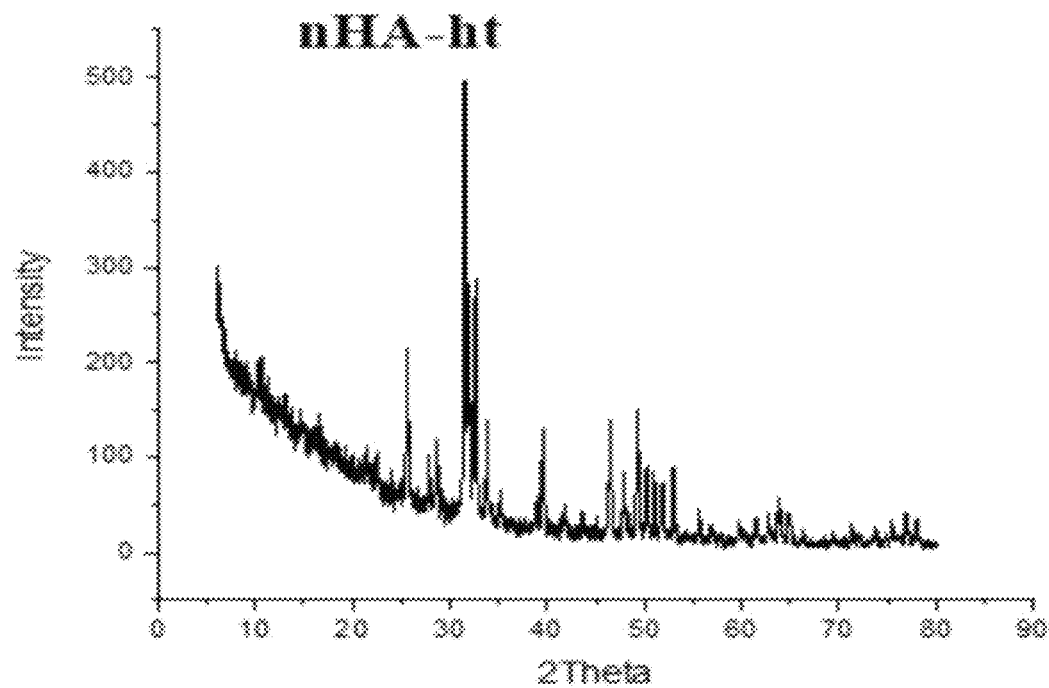
FIG. 2B shows the XRD pattern of nHA-ht.
Figure 2C:
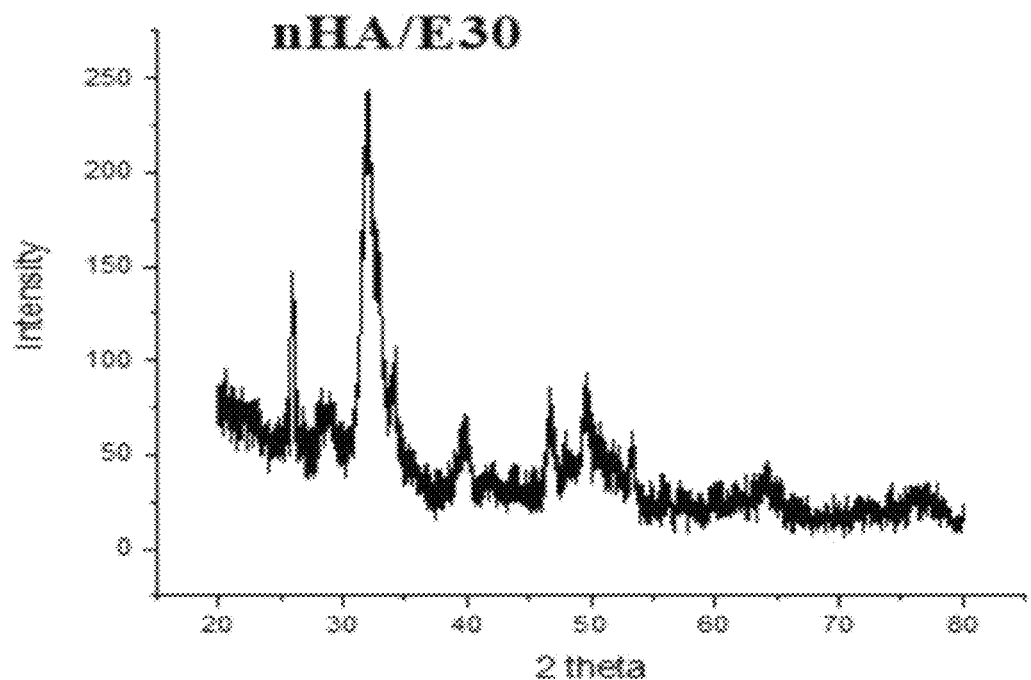
FIG. 2C shows the XRD pattern of nHA/E30.
Figure 2D:
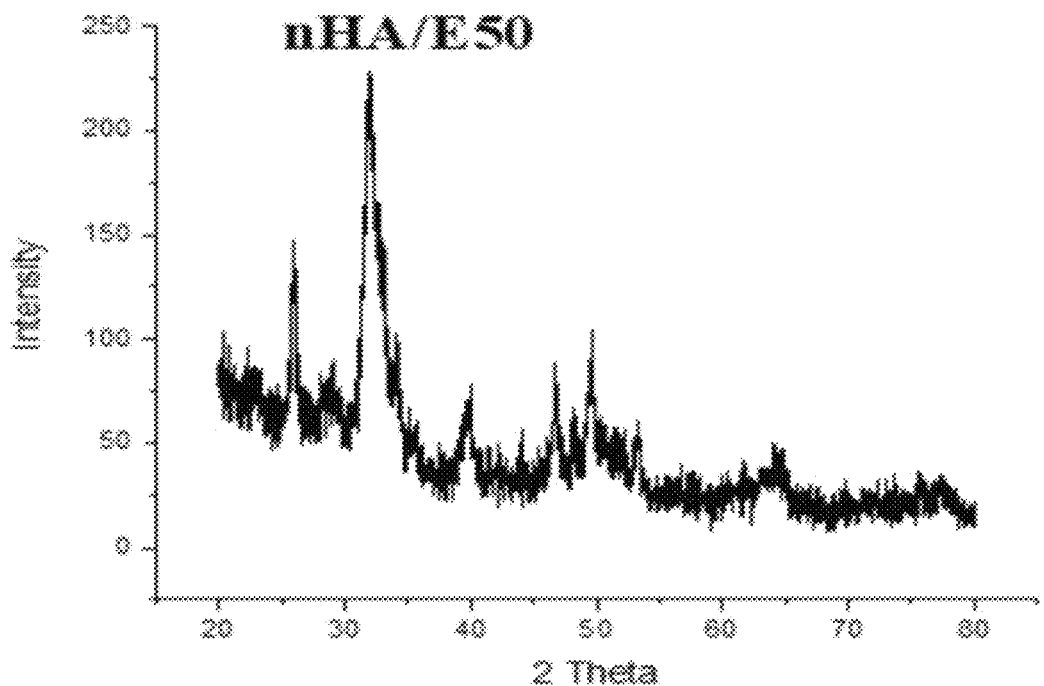
FIG. 2D shows the XRD pattern of nHA/E50.

Embodiments of the present disclosure will now be described more fully hereinafter with reference to the accompanying drawings, in which some, but not all embodiments of the disclosure are shown.

Unless otherwise specified, "a," "an," "at least one," and "one or more" are used interchangeably.

Within the description of this disclosure, where a numerical limit or range is stated, the endpoints are included unless stated otherwise. Also, all values and subranges within a numerical limit or range are specifically included as if explicitly written out.

As used herein, the words "substantially the same", "approximately", or "about" may be used when describing magnitude and/or position to indicate that the value and/or position described is within a reasonable expected range of values and/or positions. For example, a numeric value may have a value that is±1% of the stated value (or range of values),±2% of the stated value (or range of values),±5% of the stated value (or range of values),±10% of the stated value (or range of values),±15% of the stated value (or range of values), or±20% of the stated value (or range of values).

The present disclosure includes all hydration states of a given compound or formula, unless otherwise noted. For example, $Ca(NO_3)_2$ includes anhydrous $Ca(NO_3)_2$, $Ca(NO_3)_2 \cdot 4H_2O$, and any other hydrated forms or mixtures.

According to a first aspect, the present disclosure relates to a fibrous filler comprising (i) glass fibers, (ii) bioactive particles comprising hydroxyapatite disposed on a surface of the glass fibers, and (iii) a silane coating that coats at least a portion of a surface of the glass fibers, bioactive particles, or both.

Biomedical materials containing glass fibers have gained importance for clinical applications because of their physical and mechanical properties [Sonmez M, Georgescu M, Vahan M, Radulescu M, Ficai D, Voicu G, et al. Design and characterization of polypropylene matrix/glass fibers composite materials. Journal of Applied Polymer Science 2015; 132, incorporated herein by reference in its entirety], as well as their stability in the human body [Vallittu P K, Närhi T O, Hupa L. Fiber glass—bioactive glass composite for bone replacing and bone anchoring implants. Dental Materials 2015;31:371-81, incorporated herein by reference in its entirety]. Similar to other glass materials, glass fibers are amorphous, non-resorbable, and relatively durable. They often contain a non-heterogeneous three-dimensional mesh of haphazardly arranged $SiO_2$, $Al_2O_3$, CaO, MgO, $B_2O_3$, and $Na_2O$ [Khan A S, Azam M T, Khan M, Mian S A, Ur Rehman I. An update on glass fiber dental restorative composites: a systematic review. Materials science & engineering C, Materials for biological applications 2015;47:26-39; and Zhang M, Matinlinna J P. E-Glass Fiber Reinforced Composites in Dental Applications. Silicon 2012;4:73-8, each incorporated herein by reference in their entirety].

As used herein, glass fibers refer to a material containing fine fibers of glass. Exemplary glasses include glasses containing small amounts of metals (barium, strontium, aluminum, etc) such as barium borosilicate glass, aluminosilicate glass, boroaluminosilicate, strontium borosilicate glass, strontium-alumino-fluoro-silicate glass, and fluoroaluminosilicate glass. Exemplary glass fibers include, but are not limited to E-glass, A-glass, C-glass, D-glass, R-glass, S-glass, and E-glass derivatives such as E-CR-glass. E-glass is alumino-borosilicate glass with less than 1% wt/wt of alkali oxides. A-glass is alkali-lime glass with little or no boron oxide. C-glass is alkali-lime glass with high boron oxide content. D-glass is borosilicate glass named for its low Dielectric constant. R-glass is aluminosilicate glass without MgO or CaO. S-glass is aluminosilicate glass without CaO but with high MgO content. E-CR-glass is alumino-lime silicate with less than 1% w/w alkali oxides having electrical and chemical resistance. E-glass and S-glass fibers have been mainly used for clinical applications [Vakiparta M, Puska M and Vallittu P K 2006 Residual monomers and degree of conversion of partially bioresorbable fiber-reinforced composite, Acta Biomaterialia 2 29-37; and Moritz N, Strandberg N, Zhao D S, Manila R, Paracchini L, Vallittu P K and Aro H T 2014 Mechanical properties and in vivo performance of load-bearing fiber-reinforced composite intramedullary nails with improved torsional strength, Journal of The Mechanical Behavior of Biomedical Materials 40 127-39, each incorporated herein by reference in their entirety].

Glass fibers may be commercially available or made in-house in a variety of lengths and cross-sections. Cross-sections of the glass fibers of the present disclosure may be round, oval, elliptic, indented, star-shaped, triangular, and/or polygonal. As used herein, a diameter of a glass fiber is defined as a diameter of the cross-section of the glass fiber. For a circle, an oval, an ellipse, and a multilobe, "diameter" refers to the greatest possible distance measured from one point on the shape through the center of the shape to a point directly across from it. For polygonal shapes, the term "diameter", as used herein, and unless otherwise specified, refers to the greatest possible distance measured from a vertex of a polygon through the center of the face to the vertex on the opposite side.

In one or more embodiments, the glass fibers have an average diameter of 5-100 μm, preferably 10-50 μm, more preferably 15-30 μm, or about 20 μm. However, in some embodiments, the glass fibers may have an average diameter of less than 5 μm or greater than 100 μm. In one or more embodiments, the glass fibers have an average length of 50-2,000 μm, preferably 100-1,000 μm, preferably 120-800 μm, preferably 140-600 μm, preferably 160-400 μm, preferably 180-200 μm. However, in some embodiments, the glass fibers may have an average length of less than 50 μm or greater than 2,000 μm. The cross-section of the glass fibers may be constant over the length of glass fibers or may vary over the length. In a preferred embodiment, the cross-section of the glass fibers is uniform throughout the entire length of the glass fibers and is of a round shape. In another embodiment, the glass fibers are conical-shaped or elongated oval-shaped.

In one or more embodiments, the glass fibers are present in the fibrous filler in an amount of 10-70 wt % relative to a total weight of the fibrous filler, preferably 15-65 wt %, preferably 20-60 wt %, preferably 25-55 wt %, preferably 30-50 wt %, preferably 35-45 wt % relative to a total weight of the fibrous filler. However, in certain embodiments, the glass fibers are present in an amount of less than 10 wt % or greater than 70 wt % relative to a total weight of the fibrous filler.

Materials having E-glass fibers dispersed in a polymeric matrix have shown improved mechanical properties [Vallittu P, Lassila V. Reinforcement of acrylic resin denture base material with metal or fibre strengtheners. Journal of oral rehabilitation 1992;19:225-30, incorporated herein by reference in its entirety]. They were proposed to be used as bone anchoring implant materials in dental, orthopedic, and craniofacial surgeries recently [Ballo A M, Akca E A, Ozen T, Lassila L, Vallittu P K, Narhi T O. Bone tissue responses to glass fiber-reinforced composite implants- a histomorphometric study. Clin Oral Implants Res 2009;20:608-15; and Abdulmajeed A A, Lassila L V, Vallittu P K, Narhi T O. The effect of exposed glass fibers and particles of bioactive glass on the surface wettability of composite implants. International journal of biomaterials 2011;2011, each incorporated herein by reference in their entirety]. In a preferred embodiment, the glass fibers present in the fibrous filler disclosed herein are E-glass fibers.

The physical characteristics of glass fiber reinforced composites (GFRC) are similar to human teeth. Compared to other resin-based composites, failure of these GFRCs is less likely to occur [Khan A S, Azam M T, Khan M, Mian S A, Rehman I U. An update on glass fiber dental restorative composites: A systematic review. Materials Science and Engineering: C 2015;47:26-39, incorporated herein by reference in its entirety]. When combined with bioactive glass (BG), GFRCs may be potentially used as an implant [Tuusa S M, Peltola M J, Tirri T, Lassila L V, Vallittu P K. Frontal bone defect repair with experimental glass-fiber-reinforced composite with bioactive glass granule coating. Journal of biomedical materials research Part B, Applied biomaterials 2007;82:149-55, incorporated herein by reference in its entirety]. However, BG was often embedded in a resin matrix as loose particles and had no interaction with glass fibers. The adhesion of BG particles or fibers may affect the dissolution rate of bioactive ingredients in a composite. Additional coating of bioactive materials on fiber reinforced composites (FRC) might help control the initial ion release rate and facilitate osseointegration [Vallittu P K, Narhi T O, Hupa L. Fiber glass-bioactive glass composite for bone replacing and bone anchoring implants. Dental materials, 2015;31:371-81, incorporated herein by reference in its entirety].

As used herein, hydroxyapatite (HA, HAp, or hydroxylapatite) refers to a mineral form of calcium apatite with the formula $Ca_5(PO_4)_3(OH)$, but is usually written as $Ca_{10}(PO_4)_6(OH)_2$ to denote that the crystal unit comprises two entities. Hydroxyapatite is the hydroxyl endmember of the complex apatite group. In certain embodiments, the OW ion can be replaced by fluoride, chloride, and/or carbonate, producing fluorapatite or chlorapatite. It crystallizes in the hexagonal crystal system. The Ca:P ratio is often used in the discussion of calcium phosphate phases. Stoichiometric apatite $Ca_{10}(PO_4)_6(OH)_2$ has a Ca:P ratio of 10:6 normally expressed as 1.67. In a preferred embodiment, the hydroxyapatite of the present disclosure is a stoichiometric hydroxyapatite. Calcium deficient hydroxyapatite, $Ca_{10-x}(PO_4)_{6-x}(HPO_4)_x(OH)_{2-x}$ (where x is between 0 and 1), is a non-stoichiometric hydroxyapatite with a Ca:P ratio between 1.5 and 1.67. The non-stoichiometric phases have the hydroxyapatite structure with cation vacancies ($Ca^{2+}$) and anion ($OH^-$) vacancies. The sites occupied solely by phosphate anions in stoichiometric hydroxyapatite are occupied by phosphate or hydrogen phosphate $HPO_4^{2-}$ anions. In some embodiments, the hydroxyapatite of the present disclosure may be a non-stoichiometric hydroxyapatite with a Ca:P ratio between 1.25 and 1.67 or between 1.67 and 2.5.

As one of the most biocompatible and bioactive materials, hydroxyapatite (HA) has gained wide acceptance in medicine and dentistry [Gibson I R 2015 Hydroxyapatite (Hap) for Biomedical Applications: Woodhead Publishing, pp 269-87; and Enax J and Epple M 2018 Synthetic Hydroxyapatite as a Biomimetic Oral Care Agent Oral Health & Preventive Dentistry 16]. Chemical analysis revealed that calcium and phosphate are principal components of bone, enamel and dentin. Furthermore, the inorganic phase of bone and teeth are largely calcium hydroxyapatite [LeGeros R, LeGeros J, Kim Y, Kijkowska R, Zheng R, Bautista C, et al. Calcium phosphates in plasma-sprayed HA coatings. Ceram Trans 1994;48:173-89]. Because of its osteoconductive properties, HA may be a promising candidate for reconstructing calcified tissues of the human body including teeth and bones [Wei J, Wang J, Liu X, Ma J, Liu C, Fang J, et al. Preparation of fluoride substituted apatite cements as the building blocks for tooth enamel restoration. Applied Surface Science 2011; 257:7887-92].

Fluorapatite is a phosphate crystalline mineral with a formula $Ca_5(PO_4)_3F$ (calcium fluorophosphate). Along with hydroxyapatite, fluorapatite may be a component of tooth enamel minerals. Amorphous calcium phosphate (ACP) is a non-crystalline compound of variable compositions involving soluble phosphate and calcium salts which may readily dissolve in the saliva and transform into crystalline orthophosphates, such as hydroxyapatite and/or fluorapatite.

In one embodiment, the bioactive particles of the present disclosure comprise at least 90 wt %, preferably at least 95 wt %, preferably at least 99 wt %, more preferably 99.5 wt %, even more preferably 99.5 wt % hydroxyapatite relative to a total weight of the bioactive particles. In one embodiment, the bioactive particles may comprise less than 100 wt % hydroxyapatite relative to a total weight of the bioactive particles, and may further comprise fluorapatite, amorphous calcium phosphate, or both.

A particle is defined as a small object that behaves as a whole unit with respect to its transport and properties. The bioactive particles comprising hydroxyapatite, and optionally fluorapatite and/or amorphous calcium phosphate may be in the form of the same shape or different shapes, and of the same size or different sizes.

An average diameter (e.g., average particle size) of the particle, as used herein, refers to the average linear distance measured from one point on the particle through the center of the particle to a point directly across from it. In one embodiment, the bioactive particles have an average particle size of 5-500 nm, 10-200 nm, 20-100 nm, 30-75 nm, or 40-50 nm. The bioactive particles may be agglomerated or non-agglomerated (i.e., the bioactive particles are well separated from one another and do not form clusters). In one embodiment, the bioactive particles are agglomerated and the agglomerates have an average diameter in a range of 0.5-50 μm, 1-20 μm, or 2-10 μm.

Nanoparticles are particles between 1 and 100 nm in size. The exceptionally high surface area to volume ratio of nanoparticles may cause the nanoparticles to exhibit significantly different or even novel properties from those observed in individual atoms/molecules, fine particles and/or bulk materials. Nanoparticles may be classified according to their dimensions. Three-dimensional nanoparticles preferably have all dimensions of less than 100 nm, and generally encompass isodimensional nanoparticles. Examples of three dimensional nanoparticles include, but are not limited to nanoparticles, nanospheres, nanogranules and nanobeads. Two-dimensional nanoparticles have two dimensions of less than 100 nm, generally including diameter. Examples of two-dimensional nanoparticles include, but are not limited to, nanosheets, nanoplatelets, nanolaminas and nanoshells. One-dimensional nanoparticles have one dimension of less than 100 nm, generally including thickness. Examples of one-dimensional nanoparticles include, but are not limited to, nanotubes, nanofibers and nanowhiskers. In a preferred embodiment, the bioactive particles of the present disclosure are in the form of nanoparticles. The bioactive particles preferably are three-dimensional nanoparticles but may be one-dimensional, two-dimensional, three-dimensional or mixtures thereof. In an alternative embodiment, the bioactive particles used in the present disclosure may have one or more dimensions greater than 100 nm.

The bioactive particles may be spherical or substantially spherical (e.g., oval or oblong shape). In some embodiments, the bioactive particles are in the form of at least one shape such as a sphere, a rod, a cylinder, a rectangle, a triangle, a pentagon, a hexagon, a prism, a disk, a platelet, a flake, a cube, a cuboid, and an urchin (e.g., a globular particle possessing a spiky uneven surface).

In one embodiment, the bioactive particles are monodisperse, having a coefficient of variation or relative standard deviation, expressed as a percentage and defined as the ratio of the particle diameter standard deviation ($\sigma$) to the particle diameter mean ($\mu$), multiplied by 100%, of less than 25%, preferably less than 10%, preferably less than 8%, preferably less than 6%, preferably less than 5%. In a preferred embodiment, the bioactive particles are monodisperse having a particle size distribution ranging from 80% of the average particle size (e.g. diameter) to 120% of the average particle size, preferably 85-115%, preferably 90-110% of the average particle size. In another embodiment, the bioactive particles are not monodisperse.

In one or more embodiments, the bioactive particles are present in the fibrous filler in an amount of 5-60 wt % relative to a total weight of the fibrous filler, preferably 10-55 wt %, preferably 15-50 wt %, preferably 20-45 wt %, preferably 25-40 wt %, preferably 30-35 wt % relative to a total weight of the fibrous filler. However, in certain embodiments, the bioactive particles are present in an amount of less than 5 wt % or greater than 60 wt % relative to a total weight of the fibrous filler.

In one or more embodiments, the aforementioned bioactive particles are disposed on a surface of the glass fibers. The bioactive particles (e.g. hydroxyapatite) may interact with the surface hydroxyl and/or silanol groups on the surface of the glass fiber through chemical bonding (e.g. hydrogen bonding). The bioactive particles may also interact with the surface of the glass fibers via van der Waals forces and/or electrostatic forces. The bioactive particles preferably cover greater than 50%, greater than 60%, greater than 70%, greater than 80%, greater than 90%, greater than 95%, greater than 99% of the surface of the glass fiber. In one embodiment, the bioactive particles cover the glass fibers with an average thickness of 50-500 nm, preferably 60-450 nm, preferably 70-400 nm, preferably 80-350 nm, preferably 90-300 nm, preferably 100-250 nm, preferably 125-200 nm, preferably150-175 nm. In certain embodiments, the average thickness of the bioactive particles is less than 50 nm or greater than 500 nm.

In a preferred embodiment, the fibrous filler disclosed herein comprises a silane coating that coats a surface of the glass fibers, bioactive particles, or both. In a preferred embodiment, the silane coating coats only a portion of a total surface of the fibrous filler. Specifically, the silane coating may coat up to 50%, up to 60%, up to 75%, or up to 90% of a total surface area of the bioactive particle surface modified glass fibers. A silane coating may be formed by treating a glass substrate with a silanization agent. Typical silanization agents (herein also termed "silanes") suitable for the purpose of the invention include, but are not limited to, silanes bearing a methacrylic functional group such as methacryloxypropyl trimethoxy silane, silanes bearing an epoxy group such as glycidoxy propyl trimethoxy silane and beta-(3,4-epoxycyclohexyl)ethyl trimethoxysilane, silanes comprising an amino functional group such as gama-aminopropyl trimethoxy silane, gama-aminopropyl triethoxy silane and N-beta(aminoethyl)gama-aminopropyl trimethoxy silane), silanes comprising a mercapto group such as 3-mercaptopropyl trimethoxy silane, and a mixture thereof. An alternative silanization agent may be a mixture of one or more of the above silanes with an alkyl or aryl silane, where the alkyl or aryl group contains no reactive functional groups to undergo polymerization, such as phenyl trimethoxy silane and other phenyl silanes. Addition of an alkyl or aryl silane may improve adhesion and add hydrophobicity of the fibrous filler. In one embodiment, the concentration of the silane coating is in the range of 1-10 wt %, preferably 2-8 wt %, more preferably 3-7 wt % relative to a total weight of the fibrous filler. However, in certain embodiments, the amount of the silane coating is less than 1 wt % or greater than 10 wt % relative to a total weight of the fibrous filler.

In one embodiment, the fibrous filler disclosed herein in any of its embodiments exhibits no cytotoxic potential. The cytotoxicity of the filler may be determined by contacting an effective amount of the filler with cells (e.g. bone marrow-derived mesenchymal stem cells) and then performing cell viability assays. In one or more embodiments, the fibrous filler reduces the viability of the cells by less than 0.01%, 0.05%, 0.1%, 0.2%, 0.3%, 0.4%, 0.5%, 0.6%, 0.7%, 0.8%, 0.9%, 1%, 1.2%, 1.4%, 1.6%, 1.8%, or 2%, relative to the cells not treated with the fibrous filler. Examples of cell viability assays include, without limitation, ATP test, calcein AM assay, clonogenic assay, ethidium homodimer assay, Evans blue assay, fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, trypan blue assay and TUNEL assay. In a preferred embodiment, a MTT assay is used.

Osteoconductivity of a biomaterial is largely dependent on the biocompatibility and bioactivity of the biomaterial's surface [Smith D C, Pilliar R M and Chernecky R 1991 Dental implant materials. I. Some effects of preparative procedures on surface topography J of Biomedical Materials Research 25 1045-68]. Factors affecting properties of hydroxyapatite in cell adhesion and cell proliferation include its structure, phase purity, porosity, surface properties and sintering temperature [Khan A, Wong F, McKay I, Whiley R, Rehman I. Structural, mechanical, and biocompatibility analyses of a novel dental restorative nanocomposite. Journal of Applied Polymer Science 2013;127:439-47, incorporated herein by reference in its entirety]. Several methods including wet precipitation [Santos M H, Oliveira M d, Souza L P d F, Mansur H S, Vasconcelos W L. Synthesis control and characterization of hydroxyapatite prepared by wet precipitation process. Materials Research 2004;7:625-30, incorporated herein by reference in its entirety], chemical precipitation [Monmaturapoj N. Nano-size hydroxyapatite powders preparation by wet-chemical precipitation route. Journal of Metals, Materials and Minerals 2017;18, incorporated herein by reference in its entirety], sol-gel method [Khan A, Ahmed Z, Edirisinghe M, Wong F, Rehman I. Preparation and characterization of a novel bioactive restorative composite based on covalently coupled polyurethane—nanohydroxyapatite fibres. Acta Biomaterialia 2008; 4:1275-87, incorporated herein by reference in its entirety], and microwave irradiation [Nazir R, Khan A S, Ahmed A, Ur-Rehman A, Chaudhry A A, Rehman I U, et al. Synthesis and in-vitro cytotoxicity analysis of microwave irradiated nano-apatites. Ceramics International 2013;39:4339-47, incorporated herein by reference in its entirety] have been developed to prepare synthetic hydroxyapatite. Microwave-assisted synthetic approaches have been recently used for the preparation of composites, polymers, and ceramics [Das S, Mukhopadhyay A, Datta S, Basu D. Prospects of microwave processing: an overview. Bulletin of Materials Science 2009;32:1-13, incorporated herein by reference in its entirety]. Khan et al., synthesized high purity nano hydroxyapatite (nHA) and nHA/carbon nanotube in a short amount of time using a microwave-assisted wet precipitation technique [Khan A, Hussain A, Sidra L, Sarfraz Z, Khalid H, Khan M, et al. Fabrication and in vivo evaluation of hydroxyapatite/carbon nanotube electrospun fibers for biomedical/dental application. Materials Science and Engineering: C 2017, incorporated herein by reference in its entirety].

Another aspect of the present disclosure relates to a method of preparing the fibrous filler of the first aspect. The method involves (i) heating the glass fibers in an acidic solution to form acid activated glass fibers, (ii) washing and drying the acid activated glass fibers to form surface activated glass fibers, (iii) mixing the surface activated glass fibers with an aqueous solution comprising a Ca(II) salt and $NH_4OH$ to form a first mixture, (iv) mixing an aqueous solution of $(NH_4)_2HPO_4$ with the first mixture to form a second mixture, (v) microwave irradiating the second mixture to form a third mixture, (vi) aging the third mixture to produce a crude fibrous filler, and (vii) treating the crude fibrous filler with a silanization agent, thereby forming the fibrous filler.

The water used herein may be tap water, distilled water, bidistilled water, deionized water, deionized distilled water, reverse osmosis water, and/or some other water. In one embodiment, the water is bidistilled to eliminate trace metals. Preferably the water is bidistilled, deionized, deionized distilled, or reverse osmosis water and at 25° C. has a conductivity at less than 10 $\mu S \cdot cm^{-1}$, preferably less than 1 $\mu S \cdot cm^{-1}$, a resistivity greater than 0.1 $M\Omega \cdot cm$, preferably greater than 1 $M\Omega \cdot cm$, more preferably greater than 10 $M\Omega \cdot cm$, a total solid concentration less than 5 mg/kg, preferably less than 1 mg/kg, and a total organic carbon concentration less than 1000 μg/L, preferably less than 200 μg/L, more preferably less than 50 μg/L.

The method of preparing surface activated glass fibers involves heating the aforementioned glass fibers within a furnace or oven at a temperature of 80-300° C., 100-200° C., 120-180° C. or about 150° C., though in some embodiments, the glass fibers may be heated at a temperature of lower than 80° C. or higher than 300° C. In some embodiments, the glass fibers may be heated in air, oxygen-enriched air, an inert gas, or a vacuum. Preferably the glass fibers are placed in a drying furnace at room temperature or 20-50° C., and then the temperature is increased to a target temperature of 80-300° C., 100-200° C., 120-180° C. or about 150° C. at a rate of 5-15° C./min, preferably 8-12° C./min, or about 10° C./min. The glass fibers may be maintained at the target temperature for 0.5-12 hours, 1-6 hours, or 2-4 hours.

The method of preparing surface activated glass fibers also involves heating the glass fibers in an acidic solution at a temperature of 80-150° C., 90-125° C., or 100-110° C. for 1-6 hours, 2-5 hours, or 3-4 hours, and optionally with stirring to form acid activated glass fibers. The acidic solution may comprise an acid and water. Exemplary acids include, without limitation, hydrochloric acid, sulfuric acid, nitric acid, phosphoric acid, boric acid, hydrofluoric acid, hydrobromic acid, hydroiodic acid, perchloric acid, and the like. In one embodiment, the acidic solution is a solution comprising hydrochloric acid at a concentration of 0.5-5 M, preferably 1-4 M, preferably 2-3M. In a preferred embodiment, the acid activated glass fibers may be collected (filtered off), washed with water, and then dried at a temperature of 70-200° C., 90-150° C., 100-130° C., or about 110° C. for 0.5-6 hours, 1-4 hours, or 2-3 hours to form the surface activated glass fibers.

An amount of the surface activated glass fibers in the first mixture may be in the range of 1-70 wt %, 1-60 wt %, 10-50 wt %, or 20-40 wt % relative to a weight of the bioactive particles (e.g. hydroxyapatite generated in the current method). The surface activated glass fibers may be mixed with the aqueous solution of a Ca(II) salt and $NH_4OH$ by agitating such as stirring, shaking, sonicating, vibrating, vortexing, and the like that causes mixing. A concentration of Ca(II) salt in the first mixture may be in the range of 0.1-20 M, 0.2-10 M, 0.4-5 M, 0.6-4 M, 0.8-3 M, 0.9-2 M, or about 1 M. In a preferred embodiment, the Ca(II) salt is calcium(II) nitrate. Exemplary Ca(II) salts that may be used in addition to, or in lieu of calcium nitrate include, but are not limited to, calcium hydroxide, calcium acetate, calcium oxalate, calcium phosphate, calcium carbonate, calcium fluoride, and calcium chloride. In one embodiment, a sufficient amount of $NH_4OH$ is present in the first mixture to moderate the pH of the mixture. Preferably, the first mixture has a pH of 9-11, 9.5-10.5, or about 10.

A concentration of $(NH_4)_2HPO_4$ in the second mixture may be in the range of 0.05-15 M, 0.1-10 M, 0.2-5 M, 0.3-4 M, 0.4-3 M, or 0.5-2 M. Other phosphate ion sources that may be used in addition to, or in lieu of $(NH_4)_2HPO_4$ include, but are not limited to, monoammonium phosphate, triammonium phosphate, orthophosphoric acid, sodium or potassium orthophosphate, monobasic sodium or potassium phosphate, dibasic sodium or potassium phosphate, tribasic sodium or potassium phosphate, and magnesium phosphate. In one embodiment, an additional amount of $NH_4OH$ is introduced to the second mixture to maintain a desired pH of the mixture. Preferably, the second mixture has a pH of 9-11, 9.5-10.5, or about 10. In one embodiment, a ratio of Ca(II) salt to phosphate ion is maintained in the second mixture to create a Ca:P ratio of 1.67 to prepare a stoichiometric hydroxyapatite. For example, if $Ca(NO_3)_2$ is employed as the Ca(II) salt and $(NH_4)_2HPO_4$ as the phosphate ion, a molar ratio of $Ca(NO_3)_2$ to $(NH_4)_2HPO_4$ may be kept at 1.67 in the second mixture.

The method of preparing the crude fibrous filler involves microwave irradiating the second mixture. The second mixture may be exposed to a microwave irradiation of 200-2000 W, preferably 500-1750 W, more preferably 750-1500 W, or about 1000 W for 0.5-30 minutes to form the third mixture. In one embodiment, the exposure time may be 1-10 minutes, preferably 2-8 minutes, more preferably 3-5 minutes, though in another embodiment the exposure time may be 12-20 minutes, preferably 13-18 minutes, more preferably 14-16 minutes. In one embodiment, the microwave irradiation has a frequency in a range of 2200-2700 MHz, preferably 2300-2600 MHz, more preferably 2400-2500 MHz. In other embodiments, microwave frequencies lower than 2200 MHz or higher than 2700 MHz may be used. The microwave irradiation may come from a source such as a domestic, industrial, or commercial microwave oven, or from a different source of microwave irradiation, such as a transmitter directing microwave irradiation through a horn antenna, dish antenna, or waveguide. In one embodiment, the second mixture may be cooled by air cooling to prevent overheating by the microwave irradiation. In one embodiment, the microwave irradiating comprises alternating on and off cycles, wherein each on or off cycle is 10-20 seconds long, preferably 12-18 seconds long, more preferably 13-17 seconds long, or about 15 seconds long. Here, the "on cycle" means that the microwave irradiation is applied to the second mixture, while the "off cycle" means that no microwave irradiation is applied. Preferably the off cycle involves the microwave transmitter switching off so that it emits no irradiation, though in other embodiments, the microwave irradiation may be blocked, or reflected to a different direction while the transmitter continues to emit. In one embodiment, these alternating on and off cycles prevent the mixture from overheating, and may be coupled with other methods of cooling.

The third mixture may be collected (filtered off), washed with water, and then aged in an drying oven at a temperature of 50-200° C., 60-150° C., 70-120° C., or about 90° C. for 6-72 hours, 12-48 hours, 18-36 hours, or about 24 hours to form the crude fibrous filler. After aging, the crude fibrous filler may be placed in an oven at room temperature or 20-50° C., and then the temperature is increased to a target temperature of 200-500° C., 250-450° C., 300-400° C. or about 350° C. at a rate of 5-15° C./min, preferably 8-12° C./min, or about 10° C./min. The crude fibrous filler may be maintained at the target temperature for 0.5-4 hours, 0.75-2 hours, or about 1 hour.

Exemplary additional techniques of synthesizing hydroxyapatite that may be used in addition to, or in lieu of the current method include, but are not limited to, wet chemical precipitation, plasma spraying, hydrothermal synthesis, freeze drying, sol-gel, phase transformation, and mechano-chemical process.

Suitable means of silanization are generally known to those skilled in the art, and include treating the crude fibrous filler with an aforementioned silanization agent. In a preferred embodiment, the silanization agent is 3-(trimethoxysilyl)propyl methacrylate. In one embodiment, the treating comprises immersing the crude fibrous filler in a solution comprising 1-25 g of the silane coupling reagent per liter of the solution, preferably 2-20 g, preferably 4-18 g, preferably 6-15 g, preferably 8-12 g, or about 10 g of the silanization agent per liter of the solution at a pH of 3-6, 3.5-5, or about 4 for 0.5-48 hours, 1-36 hours, 2-30 hours, or 4-24 hours. The solution preferably comprises a solvent. Suitable solvents include, but are not limited to, ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, mixtures of xylenes, toluene, mesitylene, anisole, 1,2-dimethoxybenzene, α,α,α-trifluoromethylbenzene, fluorobenzene), chlorinated solvents (e.g. chlorobenzene, dichloromethane, 1,2-dichloroethane, 1,1-dichloroethane, chloroform), amide solvents (e.g. dimethylformamide, dimethylacetamide, N-methyl-2-pyrrolidone), ketones (e.g. acetone, butanone), hexane, dimethyl sulfoxide, acetonitrile, propionitrile, butyronitrile, benzonitrile, water and mixtures thereof. In a preferred embodiment, a mixture of ethanol and water at a volume ratio of 10:1 to 1:1, 9:1 to 4:1 or 8:1 to 6:1 is used as the solvent. The treating may further involve stirring and/or ultrasonication. After the treating, the obtained fibrous filler may be washed with ethanol, and dried at a temperature of 25-90° C., 50-80° C., or 60-70° C. for 1-7 days, 2-6 days, or 3-5 days.

As used herein, a "composite" refers to a combination of two or more distinct constituent materials into one. The individual components, on an atomic level, remain separate and distinct within the finished structure. The materials may have different physical or chemical properties, that when combined, produce a material with characteristics different from the individual components. A "resin composite" generally refers to a polymer-based composite containing a mixture of a polymerizable resin and a filler, and is used in modern dentistry as a restorative material or an adhesive. Because of their aesthetic appeal and mechanical strength, resin composites are often considered superior to traditional silver-mercury amalgam restoratives.

Another aspect of the present disclosure relates to a resin composite comprising a polymerizable monomer, a polymerization initiator system, and the fibrous filler of the present disclosure in any of its embodiments.

In one embodiment, the polymerizable monomer is at least one selected from the group consisting of a methacrylate monomer, an acrylate monomer, an epoxy monomer, and a vinyl monomer.

As used herein, monomers are molecules which can undergo polymerization, thereby contributing constitutional repeating units to the structures of a macromolecule, a polymer, or a resin. Compounds having one or more polymerizable groups and alkoxylated groups (ethylene oxide, polyethylene oxide, etc.) are to be viewed as an extension of a monomer unit and are still considered monomers in the present disclosure unless specified otherwise. The process by which monomers combine end to end to form a polymer is referred to herein as "polymerization". As used herein a "copolymer" refers to a polymer derived from more than one species of monomer and are obtained by "copolymerization" of more than one species of monomer. Copolymers obtained by copolymerization of two monomer and/or oligomer species may be termed bipolymers, those obtained from three monomers may be termed terpolymers and those obtained from four monomers may be termed quarterpolymers, etc. As used herein, "crosslinking", "cross-linking", "crosslinked", "cross-linked", a "crosslink", or a "cross-link" refers to polymers and resins containing branches that connect polymer chains via bonds that link one polymer chain to another. The crosslink may be an atom, a group of atoms, or a number of branch points connected by bonds, groups of atoms, or polymer chains. In a preferred embodiment, the polymerizable monomers in the present disclosure form crosslinking resins.

Polymerizable monomers used herein may include one or more mono-functional and/or multi-functional monomers. A mono-functional monomer refers to a monomer having one polymerizable group such as acrylate, methacrylate, epoxy, and vinyl present per molecule, while a multi-functional monomer refers to a monomer having two or more polymerizable groups present per molecule. Specifically, mono-functional methacrylate monomers useful in the present invention include, but are not limited to, methacrylic acid, methyl methacrylate (MMA), 2-hydroxyethyl methacrylate (HEMA), isopropyl methacrylate, n-propyl methacrylate, isopropyl methacrylate, n-butyl methacrylate, isobutyl methacrylate, hydroxyethyl methacrylate, hydroxypropyl methacrylate, hydroxybutyl methacrylate, propylene glycol monomethacrylate, isobornyl methacrylate, methoxyethoxyethyl methacrylate, ethoxyethoxyethyl methacrylate, tetrahydrofurfuryl methacrylate, acetoxyethyl methacrylate, phenoxyethylmethacrylate, methacryloyloxyethyl phthalate (MEP), and mixtures thereof. Useful multi-functional methacrylate monomers include, but are not limited to, bisphenol A-glycidyl methacrylate (bis-GMA), urethane dimethacrylate (UDMA), triethylene glycol dimethacrylate (TEGDMA), ethoxylated bisphenol A dimethacrylate (bis-EMA), ethyleneglycol dimethacrylate, diethyleneglycol dimethacrylate, trimethyleneglycol dimethacrylate, glycerol dimethacrylate, trimethyolpropane trimethacrylate, tetraethyleneglycol dimethacrylate, 1,3-propanediol dimethacrylate, 1,4-butanediol dimethacrylate, 1,6-hexanediol dimethacrylate, 1,12-dodecanediol dimethacrylate, polyethyleneglycol dimethacrylate, bismethacryloyloxymethyltricyclo-[5.2.1.]decane (TCDMA), trimethylolpropane trimethacrylate, 1,2,4-butanetriol trimethacrylate, pentaerythritol tetramethacrylate, diurethane dimethacrylate (DUDMA), pyromellitic acid glycerol dimethacrylate (PMGDM), and mixtures thereof.

Non-limiting examples of acrylate monomers include acrylic acid, methyl acrylate, ethyl acrylate, propyl acrylate, butyl acrylate, isobutyl acrylate, tert-butyl acrylate, pentyl acrylate, neopentyl acrylate, hexyl acrylate, cyclohexyl acrylate, heptyl acrylate, cyclohexylmethyl acrylate, octyl acrylate, 2-ethylhexyl acrylate, isooctyl acrylate, decyl acrylate, dodecyl acrylate, tetradecyl acrylate, hexadecyl acrylate, octadecyl acrylate, behenyl acrylate, ethyleneglycol diacrylate, neopentylglycol diacrylate, 1,6-hexanediol ethoxylate diacrylate, 1,3-butanediol diacrylate, 1,6-hexanediol diacrylate, 1,4-butanediol diacrylate, di(ethylene glycol) diacrylate, and mixtures thereof.

Epoxy monomers are compounds containing one or more glycidyl ether group, which include, but are not limited to, 1,2-epoxybutane, 1,2-epoxypentane, 1,2-epoxyhexane, glycidyl isopropyl ether, glycidyl 2,2,3,3-tetrafluoropropyl ether, butyl glycidyl ether, tert-butyl glycidyl ether, furfuryl glycidyl ether, 1,2-epoxyoctane, glycidyl 4-methoxyphenyl ether, 2-ethylhexyl glycidyl ether, (2,3-epoxypropyl)benzene, 1,2-epoxy-3-phenoxypropane, 1,2-epoxydodecane, neopentyl glycol diglycidyl ether, 1,4-cyclohexanedimethanol diglycidyl ether, 1,2,7,8-diepoxyoctane, 1,4-butanediol diglycidyl ether, resorcinol diglycidyl ether, N,N-diglycidyl-4-glycidyloxyaniline, and mixtures thereof.

Exemplary vinyl monomers include, but are not limited to, vinyl acetate, vinyl trifluoroacetate, vinyl propionate, vinyl valerate, vinyl neononanoate, vinyl decanoate, vinyl neodecanoate, vinyl stearate, vinyl benzoate, vinyl cinnamate, vinyl 4-tert-butylbenzoate, styrene, vinylbenzyl chloride, 4-vinylbenzoic acid, 2-(trifluoromethyl)styrene, 3-(trifluoromethyl)styrene, 4-(trifluoromethyl)styrene, 4-vinylanisole, 3-methylstyrene, 4-methylstyrene, 2-fluorostyrene, 3-fluorostyrene, 4-fluorostyrene, 2,6-difluorostyrene, 2,3,4,5,6-pentafluorostyrene, 4-tert-butylstyrene, 2,4,6-trimethylstyrene, 3,4-dimethoxystyrene, 4-acetoxystyrene, divinylbenzene, 1,4-bis(4-vinylphenoxy)butane, 1,3,5-triallyl-1,3,5-triazine-2,4,6(1H,3H,5H)-trione, and mixtures thereof.

In one embodiment, the polymerizable monomer in the present disclosure is one or more methacrylate monomers. In a preferred embodiment, the polymerizable monomer is one or more di-functional methacrylate monomer selected from the group consisting of bisphenol A-glycidyl methacrylate (bis-GMA), urethane dimethacrylate (UDMA), and triethylene glycol dimethacrylate (TEGDMA). In one embodiment, the polymerizable monomer is a combination of bis-GMA and TEGDMA at about 5:1 to about 1:5 mass ratio, about 4:1 to about 1:4 mass ratio, about 3:1 to about 1:3 mass ratio, about 2:1 to about 1:2 mass ratio, about 3:2 to about 2:3 mass ratio, or about 1:1 mass ratio. In another embodiment, the polymerizable monomer is a combination of UDMA and TEGDMA at about 5:1 to about 1:5 mass ratio, about 4:1 to about 1:4 mass ratio, about 3:1 to about 1:3 mass ratio, about 2:1 to about 1:2 mass ratio, about 3:2 to about 2:3 mass ratio, or about 1:1 mass ratio. In a preferred embodiment, the polymerizable monomer is a mixture of bis-GMA, UDMA, and TEGDMA. In one embodiment, a weight ratio of bis-GMA to UDMA ranges from 3:1 to 1:3, 2:1 to 1:2, 3:2 to 2:3, or about 1.2:1, and a weight ratio of bis-GMA to TEGDMA ranges from 4:1 to 1:2, 3:1 to 2:3, 2:1 to 1:1, or about 1.6:1.

In one or more embodiments, the polymerizable monomer described herein in any of its embodiments is present in the resin composite in an amount of about 20 wt % to about 70 wt %, about 25 wt % to about 65 wt %, about 30 wt % to about 60 wt %, about 35 wt % to about 55 wt %, or about 40 wt % to about 50 wt % relative to a total weight of the resin composite.

Fillers, when blended with the aforementioned polymerizable monomer, provide dental composites with greater mechanical strength and preferably with improved translucency. In one embodiment, the fibrous filler of the present disclosure in any of its embodiments is present in an amount of 25-75 wt %, 30-70 wt %, 35-65 wt %, 40-60 wt %, or 45-55 wt % relative to a total weight of the resin composite. In at least one embodiment, the filler used in the resin composite disclosed herein is the aforementioned crude fibrous filler which is not silanized. Other useful fillers that may present in the resin composite in addition to the presently disclosed fibrous filler include, without limitation, silica, ceramic fillers such as zirconia filler, zirconia-silica filler, quartz filler, and porcelain filler, as well as polymer-based fillers including polymeric material that is pre-polymerized, e.g. poly(methyl methacrylate), poly(ethyl methacrylate), poly(acrylic acid), poly(methacrylic acid), poly(vinyl acetate), polyethylene, and polytetrafluoroethylene, and then ground into filler particles, and polymer fibers.

Fillers that are commonly incorporated in a dental composite can be categorized into three major classes based on their average particle size, including macrofillers with an average particle size of 1-100 μm, microfillers with an average particle size of 0.01-0.1 μm, and nanofillers with an average particle size of 0.005-0.1 μm. The particle size of a filler may be dependent on the identity of the filler. For example, the fibrous filler disclosed herein may be present in the resin composite as a macrofiller, while zirconia particles having an average particle diameter of about 10 to about 100 nm may serve as a nanofiller. In some embodiments, fillers present in the dental composite of the current disclosure is a mixture of fillers with different average particle sizes, e.g. a mixture of macrofiller and nanofillers at an approximate weight ratio of 1:1 to 10:1, 2:1 to 8:1, or 4:1 to 6:1.

In one or more embodiment, the polymerization initiator system present in the currently disclosed dental composite is a free radical initiator. In some embodiments, a free radical initiator is included in the polymerizable monomer liquid at a concentration in a range of about 0.01% to about 5.0%, about 0.1% to about 4.0%, about 0.5% to about 3.0%, or about 1.0% to about 2.0% by weight relative to the total weight of the polymerizable monomer. Exemplary free radical initiators include, but are not limited to, camphorquinone, benzil, benzophenone, acyl phosphine oxides, e.g. phenylbis(2,4,6-trimethylbenzoyl)phosphine oxide (Irgacure 819, BASF) and diphenyl(2,4,6-trimethylbenzoyl) phosphine oxide, azo compounds, e.g. azobisisobutyronitrile (AIBN), 1,1'-azobis(cyclohexanecarbonitrile) (ABCN), and 4,4'-azobis(4-cyanovaleric acid), and organic peroxides, e.g. benzoyl peroxide, lauroyl peroxide, methyl ethyl ketone peroxide (MEKP), tert-butyl hydroperoxide, and tert-butyl peroxybenzoate.

In some embodiments, the polymerization initiator system further comprises a polymerization accelerator (co-initiator) that works in conjunction with the polymerization initiator to promote or improve the speed of polymerization reaction. The polymerization accelerator may be added to the polymerizable monomer liquid at a concentration in a range of about 0.1% to about 5.0% by weight relative to the total weight of the polymerizable monomer. Exemplary polymerization accelerators include, but are not limited to, N,N-dimethyl-p-toluidine, N,N-bis(2-hydroxyethyl)-p-toluidine, ethyl 4-(dimethylamino)benzoate, dimethylaminoethyl methacrylate, N-(2-cyanoethyl)-N-methyl aniline, 4-(N,N-dimethylamino)phenethyl alcohol, and 4-(N,N-dimethylamino)phenylacetic acid.

In a preferred embodiment, the polymerization initiator system consists of camphorquinone and ethyl 4-(dimethylamino)benzoate. In one embodiment, a combination of free radical initiator camphorquinone and co-initiator ethyl 4-(dimethylamino)benzoate at a weight ratio of about 1:4 to about 4:1, about 1:3 to about 3:1, about 1:2 to about 2:1, or about 1:1 is employed as the polymerization initiator system in the presently disclosed dental composite.

The resin composite of the current disclosure may further include a fluoride source selected from sodium fluoride, potassium fluoride, aluminum fluoride, zinc fluoride, stannous fluoride, ammonium fluoride, sodium monofluorophosphate and the like. The fluoride source may present in an amount of 0.01-2 wt %, 0.05-1 wt %, 0.1-0.5 wt %, or 0.2-0.4 wt % relative to the total weight of the resin composite.

Methods of preparing resin composites are generally known to those skilled in the art. For example, the resin composite disclosed herein may be prepared by (i) mixing polymerizable monomers (e.g. bis-GMA, TEGDMA, and UDMA) at aforementioned weight ratio to form a monomer liquid, (ii) adding photoinitiators (e.g. CQ) and polymerization accelerators/co-initiators (e.g. ethyl 4-(dimethylamino)benzoate) to the monomer liquid to form a polymerizable resin at aforementioned weight ratio and amount, (iii) adding fillers (e.g. the fibrous filler) to the polymerizable resin at the aforementioned weight ratio to form a composite mixture, (v) mixing the composite mixture by agitating to form the resin composite.

Methods of agitating a composite mixture include, without limitation, using an agitator, a vortexer, a rotary shaker, a magnetic stirrer, a centrifugal mixer, a dual asymmetric centrifugal mixer, or an overhead stirrer. In one embodiment, the composite mixture is agitated by sonication in an ultrasonic bath or with an ultrasonic probe. In another embodiment, the mixture is agitated using a magnetic stirrer with a rotational speed of at least 250 rpm, preferably at least 500 rpm, more preferably at least 750 rpm. In an alternative embodiment, the composite mixture is mixed with a spatula. In a preferred embodiment, the mixture is mixed using a dual asymmetric centrifugal mixer, e.g. SpeedMixer (Flack-Tek Inc.) at a speed of at least 800 rpm, preferably at least 1000 rpm, more preferably at least 1500 rpm.

A further aspect of the present disclosure relates to a biomedical restoration, comprising the resin composite of the present disclosure in cured form. Curing conditions and procedures for a resin composite are generally known to those skilled in the art. In some embodiments, wherein the polymerization initiator can be activated by an external light source, the currently disclosed resin composite may be cured by applying light at a proper wavelength and with sufficient intensity to the resin composite to initiate and propagate polymerization. In one or more embodiments, light is applied to the resin composite during curing for a period of time of at least 10 seconds, at least 20 seconds, at least 30 seconds, at least 40 seconds, at least 1 minute, at least 2 minutes, or at least 5 minutes. Depending on the identity of the photo-initiator, a light source at a wavelength of 300-800 nm, 320-700 nm, 340-600 nm, 360-550 nm, 380-500 nm, or about 470 nm may be applied. Depending on the composition of the resin composite and/or distance between the light and the resin composite sample, the curing may be performed at a light intensity of about 200-2000 mW/cm$^2$, about 400-1500 mW/cm$^2$, about 600-1200 mW/cm$^2$, or about 800-1000 mW/cm$^2$. Applicable light sources for the curing described herein may be commercially available from a variety of vendors, including, but not limited to, Woodpecker iLED curing light, Elipar™ S10 LED Curing Light (3M ESPE), XL3000 (3M ESPE), PROLITE (Dentsply Sirona), SPECTRUM (Dentsply Sirona), VIVALUX II (Ivoclar-Vivadent), and OPTILUX 500 (Demetron-Kerr).

A degree of conversion in a resin composite may be determined after curing. The degree of conversion (% DC) can be calculated by comparing the ratio of the aliphatic carbon-carbon double bond (C=C) relative to an internal standard, e.g. an aromatic or alkyl component for the cured and uncured resin composites. Useful analytical tools for determining % DC include Fourier-transform infrared (FT-IR) spectroscopy (see examples 4(iii) and 5(iii)), near-infrared (NIR) spectroscopy, Raman spectroscopy, and nuclear magnetic resonance (NMR) spectroscopy. In a preferred embodiment, the biomedical restoration formed by a cured resin composite of the present disclosure in any of its embodiments has a DC% in the range of 50%-75%, 55%-70%, or 60%-65%.

Hardness is a measure of how resistant solid matter is to various kinds of permanent shape change when a compressive force is applied. Indentation hardness tests are used in mechanical engineering to determine the hardness of a material to deformation. Several indentation hardness testing methods including Rockwell, Brinell, and Vickers methods exist, wherein the examined material is indented until an impression is formed. In one or embodiments, a Vickers hardness test is performed on the currently disclosed biomedical restoration according to ASTM E384-11e1 standard. In one or more embodiments, the biomedical restoration containing a cured resin composite of the present disclosure in any of its embodiments has a Vickers hardness number HV of about 45 to about 90, about 50 to about 85, about 55 to about 80, about 60 to about 75, or about 65 to about 70. Increasing the amount of the fibrous filler present in a resin composite may increase the Vickers hardness number HV of the corresponding restoration (see Table 6).

In one embodiment, the biomedical restoration containing a cured resin composite of the present disclosure may have a Vickers hardness number HV that is 30-50% greater, preferably 35-45% greater, more preferably 38-43% greater than that of a restoration formed with a substantially identical resin composite not reinforced with the fibrous filler. Here, the substantially identical resin composite not reinforced with the fibrous filler may refer to a resin containing bis-GMA, UDMA, and TEGDMA each present in relative weight percentages substantially the same to those in the currently disclosed resin composite. In another embodiment, the biomedical restoration containing a cured resin composite of the present disclosure may have a Vickers hardness number HV substantially the same to that of a restoration formed with a commercial composite (e.g. Filtek Z350, 3M ESPE). For example, a restoration formed with a cured resin composite containing about 60 wt % of the fibrous filler has a Vickers hardness number HV that is at least 5% greater than that of a restoration formed with the commercial composite Filtek Z350 (see Table 6).

The life span of a restorative material is dictated by its bonding efficacy to the tooth structure [Bouillaguet S, Gysi P, Wataha J, Ciucchi B, Cattani M, Godin C, et al. Bond strength of composite to dentin using conventional, one-step, and self-etching adhesive systems. Journal of Dentistry 2001;29:55-61]. The measurement of debonding force and bond strength are important to characterize the bonding capability of adhesives and restorative materials to the tooth structure. An effective adhesive bonding to dentin as well as enamel is essential for the attachment and retention of a dental restoration. A push-out bond strength is defined herein as a tension required to break the adhesive bond between the dentin and a restoration placed on the dentin. Preferably, the resin composite may release ions (e.g. calcium and phosphate ions) after the placement. The amount of the ions released may increase over time. However, a strength will reach a maximum value within a certain time, for example, within 180 days. In one embodiment, the restoration placed may release ions, though in certain embodiments, the restoration may be considered to release ions in less than 1 day or after 180 days after its placement. In one embodiment, the push-out bond strength test is conducted according to ISO/TS 11405:2015 standard. In at least one embodiment, the push-out bond strength of the restoration is determined after curing for 1-180 days, 5-90 days, or 10-30 days.

Figure 17A:
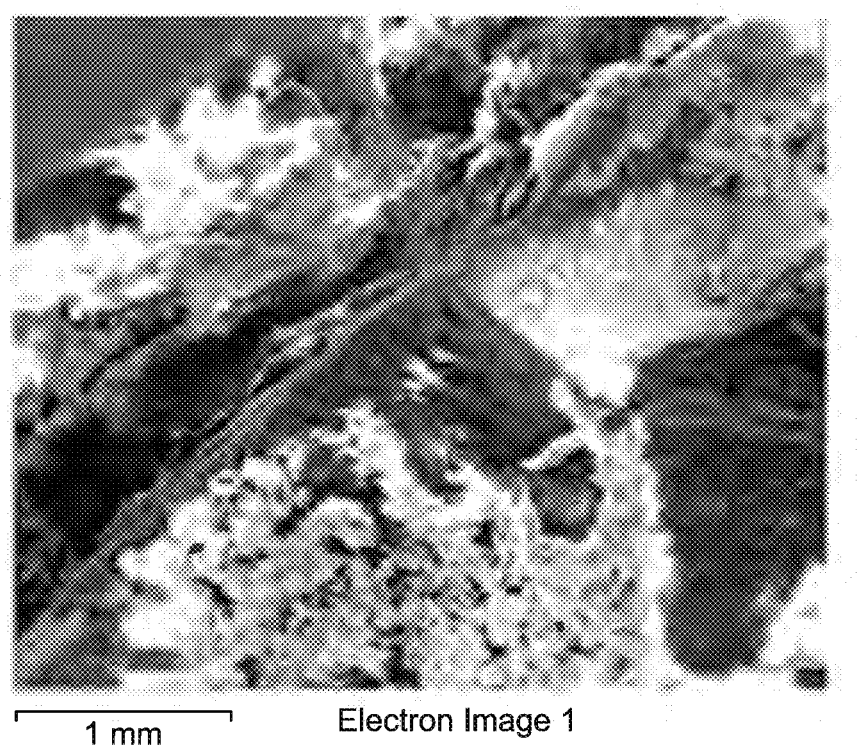
FIG. 17A is a SEM image of the interface appeared after push out test on the resin composite (Exp-RBC 60) to dentin.

In one or more embodiments, the biomedical restoration containing a cured resin composite of the present disclosure in any of its embodiments has a push-out bond strength to dentin of 15-60 MPa, 20-55 MPa, 25-50 MPa, 30-45 MPa, or 35-40 MPa. In one embodiment, the restoration containing a cured resin composite of the present disclosure may have a push-out bond strength to dentin that is 50-90% greater, preferably 60-85% greater, more preferably 70-80% greater than that of a restoration formed with a substantially identical resin composite not reinforced with the fibrous filler. In certain embodiments, the biomedical restoration containing a cured resin composite of the present disclosure may have a push-out bond strength to dentin 10-55% greater, preferably 20-50% greater, more preferably 30-40% greater than that of a restoration formed with a commercial composite (e.g. Filtek Z350, 3M ESPE) (see table 7). Fractured surfaces occurred between the dentin of an extracted tooth and the restoration placed may be found in FIGS. 17A, C, E, G and I, for restoration samples cured by the resin composites containing the polymerizable monomer and different amounts of the fibrous filler disclosed herein.

The examples below are intended to further illustrate protocols for preparing and characterizing fibrous fillers and resin composites filled with the fibrous fillers, and assessing the properties of the fibrous fillers and restorations formed by the cured resin composite. They are not intended to limit the scope of the claims.

EXAMPLE 1

Materials and Methods Related to n-HA/E-Glass Fibers
(i) Preparation of E-Glass

To synthesize nHA/E-glass fibrous material, industrial E-glass fibers were used. The purchased E-glass fibers were initially cut into small pieces using fine surgical blade (no. 12), and they were subsequently heat treated at 150° C. in a drying furnace (WiseVen, South Korea), with a heating ramp of 10° C·min$^{-1}$, to remove any surface impurities. The E-glass fibers were then refluxed with 10% HCl (Sigma Aldrich, USA) for 3 h to form acid activated fibers, which were later washed with distilled water to remove all acidic contents and dried at 110° C. for 2 h. The surface activated E-glass fibers were obtained and stored in desiccator.
(ii) Synthesis of n-HA/E-Glass Fibers Analytical grade calcium nitrate $(Ca(NO_3)_2 \cdot 4H_2O)$ (Sigma Aldrich, USA) and diammonium hydrogen phosphate $((NH_4)_2HPO_4)$ (AppliChem, Germany) were used as precursors for the synthesis of nHA/E-glass. nHA was synthesized following the description below. A Ca/P ratio was set at 1.67 to prepare stoichiometric HA as a control. To synthesize nHA/E-glass fibers, 1.0 M $Ca(NO_3)_2 \cdot 4H_2O$ solution was prepared using deionized water. The pH was maintained at 10 by dropwise addition of ammonium hydroxide [$NH_4OH$; BDH, UK]. The surface activated E-glass fibers were added to this solution in increments. The concentration of the E-glass fibers was 30% or 50% wt/wt. The solution of $Ca(NO_3)_2 \cdot 4H_2O$ with E-glass fibers was allowed to stir for 30 min at ambient temperature (23° C.±2° C.). Then 0.6M $(NH_4)_2HPO_4$ solution was prepared using deionized water, and the pH was maintained at 10 by adding $NH_4OH$. The $(NH_4)_2HPO_4$ solution was added drop wise to $[(Ca(NO_3)_2 \cdot 4H_2O]$ solution at a dropping rate of 2 mL·min$^{-1}$. The reaction mixture was then stirred for 30 min (pH maintained at 10) before refluxing in a domestic microwave oven (Samsung MW101P) at 1000 W for 3 min (15 s ON:OFF). After microwave irradiation, the resulting reaction mixture was filtered, washed with distilled water, and aged in a drying oven at 80° C. for 24 h. The resulting materials with 30 wt % and 50 wt % E-glass fibers were denoted as nHA/E30 and nHA/E50, respectively. All resulting materials were heat treated at 450° C. for 1 h (ramp rate ≈10° C·min$^{-1}$) and cooled down to room temperature (ramp rate ≈10° C·min$^{-1}$). Resulting products (nHA/E30 and nHA/E50) were isolated and characterized for structural, morphological and biological analysis. To confirm the successful synthesis of HA, a sub-group of nHA/E0 (or: nHA) sample was heat treated at 1000° C. (ramp rate ≈10° C.·min$^{-1}$) for 1 h and the sample was denoted as nHA-ht.
(iii) Fourier Transform Infrared Spectroscopy (FTIR)

Fourier Transform Infrared Spectroscopy (FTIR) was conducted to evaluate the chemical structure of nHA/E-glass fibers. Photoacoustic Cell accessory was used with a resolution of 8 cm$^{-1}$. The spectral range was 4000-400 cm$^{-1}$ and scan number was 256. OMINIC software was used to analyze the spectra.
(iv) X-ray Diffraction (XRD)

X-ray diffraction (XRD) technique was used to evaluate phase purity. Analysis was carried out on a diffractometer system PERT-PRO using Goniometer geometry (PW3050/60) at room temperature with Cu K-α radiation. XRD patterns were recorded continuously with 2θ from 20° to 80° with a step size of 0.02°.
(v) Thermogravimetric Analysis (TGA)

Thermogravimetric analysis (TGA) was performed on QEX-600 (TA Instruments, UK) using the platinum pan as reference material. The analysis was carried out between 25°-500° C. at the rate of 100C. min-1 under inert nitrogen environment.
(vi) Scanning Electron Microscope (SEM)

The morphology of prepared materials and presence of nHA particles on the surface of E-glass fibers were investigated by scanning electron microscope (Tescan Vega-3 LMU, Check Republic) at a voltage of 20 KV. Samples were coated (thickness ≈250A°) using a gold-sputter coater (QUORUM) and evaluated at multiple magnifications.
(vii) Cell Viability Test The nHA (or nHA/E0), nHA/E30, and nHA/E50 sample pellets (6×2 mm$^2$) were prepared under a compressive pressure of 60 MPa using a Universal Testing Machine (Testometrics, UK). The pellets were heat treated at 450° C. at a heating ramp of 10° C.·min$^{-1}$ then initially sterilized with a 70/30 ethanol solution for 30 min, and later irradiated with γ-radiations.

The in vitro biocompatibility of nHA (or nHA/E0), nHA/E30, and nHA/E50 samples were investigated using bone marrow derived mesenchymal stem cell (bmMSC, ATCC®

PCS-500-030™) and cellular responses were observed by MTT assay. Cells were cultured in DMEM media supplemented with 10% fetal bovine serum, 1% glutamine, and 1% penicillin/streptomycin (Sigma-Aldrich UK). The cells were allowed to confluent (100%) in tissue cultured flasks and were detached by using trypsin EDTA (Sigma-Aldrich, UK). Immediately before cell seeding the sample pellets were washed 2-3 times with phosphate buffer solution (PBS) and pre-conditioned in DMEM medium for an hour. Cells were seeded into wells of a 24-well plate containing the samples with a seeding density of $1.35 \times 10^4$ cells/mL. The nHA (or nHA/E0) and tissue culture plate (TCP) were considered as positive and negative control, respectively. The cells containing samples were incubated at 37° C. in a 5% $CO_2$ incubator and were analyzed for cell viability at day 3 and day 7 of culture with the materials. The test was conducted in triplets.

To examine the cell attachment capacity on to the scaffolds, 105 bmMSC were loaded on each scaffold for an hour and cultured in 1 mL medium. The medium was then discarded after day 7. The cells/scaffolds were washed once with 1 mL PBS. The cells were fixed in 4% paraformaldehyde for 30 min at 37° C. and rinsed with 1 mL distilled water. The scaffolds were air dried at room temperature overnight. The cells attachment on the scaffolds was observed using SEM.

(viii) MTT Assay Test

For quantitative measurement, an MTT assay was performed individually on all the prepared samples. 0.1 mL of MTT solution was aseptically added to each well and left for incubation at 37° C. for 4 h. Then the cells were lysed with isopropanol. The % viability for each sample was determined in comparison with tissue culture plate (TCP) control. The intensity of the colored solution was measured using a photospectrometer (PR 4100, Bio-Rad, USA) at a wavelength of 570 nm. The assay was set up in triplicate with bmMSC derived from three different rats for each sample. The % viability is represented as mean±SD of three independent experiments.

(ix) In Vitro Osteogenesis Analysis

For osteogenesis analysis, MC3T3-E1 Murine Osteoblasts (RIKEN Bio Resource Centre, Tsukuba, Ibaraki, Japan) were used. This cell line was maintained in α-Minimum Essential Medium (α-MEM) (GIBCO®) supplemented with 10% Fetal Bovine Serum (FBS) (GIBCO®) and 2 mM Glutamine under standard conditions at 37° C. and 5% $CO_2$. The medium was changed every three days and the cells were trypsinized with 0.25% trypsin (TryPLE SelecTM, GIBCO®) after 80% confluence. The pellets were immersed in medium overnight and seeded with MC3T3 E-1 cells, keeping a concentration of $3 \times 10^4$/well in 1 mL of α-MEM medium with 10% FBS. The control (tissue culture plate, TCP) was also treated in a similar manner. The well plates were stored at 37° C. with 5% $CO_2$ and cells were allowed to grow on the pellets for 5 days after which the pellets were removed for RNA extraction. The control samples (cells without pellets) were also removed for RNA extraction.

(x) RNA Extraction

On the $5^{th}$ day of the experiment, total RNA extraction was done with RNA extraction kit (SaMag, Italy) and automated RNA extraction equipment (SaMag, Italy). Each pellet was added to a separate tube. A volume of 220 μL cell lysis buffer was added to the tubes containing the samples and contents of the tubes were mixed by gentle vortex. The tubes were placed in the automated RNA extraction machine. In a reagent cartridge, the lysed cell suspension was sequentially treated with proteinase-K, magnetic beads and wash buffers. At the end of the process, the released RNA was dissolved in RNase free deionized water.

(xi) Inactivation of Contaminating DNA

The DNA contamination was removed by incubating the extracted RNA with DNase-I enzyme. Each RNA sample was incubated at 37° C. for 10 min after addition of 1 μL of DNase-I (Thermo Fisher Scientific, USA) followed by inactivation of DNase-1 at 75° C. for 10 min. A cDNA minus control was also included to exclude the possibility of non-specific amplification of contaminating DNA in the samples.

(xii) Synthesis of cDNA

MMLV Reverse transcriptase (RT) (Thermo Fisher Scientific, USA) was the enzyme used for cDNA synthesis. The reaction conditions contained 2 μL RNA, 4 μL 5× reaction buffer, 2 μL 10 mmol dNTPs mix (Thermo Fisher Scientific, USA), 1 μL Primer (10 μmol/μL), 1 μL MMLV-Reverse Transcriptase (200 U/μL), 1 μL RNase inhibitor (20 U/μL), and 13 μL deionized water. Incubation was done at 42° C. for 30 min and RT inactivation at 70° C. for 5 min. Gene expression of two bone proteins, collagen (Col) Type 1 and osteogenic protein (OP) was measured. Primer sequences of the genes are given in Table 1 and primers were synthesized by Integrated DNA Technologies (IDT), USA.

(xiii) RT-PCR Analysis of Osteoblastic Markers

The PCR Master Mix was prepared in 0.2 mL PCR tubes. The volume of reagents used to make up the PCR Master Mix and the reaction conditions contents were: 10 μL SYBER green PCR mix (Thermo Fisher, USA), 1 μL (10 μmol/μL) Forward Primer IDT (USA), 14 (10 μmol/μL) Reverse Primer (IDT, USA), 3 μL cDNA, and 5 μL DEPC treated water. Real-time PCR was done in Rotor Gene-Q machine (Qiagen, USA) in 20 μL reaction mix in 0.2 mL tubes. The samples were run with the following parameters: Initial denaturation at 95° C. for 5 min and amplification of 35 cycles with denaturation at 95° C. for 15 s, annealing/extension at 60° C. for 50 s. GAPDH, a housekeeping gene, was run as the control. The Ct values of the target (OP and Col) and the reference (GAPDH) genes were used for data analysis. The relative levels of mRNA expression were quantified by comparison with the internal control (GAPDH).

TABLE 1

PCR Primer Sequences, F (forward) R (reverse).

| Sr. no | Gene | Primer Sequence |
|---|---|---|
| 1 | Mur OP-F | 5'-TCTGATGAGACCGTCACTGC |
| 2 | Mur OP-R | 5'-AGGTCCTCATCTGTGGCATC |
| 3 | Mur-Col-1a1-F | 5'-GAGAGGTGAACAAGGTCCCG |
| 4 | Mur-Col-1a1-R | 5'-AAACCTCTCTCGCCTCTTGC |
| 5 | Mur GAPDH-F | 5'-AAGGTCATCCCAGAGCTGAA |
| 6 | Mur GAPDH-R | 5'-CTGCTTCACCACCTTCTTGA |

EXAMPLE 2

Results Related to n-HA/E-Glass Fibers
(i) Fourier Transform Infrared Spectroscopy The comparative FTIR spectra (FIG. 1) showed the characteristic peaks of HA. In nHA (or nHA/E0), nHA/E30 and nHA/E50 spectra, the broad band in the range 3100-3400 cm$^{-1}$ and peak at 1640 cm$^{-1}$ corresponded to adsorbed water. The less intense peak of O—H were observed at 3570 cm$^{-1}$, whereas, nHA-ht showed stretching peak of O—H in the same region with high intensity. Peaks at 1455 cm$^{-1}$ and 1412 cm$^{-1}$ were attributed to adsorbed $CO_3^{-2}$ ions on the surface and were observed in nHA/E0, nHA/E30, and nHA/E50. However, after heat treatment, these peaks became less intense for nHA-ht. In addition, P—O was confirmed by the characteristic peaks at 1095, 1053, 1026, 961, 564 and 470 cm$^{-1}$. Peaks at 1095 cm$^{-1}$ and 1026 cm$^{-1}$ were assigned to triply degenerated ($v_3$) asymmetric stretching mode of P—O bond. The 961 cm$^{-1}$ band indicated a non-degenerated ($v_1$) P—O symmetric stretching mode. Peak at 564 cm$^{-1}$ revealed presence of triply degenerated ($v_4$) bending mode of P—O—P bond. The intensity of P—O peaks decreased with increasing concentration of E-glass fibers, while no peak shifting was observed. The spectrum of nHA-ht showed that peaks at 1095 cm$^{-1}$ and 1040 cm$^{-1}$ became well defined, which matched the characteristic peaks of HA.

(ii) X-Ray Diffraction

The comparative XRD patterns of nHA (or nHA/E0), nHA-ht, nHA/E30 and nHA/E50 are given in FIGS. 2A-D. The diffractogram of heat treated nHA-ht had a good match with the pattern of phase pure hydroxyapatite [JCPDS pattern 09-0432] and the peak assignments were confirmed with Miller index. Broad peaks in the XRD pattern of nHA at 25.96 (002) and 31.90 (211) indicated amorphous nature of apatite. The change in the pattern of nHA heat treated at up to 450° C. was not significant. However, when heat treated at 1000° C., peaks became intense exhibiting the crystalline nature. No phase impurity was observed in nHA structure. The patterns of nHA/E30 and nHA/E50 both showed the characteristic peaks of HA. Furthermore, it was observed that intensity of HA peaks decreased with increasing concentration of E-glass. The intensity at 2θ≈31.90° peak of HA/E30 and HA/E50 was 245 and 225, respectively.

(iii) Thermogravimetric Analysis (TGA)

Figure 3:
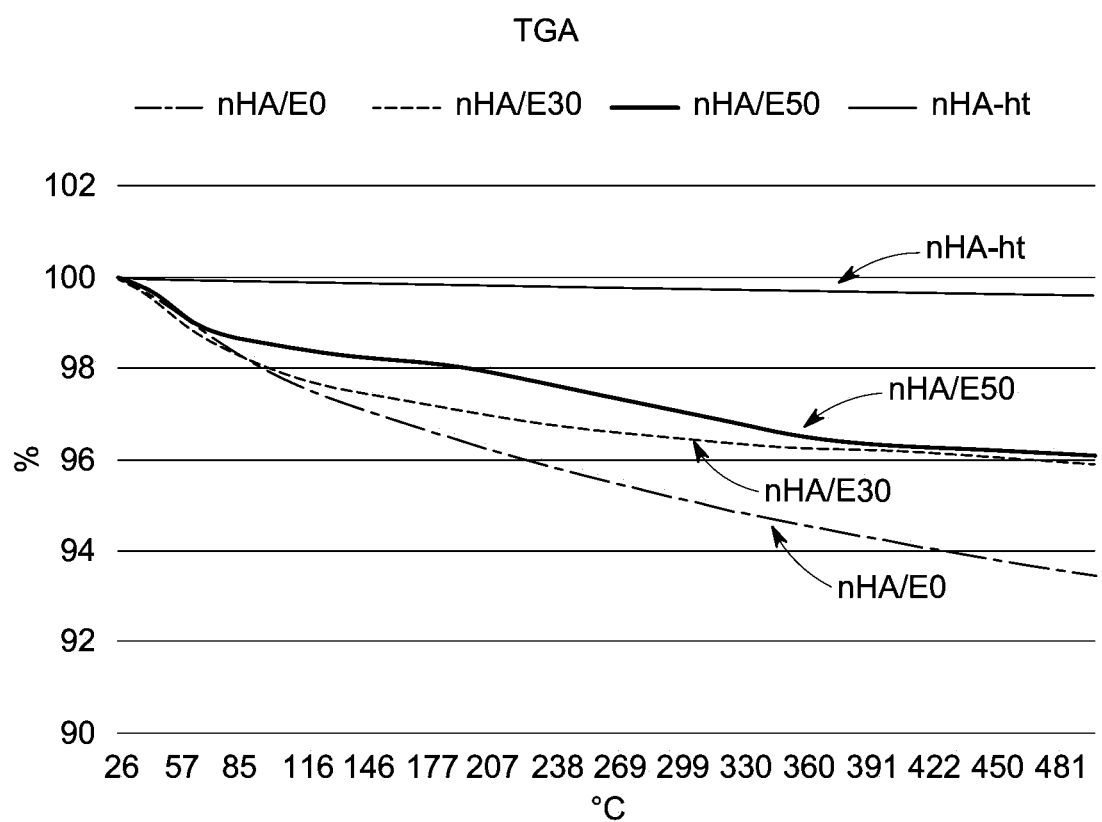
FIG. 3 is an overlay of thermogravimetric analysis (TGA) curves of nHA/E0 (or nHA), nHA-ht, nHA/E30, and nHA/E50.

The comparative weight loss profiles (TGA graphs) of nHA (or nHA/E0), nHA-ht, nHA/E30, and nHA/E50 are shown in FIG. 3. The nHA/E0 showed a weight loss at almost 6.5% in the temperature range tested (26-480° C.), while nHA-ht, nHA/E30, and nHA/E50 exhibited a weight loss at 0.5%, 5.1%, and 4.9%, respectively in the same temperature range. During the synthetic reaction, ammonium nitrate ($NH_4NO_3$) was obtained as a by-product. Removal of $NH_4NO_3$ (M.P. ≈170° C.) partially contributed to the weight loss up to 200° C. The weight loss observed between 200-280° C. was due to the removal of physically adsorbed water. At 300° C., the nHA/E50 experienced a 3% weight loss, whereas, nHA/E30 experienced a 4.5% loss, which led to the conclusion that the presence of E-glass fiber at a higher concentration thermally stabilized the fibrous material.

(iv) Scanning Electron Microscopy

Figure 4A:
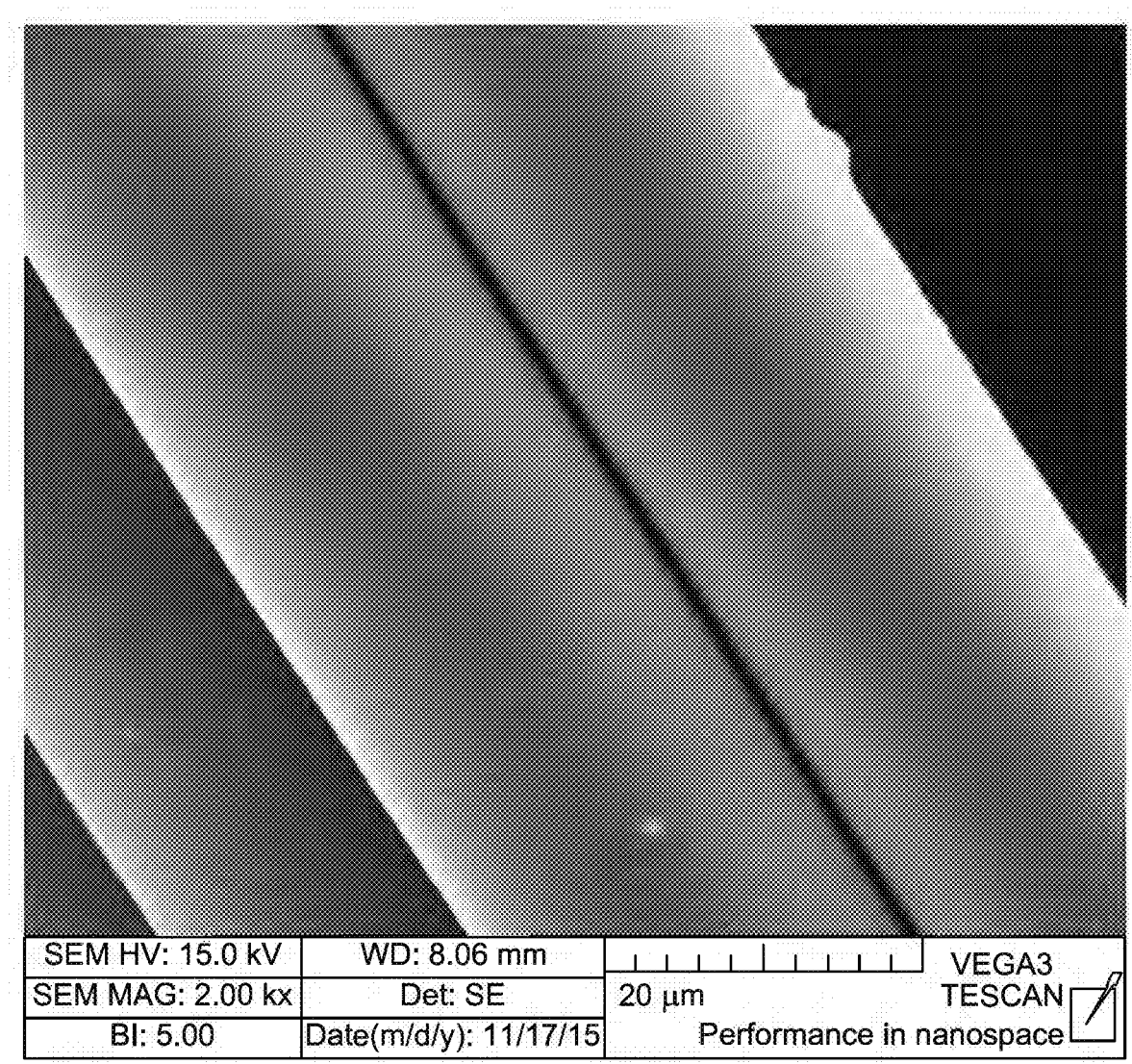
FIG. 4A is a scanning electron microscopy (SEM) image of E-glass fibers.
Figure 4B:
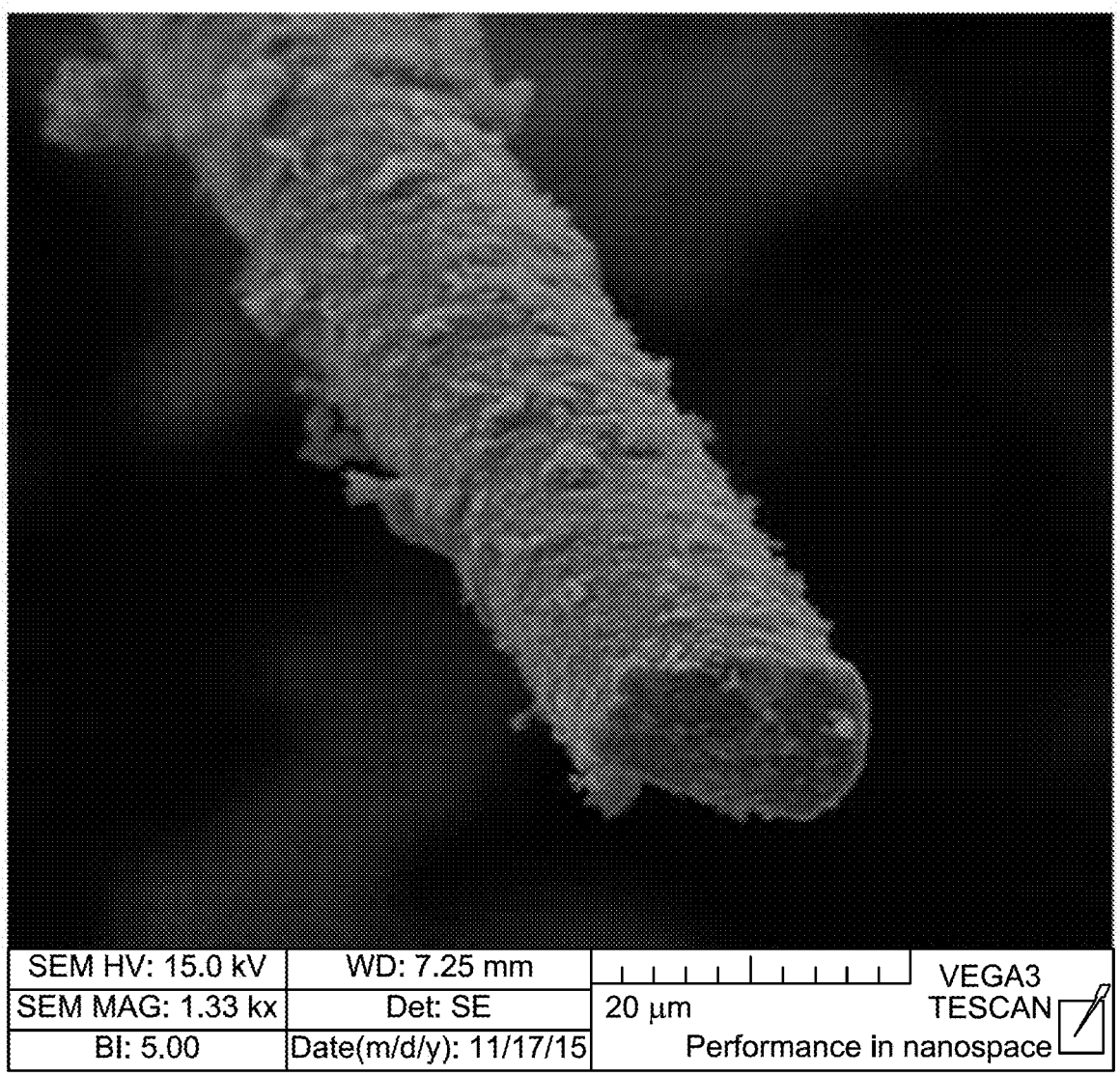
FIG. 4B is a SEM image of nano hydroxyapatite disposed on E-glass fibers.
Figure 4C:
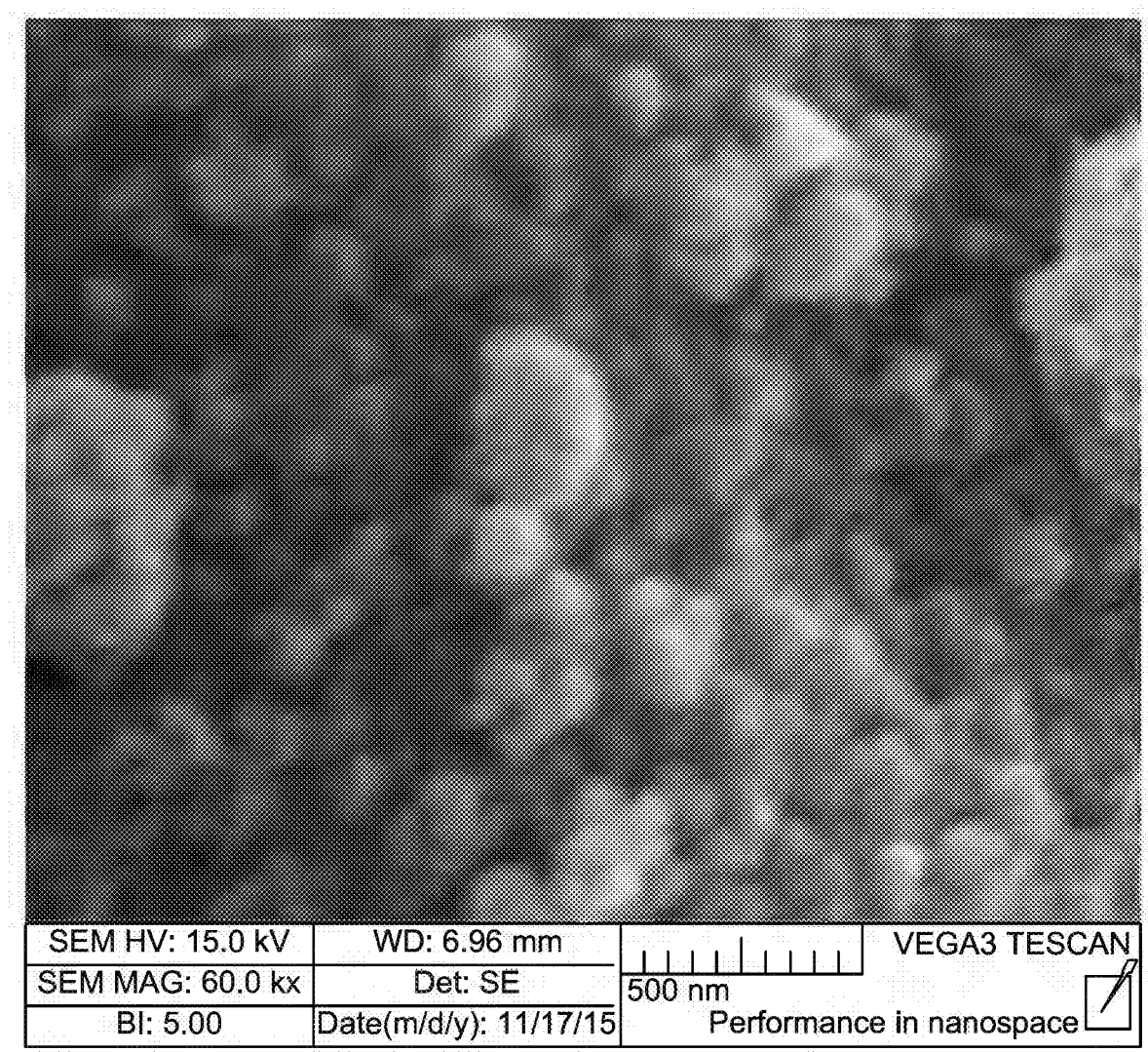
FIG. 4C is a SEM image showing the shape and size of nano hydroxyapatite particles disposed on E-glass fibers.
Figure 4D:
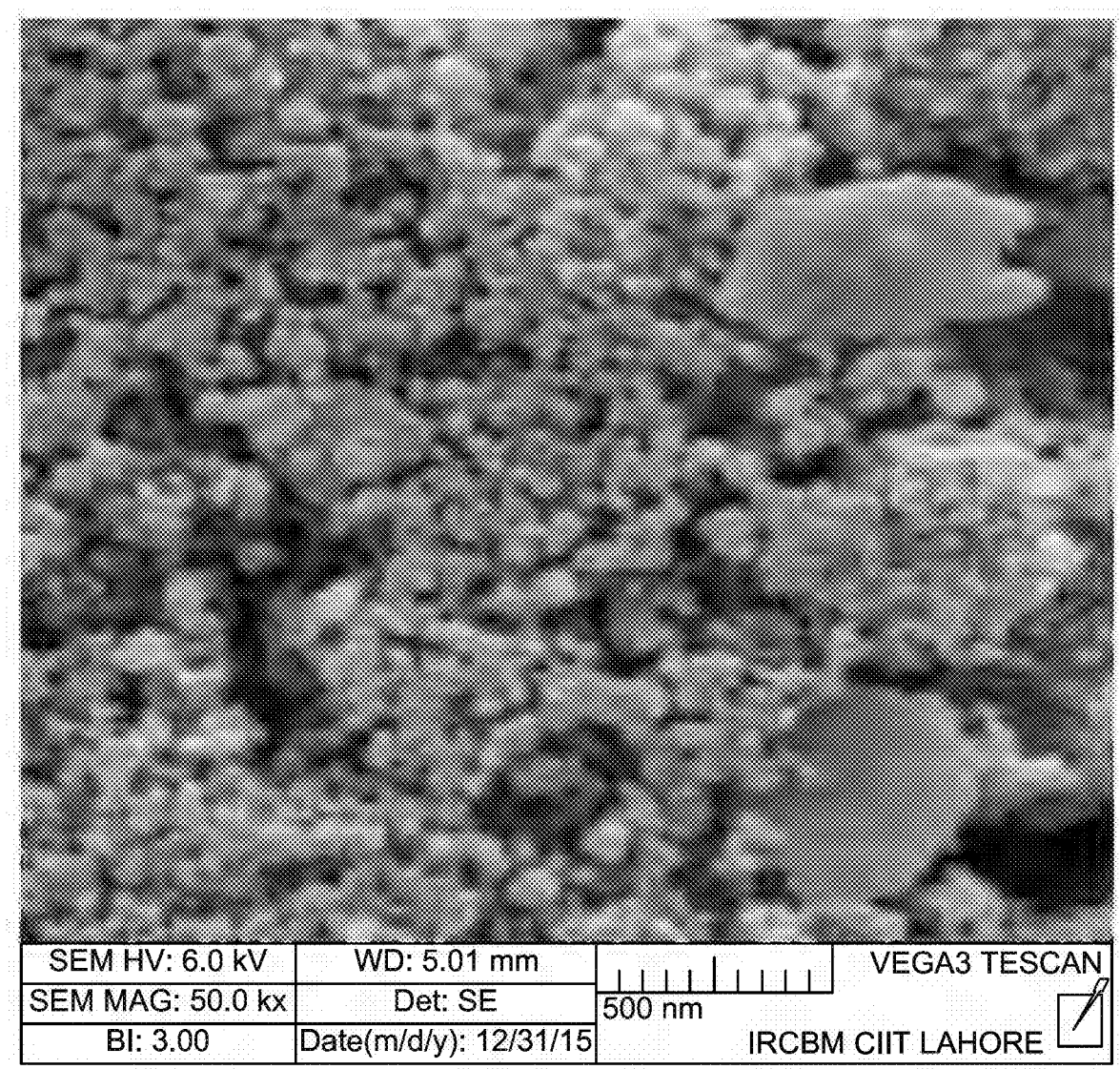
FIG. 4D is another SEM image showing the shape and size of nano hydroxyapatite particles disposed on E-glass fibers.

The SEM image of FIG. 4A showed E-glass fibers after heat treatment having a smooth surface. The fiber samples were cut with sharp blade. The edges of the fibers maintained a smooth surface and the surface of the fibers was homogenous. The diameter of E-glass fibers was 20 μm. After nHA deposition on the surface of E-glass fibers, it was observed that the surface was full covered by nHA (FIG. 4B). The size of deposited particles on examined samples was approximately 50 nm, which further confirmed the deposition and attachment of nano-particles on E-glass surface (FIGS. 4C and 4D). The SEM image of nHA showed nano-structured particles with an observed size of 20-50 nm.

(v) Cell Viability

Figure 5:
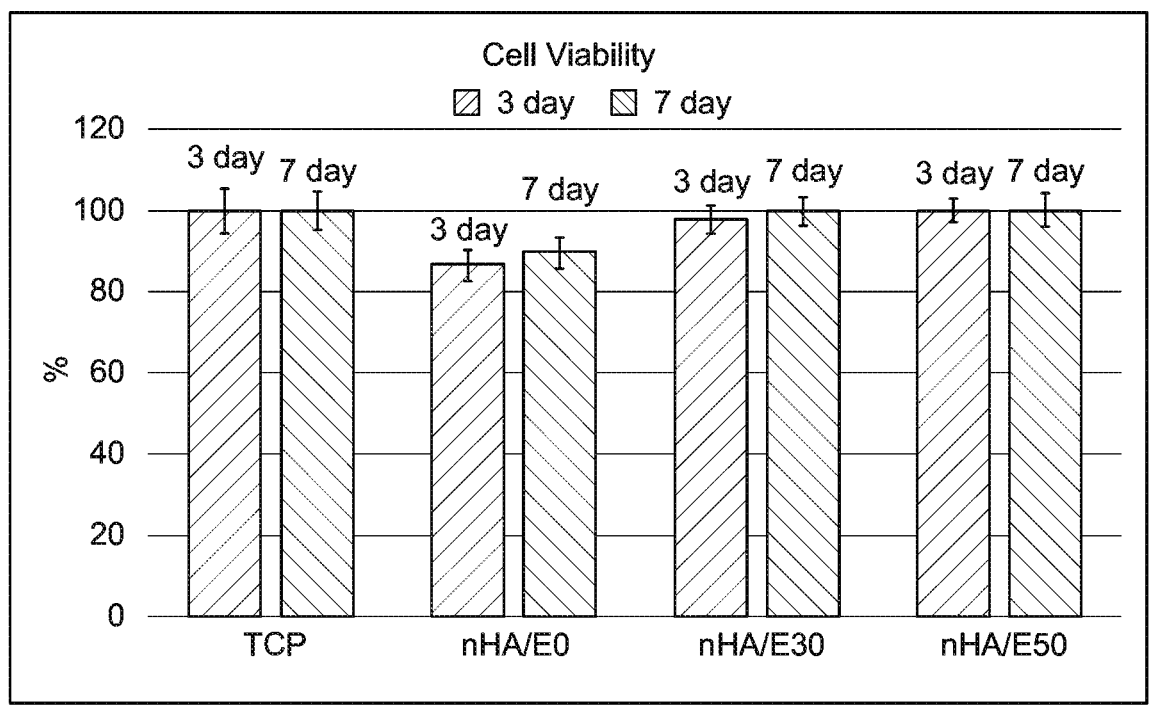
FIG. 5 is a bar graph comparing cell viabilities of bone marrow derived mesenchymal (bmMSC) stem cells after day 3 and day 7 treatments with tissue culture plate (TCP), nHA/E0 (or nHA), nHA/E30, and nHA/E50.
Figure 6A:
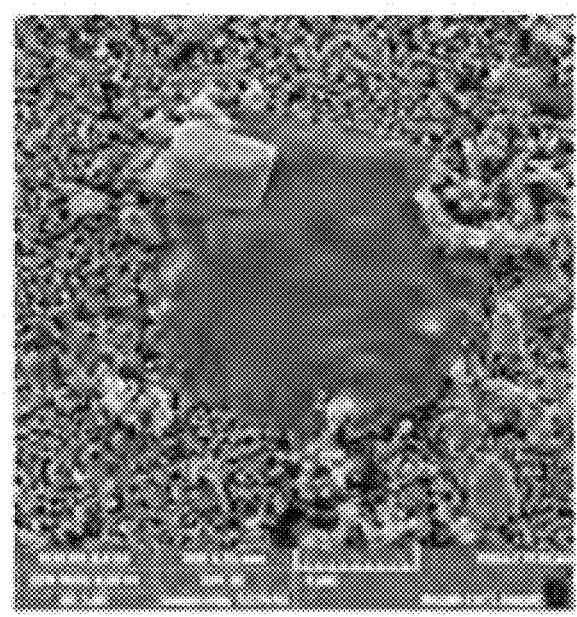
FIG. 6A is a SEM image showing cell attachment of bmMSC to nHA/E0 (or nHA).
Figure 6B:
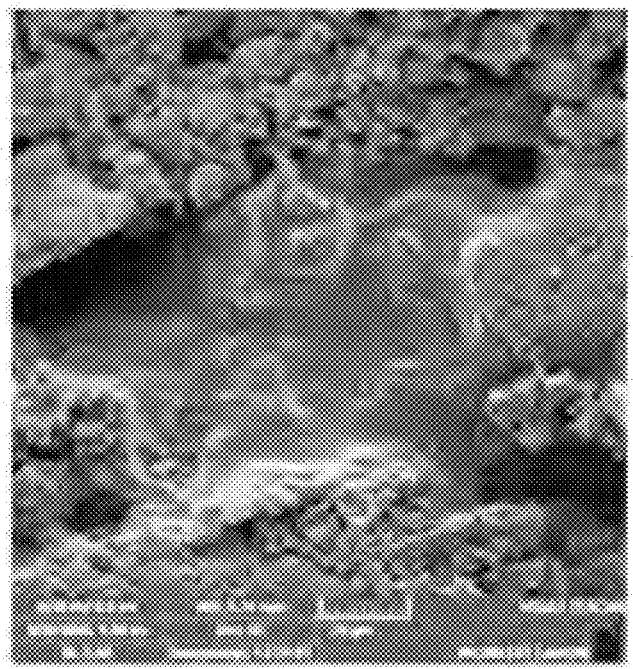
FIG. 6B is a SEM image showing cell attachment of bmMSC to nHA/E30.
Figure 6C:
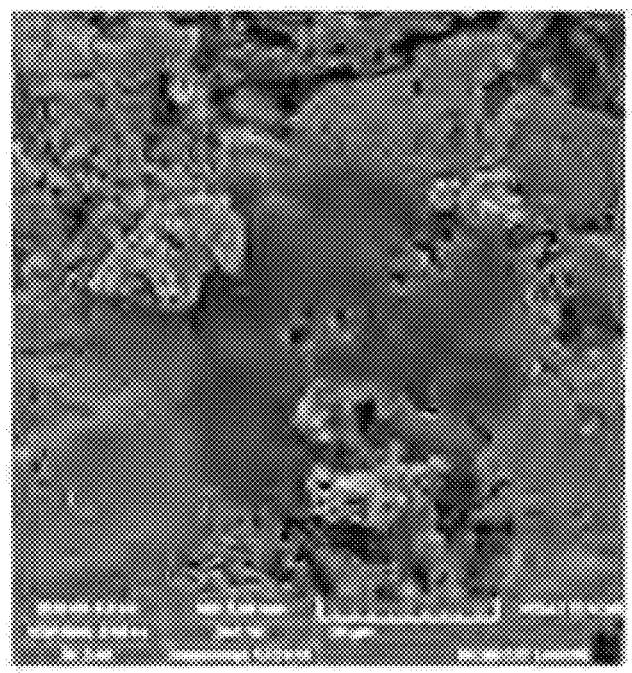
FIG. 6C is a SEM image showing cell attachment of bmMSC to nHA/E50.
Figure 6D:
FIG. 6D is a SEM image showing proliferation of bmMSC on nHA/E0 (or nHA).
Figure 6E:
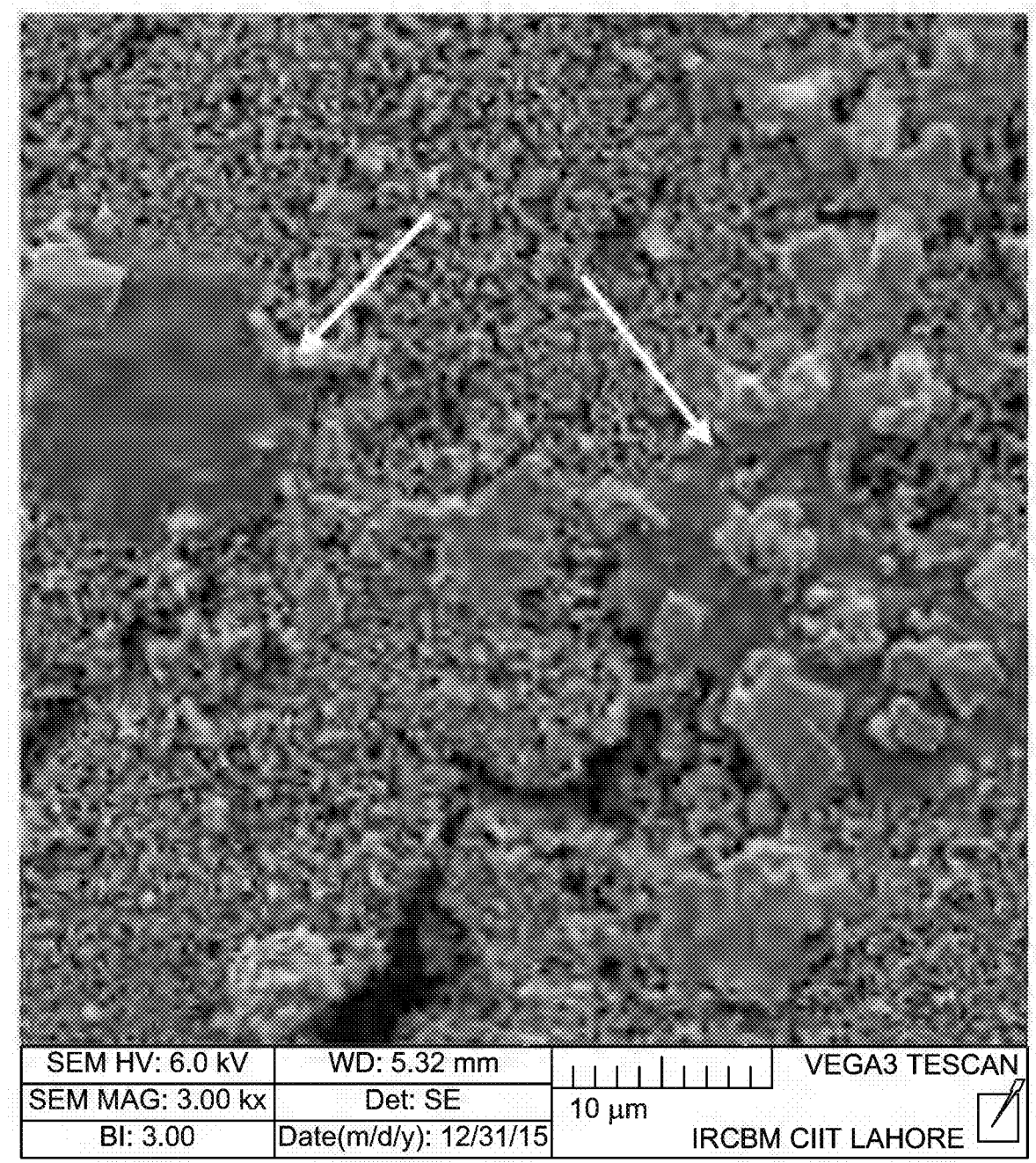
FIG. 6E is a SEM image showing proliferation of bmMSC on nHA/E30.
Figure 6F:
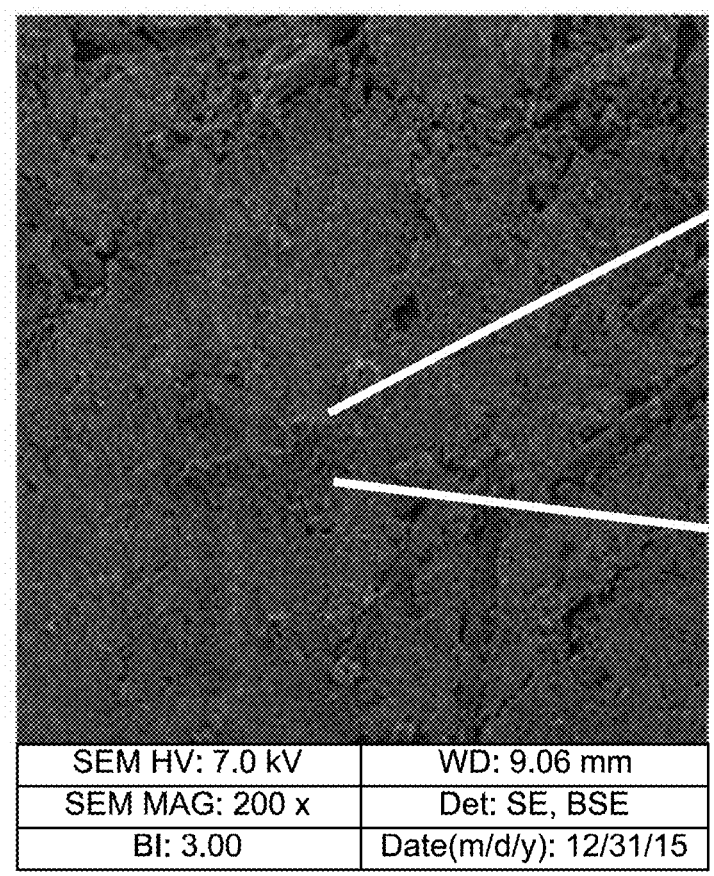
FIG. 6F is a SEM image showing proliferation of bmMSC on nHA/E50.
Figure 6G:
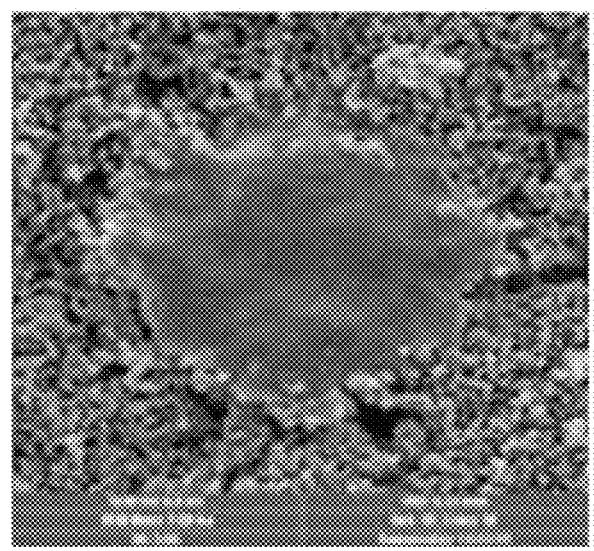
FIG. 6G shows a magnified view of the sample in FIG. 6F.

FIG. 5 compared the cell growth (% variability) on all tested samples. It was observed that after incubation, all samples showed a positive response. For nHA samples, the cell viability was 85.6% after 3 days and 90% after 7 days. For nHA/E30, the cell viability was 98% and 100% on day 3 and 7, respectively. For nHA/E50, the cell viability was 100% on both day 3 and 7. The cell proliferation/attachment and morphology of the sample surfaces were observed after day 7 of culture. SEM images (FIGS. 6A-F) showed the presence of cell attachment and cell proliferation on nHA and nHA/E-glass samples.

(vi) Osteogenesis Analysis

The results of OP and Col gene expression and the mathematical calculations of relative expression ratio (R) between the control (unexposed) and the test samples (exposed) are presented in Table 2 and 3, respectively. The highest OP gene relative expression ratio was seen in nHA/E0 (15.4±0.99) followed by nHA/E30 (7.56±0.97) and nHA/E50 (4.57±0.68). The highest Col gene expression ratio was seen in nHA/E0 (15.9±0.74) followed by nHA/E30 (4.53±0.47) and nHA/E50 (2.75±0.29). OP and Col gene expression decreased significantly (p<0.001) with decreasing concentration of HA.

TABLE 2

Summary of the results of Ct and ratio (R) of OP gene expression in murine osteoblasts exposed to various concentrations of E-glass and nano-hydroxyapatite (nHA)

| E-Glass | HA | Gene | Ct test | Ct control | ΔCt[#] | $2.0^{\Delta Ct}$ | Ratio (R)[@] | Expression % |
|---|---|---|---|---|---|---|---|---|
| nHA/E0 | 100% | Target (OP) | 27.15 | 16.81 | −10.34 | 0.00077 | 15.4 ± 0.99 | 100% |
|  |  | Reference (GAPDH) | 31.41 | 17.23 | −14.18 | 0.00005 |  |  |
| nHA/E30 | 70% | Target (OP) | 24.36 | 16.81 | −7.55 | 0.00535 | 7.56 ± 0.97 | 51.9% |
|  |  | Reference (GAPDH) | 27.68 | 17.23 | −10.45 | 0.00072 |  |  |
| nHA/E50 | 50% | Target (OP) | 21.66 | 16.81 | −4.85 | 0.03472 | 4.57 ± 0.68 | 29.4% |
|  |  | Reference (GAPDH) | 24.26 | 17.23 | −7.03 | 0.00765 |  |  |

[#](Ct control − Ct test)
[@]$2.0^{\Delta Ct \, (target)}/2.0^{\Delta Ct \, (reference)}$

TABLE 3

Summary of the results of Ct and ratio (R) of Col gene expression in murine osteoblast exposed to various concentrations of E-glass and nano-hydroxyapatite (nHA)

| E-Glass | HA | Gene | Ct test | Ct control | $\Delta Ct^{\#}$ | $2.0^{\Delta Ct}$ | Ratio (R)@ | Expression % |
|---|---|---|---|---|---|---|---|---|
| nHA/E0 | 100% | Target (Col) | 27.16 | 19.92 | −7.24 | 0.00662 | 15.93 ± 0.74 | 100% |
|  |  | Reference (GAPDH) | 31.40 | 20.18 | −11.22 | 0.00042 |  |  |
| nHA/E30 | 70% | Target (Col) | 30.19 | 19.92 | −10.27 | 0.00080 | 4.53 ± 0.47 | 28.03% |
|  |  | Reference (GAPDH) | 32.59 | 20.18 | −12.41 | 0.00018 |  |  |
| nHA/E50 | 50% | Target (Col) | 28.51 | 19.92 | −8.58 | 0.00261 | 2.75 ± 0.29 | 17.63% |
|  |  | Reference (GAPDH) | 30.22 | 20.18 | −10.04 | 0.00094 |  |  |

(Ct control − Ct test)
@$2.0^{\Delta Ct\ (target)}/2.0^{\Delta Ct\ (reference)}$

EXAMPLE 3

Discussions Related to n-HA/E-Glass Fibers

Bioactive materials have been extensively used due to their structural support, cell delivery capability, and tissue regeneration possibilities. In the current disclosure, surface grafting of E-glass fiber with nHA has been successfully achieved by using microwave irradiation technique. FTIR and XRD revealed the presence of nHA on E-glass surface. In addition, changes were observed in intensity of peaks and crystallinity with increasing concentration of E-glass.

The microwave reaction conditions were set at 1000 W for 3 min to avoid undesired changes on molecular structures. Therefore, resulting materials i.e. nHA/E30 and nHAE50 were obtained in a short amount of time with less chances of side reactions. In the current disclosure, surface activated E-glass fibers which had silica as a main component abundantly present on the fiber surface were used. In generally silica is covered with hydroxyl (OH) groups able to form silanols (either free or bonded with neighboring silanol). The microwave irradiation technique was used purposely. When E-glass was exposed to microwave irradiation along with hydroxyapatite solution, dielectric heating of polar —$OH^-$ and silanol groups might result in energy transfer from these groups to the surrounding molecules. Microwave irradiation would activate these functional groups, transfer energy to the groups presented in hydroxyapatite, and subsequently stimulate adhesion of nHA on E-glass surface.

After microwave assisted synthesis of nHA/E glass, the resulting materials were heat treated at 350° C. to remove any unreacted ammonia and/or water molecules present on surface. It was reported that sub-surface water would desorb at 300° C. [Nishioka G M, Schramke J A. Thermodesorption of water from silicate surfaces. Journal of Colloid and Interface Science 1985;105:102-11, incorporated herein by reference in its entirety]. Heat treatment of E-glass based material at a high temperature might change the physical and mechanical properties of the material. However, a precise mechanism that explains the strength loss of heat-treated glass fiber is not yet fully established. It was reported that treating the fiber at around 500° C. caused a contraction and loss of strength [Thomason J L, Kao C C, Ure J, Yang L. The strength of glass fibre reinforcement after exposure to elevated composite processing temperatures. J Mater Sci 2014;49:153-62; and Thomason J, Jenkins P, Yang L. Glass fibre strength—A review with relation to composite recycling. Fibers 2016;4:18, each incorporated herein by reference in their entirety]. The increase in temperature was inversely proportional to the microporosity and also affected the surface area and bioactive properties of nHA. Heat treatment at 450° C. did not result in a dense structure. Therefore, the nHA particles on the surface might have the porosity necessary to stimulate apatite deposition.

SEM images (FIGS. 4C, D) showed a homogenous deposition of nano spherical particles onto the surface of cleanly cut E-glass fibers. The particle size of nHA maximized the ratio of surface area to volume, allowing a high percentage of atoms to be present on the surface [Liu D-M, Troczynski T, Tseng W J. Water-based sol-gel synthesis of hydroxyapatite: process development. Biomaterials 2001;22:1721-30, incorporated herein by reference in its entirety]. Agglomerated particles were also observed, due to high surface energy of the HA nanoparticles that tend to agglomerate to diminish this energy. The nanoscale-engineered surface can modulate and control the interactions between biomedical materials and biological tissues. Further, nHA promotes ion exchange and cellular response in a physiological environment [Barros J, Grenho L, Manuel C M, Ferreira C, Melo L, Nunes O C, et al. Influence of nanohydroxyapatite surface properties on Staphylococcus epidermidis biofilm formation. J Biomater Appl 2014;28:1325-35, incorporated herein by reference in its entirety]. Nanoparticles having a high surface area may have increased chemical interactions with an organic matrix. Similarly, binding capacity of the presently disclosed bioactive E-glass fibers and resin matrix may be strengthened. The incorporation of these bioactive fibers will not only enhance the mechanical properties but also play a significant role to achieve a biomimetic approach for restoration and implant applications.

The prepared nHA/E-glass materials showed compatibility with cells. The presence of E-glass also enhanced cell viability. As shown in SEM images (FIGS. 6A-F) the cells proliferated on surface and a multi-layered cell matrix could be observed on day 7. Culturing cells directly on the surface of nHA/E-glass indicated a synergistic interaction among the cells, nHA, and E-glass fibers. The hydrophilicity, porosity and roughness of nHA all have an impact on cell behavior [Chan Y H, Lew W Z, Lu E, Loretz T, Lu L, Lin CT, et al. An evaluation of the biocompatibility and osseointegration of novel glass fiber reinforced composite implants: In vitro and in vivo studies. Dental materials, 2017, incorporated herein by reference in its entirety]. The adhered morphological cells spread with some extensions, indicating better attachment of cells on materials surface. The surfaces of pellets were showing development of a new layer as samples were immersed in culturing media. The cell culturing media in static condition has a tendency to favor dissolution process of nHA [da Silva H M, Mateescu M, Ponche A, Damia C, Champion E, Soares G, et al. Surface transformation of silicon-doped hydroxyapatite immersed in culture medium under dynamic and static conditions. Colloids and surfaces B, Biointerfaces 2010;75:349-55, incorporated herein by reference in its entirety], afterward precipitation of ions due to mineral nucleation theory and it promotes a formation of new apatite layers over the surface.

The results of biological study clearly indicated that nHA and novel nHA/E-glass fibers were highly biocompatible in nature and supported the growth of cells. This could be attributed to the osteogenic nature of nHA which allowed attachment, proliferation and differentiation of the murine osteoblasts. Adhesion of nHA on E-glass fibers has effectively imparted biocompatibility, which was the purpose of this novel biomaterial. The concentration tested herein is high enough to improve the mechanical properties without compromising the osteogenity of nHA. These results showed potential applications on implant and reinforcing agent in restorative materials. Since dental restorations and prosthesis are subjected to thousands of cycles of stress per day, a new material with high mechanical and bioactive properties which can tolerate the stress with high reinforcing efficiency is desirable.

This disclosure deals with a novel combination of nHA and E-glass fibers and its ability to be used as a scaffold for tissue engineering and clinical applications. MC3T3-E1 cells were used as they are osteoblastic in nature and capable of forming mineralized bone tissue in vitro [Czekanska E M, Stoddart M J, Ralphs J R, Richards R and Hayes J 2014 A phenotypic comparison of osteoblast cell lines versus human primary osteoblasts for biomaterials testing Journal of Biomedical Materials Research Part A 102 2636-43, incorporated herein by reference in its entirety]. Furthermore, an automated method for RNA extraction employing anti RNA coated magnetic beads were used. The method is quick, sensitive, and relatively cheap. Further, the quality of RNA can provide good evidence of synthesis of proteins [Liu W and Saint D A 2002 A new quantitative method of real time reverse transcription polymerase chain reaction assay based on simulation of polymerase chain reaction kinetics Analytical Biochemistry 302 52-9, incorporated herein by reference in its entirety. Any presence of residual DNA in a sample can give rise to false positive results. Therefore, an additional step of DNAase treatment to remove any contamination of DNA was also performed. The results of the current disclosure clearly indicated that nHA/E0 and novel nHA/E-glass fibers were highly osteogenic in nature and supported the growth of murine osteoblasts. The PCR results were expressed as a ratio of gene expression between the murine osteoblasts exposed and unexposed to the osteogenic material. The relative quantification method was used and a normally expressed "housekeeping" gene (GAPDH) was used. Relative quantification is recommended in order to understand the physiological changes in gene expression. OP is a 34-kDa highly phosphorylated glycoprotein which forms a major component of bone and it progressively develops during the formation and remodeling of bone [Chen J, Singh K, Mukherjee B B and Sodek J 1993 Developmental expression of Osteopontin (OPN) mRNA in rat tissues: Evidence for a role for OPN in bone formation and resorption Matrix 13 113-23, incorporated herein by reference in its entirety]. The highest relative expression ratio of OP by MC3T3 E-1 cells was seen for nHA/E0. This could be attributed to the osteogenic nature of nHA, which allowed attachment, proliferation, and differentiation of the murine osteoblasts.

The relative expression ratio for OP decreased as the concentration of E-glass fibers increased. There was a significant difference among the ratios in nHA/E0, nHA/E30, and nHA/E50. This showed that the nHA/E50 stimulated the cells only 4.57 folds compared to the control. As the concentration of E-glass fibers in the discs increased, the concentration of nHA was reduced. This reduced the osteogenic content as E-glass fibers are inherently inert [Khan A S, Azam M T, Khan M, Mian S A and Ur Rehman I 2015 An update on glass fiber dental restorative composites: a systematic review Materials Science & Engineering. C, Materials for biological applications 47 26-39]. Nevertheless, these fibers supported the growth of cells and did not restrict their proliferation.

The results for Col gene expression in all the materials followed a similar pattern to OP. The highest ratio was seen in nHA/E0, followed by nHA/E30 and nHA/E50. This trend further augmented the ability of the novel material to induce osteoblastic cells to express osteogenic proteins like collagen. Expression of Col further proved that the cells were proliferating and were able to maintain their phenotype. nHA is osteoconductive, osteointegrative, and in some cases also osteoinductive [Gerhardt L-C and Boccaccini A R 2010 Bioactive glass and glass-ceramic scaffolds for bone tissue engineering Materials 3 3867-910, incorporated herein by reference in its entirety]. It had effectively up-regulated the expression of both OP and Col in this type of experiment, thus it was established that in the presence of nHA/E-glass the expression was also observed. For nHA/E0 only, Col expression was slightly greater as compared to OP, whereas for both nHA/E30 and nHA/E50, OP expression was greater in comparison to Col. When multiple genes are being expressed, they may have a competitive effect on each other and may not have an improved expression in all cases [Xu M, Zhang Y, Zhai D, Chang J and Wu C 2013 Mussel-inspired bioactive ceramics with improved bioactivity, cell proliferation, differentiation and bone-related gene expression of MC3T3 cells Biomaterials Science 1 933-41, incorporated herein by reference in its entirety]. The gene expression profiles of all samples were similar as all stimulated MC3T3 E-1 cells proliferated and produced OP and Col type 1. Adhesion of nHA on E-glass fibers has effectively imparted osteogenecity to this novel biomaterial.

EXAMPLE 4

Methodologies Related to nHA/Eglass Based Dental Resin Composites (i) Silane Grafting of nHA/Eglass A 1.0 vol % of 3-methacryloxypropyltrimethoxysilane (Sigma Aldrich, St. Louis city, USA) solution was prepared using a pre-prepared solvent mixture of 90 vol % ethanol and 10 vol % deionised water. The pH of the solvent mixture was adjusted to 4 using 3.0 M acetic acid. The silane solution was stirred and allowed to hydrolyze (activate) for 1 h. The nHA/Eglass fibrous fillers were then added and dispersed via ultra-sonication for 15 min. The reaction mixture was subsequently stirred for 24 h at room temperature. After the silane grafting process, the reaction mixture was filtered and rinsed with absolute ethanol to remove physically adsorbed silanes. The sample was dried overnight at room temperature and then dried at 60° C. in an oven for 72 h to enhance the condensation of surface silanol molecules and to remove any remaining solvent.

(ii) Synthesis of nHA/Eglass Based Dental Resin Composites

In this disclosure, all chemicals (including monomers and photo-initiators) to prepare the experimental resin and resin-based composites (RBCs) were of analytical grade and purchased from Sigma Aldrich, USA. The resin materials included dental resin monomers i.e. (2,2-bis[4-(2-hydroxy-3-methacrylyloxypropoxy)phenyl] propane (bis-GMA), triethylene glycol dimethacrylate (TEGDMA), urethane dimethacrylate (UDMA). The initiators used were camphorquinone (CQ), and 4-ethyl dimethylamino benzoate (EDBA). The description of these chemicals is given in Table 4.

TABLE 4

Description of chemicals used in this disclosure to prepare resin composites

| Chemicals | Abbreviation | Company |
|---|---|---|
| (2,2-bis[4-(2-hydroxy-3-methacrylyloxypropoxy)phenyl] propane | bis-GMA | Sigma Aldrich |
| Triethylene glycol dimethacrylate | TEGDMA | Sigma Aldrich |
| Urethane dimethacrylate | UDMA | Sigma Aldrich |
| Camphorquinone | CQ | Sigma Aldrich |
| 4-ethyl dimethylamino benzoate | EDBA | Sigma Aldrich |

The composite based on dimethacrylate resin matrixes including bis-GMA, UDMA, and TEGDMA was prepared at 40:35:25 ratio. The resin components were stirred at ambient temperature under dark for 30 min. 0.5 wt % camphorquinone as an initiator and 0.5 wt % 4-ethyl benzoate dimetilamiono (EDBA) were then added to the resin. The resin monomer mixtures were kept in dark to avoid immature polymerization. The unfilled resin was denoted as CT-UF.

To prepare resin composites disclosed herein (experimental resin-based composites, or Exp-RBCs), resinous solution was initially stirred at room temperature to get a homogenous solution or to prevent any sedimentation. Then the fibrous filler (nHA/E-glass fiber) was added as reinforcing agents. The final ratio of the fibrous filler (nHA/E-glass fiber) in the resin composites was 40%, 50%, and 60% by weight, which were denoted as Exp-RBC 40 (40%), Exp-RBC 50 (50%) and Exp-RBC 60 (60%), respectively.

The fibrous filler was added in increments. After complete addition, the resin composite material was stirred at room temperature for 24 hours. After overnight stirring, the obtained Exp-RBC resin composite pastes i.e. Exp-RBC 40, Exp-RBC 50, and Exp-RBC 60 were packed in air tight and dark vials for further use. The composition of materials used in the current disclosure is summarized in Table 5.

TABLE 5

Composition of materials used in the current disclosure

| Materials | Composition (wt %) |
|---|---|
| CT-UF | 100% matrix based on dimethacrylate resins (bis-GMA:UDMA:TEGDMA) |
| Exp-RBC 40 | 60% matrix based on resins (bis-GMA:UDMA:TEGDMA); 40% based on silanized nHA/E glass fibers |
| Exp-RBC 50 | 50% matrix based on resins (bis-GMA:UDMA:TEGDMA); 50% based on silanized nHA/E glass fibers |
| Exp-RBC 60 | 40% matrix based on resins (bis-GMA:UDMA:TEGDMA); 60% based on silanized nHA/E glass fibers |

The samples were prepared in a Teflon mold of various dimensions as per analysis requirement. The mold was placed on glass slab and experimental resin composites were poured in mold carefully. Single increment of 2 mm layer of the resin composite was condensed in mold, and covered with Mylar strip after complete filling to avoid oxygen inhibition layer and to achieve a smooth surface. The sample was cured on both sides using high intensity blue light (LED, Woodpecker, wavelength 470 nm, irradiance level 800 mW/cm$^2$) for 60s at the constant distance of 1mm. The samples were removed carefully from the mold and were polished with 4000 grit papers and alumina polishing paste.

(iii) Fourier Transform Infrared Spectroscopy (FTIR)

FTIR is a technique used to obtain an infrared spectrum of absorption or emission of a solid, liquid, or gas. It is one of the most widely used techniques for measurement of Degree of Conversion (DC) in dental composites. It is calculated by the proportion of the remaining number of the aliphatic C═C double bonds in a cured sample relative to the total number of C═C bonds in an uncured material.

Fourier Transform Infrared Spectroscopy (FTIR) was conducted before and after curing of composites (8x2 mm) to evaluate the structural changes and degree of conversion using the FTIR with attenuated total reflection (ATR) as an accessory (Thermo Nicolet 6700, USA). A background scan was obtained prior to each set of tests using carbon black specimens. The sample was placed on the diamond window which was thoroughly cleaned with ethanol to prevent contamination of samples. The spectra were collected over the region 4000-400 cm$^{-1}$ at a resolution of 8 cm$^{-1}$ and averaging 256 scans. The data was analyzed using OMINIC software and peaks were identified and matched from software library.

(iv) Degree of Conversion (DC)

The freshly prepared un-polymerized and polymerized batch of each group of resin composite was subjected to FTIR for determination of the degree of conversion. As mentioned previously, polymerized samples were cured for 60 s on each side. After recording FTIR spectra of both un-polymerized and polymerized samples, the degree of conversion was calculated using equation 1.

$$DC \% = 100 \times [1-(R_{polymerized}/R_{un\text{-}polymerized})] \quad \text{(equation 1)}$$

Where, DC denotes degree of conversion, and R is the ratio of peak height of polymerized aliphatic relative to polymerized aromatic and un-polymerized aliphatic relative to un-polymerized aromatic groups of each sample. DC was calculated by assessing the changes in the ratio of the absorbance intensities of aliphatic C═C peak at 1638 cm$^{-1}$ and aromatic C═C peak at 1608 cm$^{-1}$ of the uncured and cured samples.

(v) Scanning Electron Microscope (SEM)

The samples for SEM were carefully polished to remove any scratches and to obtain a smooth and shiny surface for studying surface morphology. The surface morphology and size of fibrous filler distribution of the composite samples were examined using a Scanning Electron Microscope (TESCAN VEGA-3 LMU, CZECK REPUBLIC). Samples were gold coated in gold SPUTTER COATER (QUORUM). Images were taken at an accelerated voltage of 20 kV.

(vi) Hardness Testing

Hardness is resistance of a material to indentation/wear and abrasion. Micro-indentation has been used to evaluate the surface oral hard tissues as well as polymeric materials. For measuring Vicker's micro-hardness, total six cylindrical specimens (8 mm in diameter, 4 mm in depth) of each group were fabricated. According to ASTM E384-11e1 [ASTM E384-11e1, Standard Test Method for Knoop and Vicker's Hardness of Materials, ASTM International, West Conshohocken, Pa., 2011, www.astm.org, incorporated herein by reference in its entirety], Vicker's hardness was measured by applying 200 gf load for 10 s by Vicker's hardness indentor (MicroMet 6040, Buehler, Germany). Three indentations were made on each specimen; the mean values of all three indentations were calculated. Experimental resin composites were compared with commercial composites.

(vii) Push-Out Bond Strength

Freshly extracted ninety bovine mandibular incisors were collected. As per ISO/TS 11405:2015, the teeth were thoroughly washed in running water and all blood and adherent tissue was removed using a stainless steel scalpel blade. In order to prevent any undesirable changes in angulation, teeth were vertically mounted in plaster. Buccal and lingual enamel was removed to expose dentin. After the exposure of dentin, cylindrical cavities of uniform size (3.5 mm in depth and 4mm in diameter) were drilled into each tooth using a straight fissure carbide bur. After cavity preparation, restoration of the prepared cavities was performed.

Figure 7:
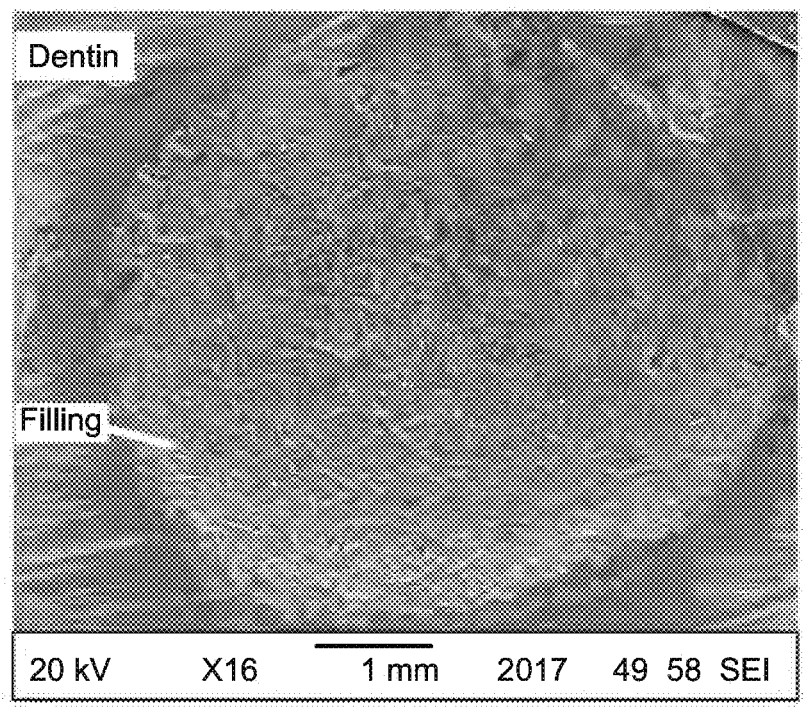
FIG. 7 is a SEM image showing a currently disclosed biomedical restoration filling in a dentin.

Each sample was etched using 37% phosphoric acid (Ivoclar Vivadent AG) for 15 s, followed by rinsing for 20 s. Adhesive resin (Scotchbond Universal, 3M ESPE, USA) was applied subsequently. The adhesive resin was cured for 10 s according to the manufacturers recommendation using a LED curing light (model LY-C240A Foshan Liang Ya Dental Equipment Co., Ltd.). After the curing of the adhesive resin, the teeth were restored with experimental and commercial resin composites. FIG. 7 is an SEM image of a tooth sample filled by the experimental composite.

After restoring the cavities, each sample was mounted in self-cure Poly methyl methacrylate (PMMA) using customized Teflon molds of 24 mm×24 mm precisely. The bond strength was obtained at three different series i.e. 1 day, 30 days, 90 days, and 180 days, respectively. Samples were stored in artificial saliva (pH 6.9) at 37° C. before being subjected to push out test.

Due to the size and sensitivity of the samples, customized stainless steel jig and an extrusion device/sample holder of carbon steel were fabricated. Each specimen was mounted onto the extrusion device and was then subjected to push out test in UTM (SHIMADZU AG-X plus Series) with the cross head speed of 1 mm min$^{-1}$. Upon completion of the push out test on each specimens, careful visualization and characterization of failure modes as adhesive, cohesive and/or mixed in the upright metallurgical microscope (OPTIKA B-1000 MET) was performed. The fractured surfaced were analyzed with SEM (Tescan Vega 3, Lmu, Czech Republic) and EDS analysis (Tescan Vega 3, Lmu, Czech Republic).

EXAMPLE 5

Figure 8:
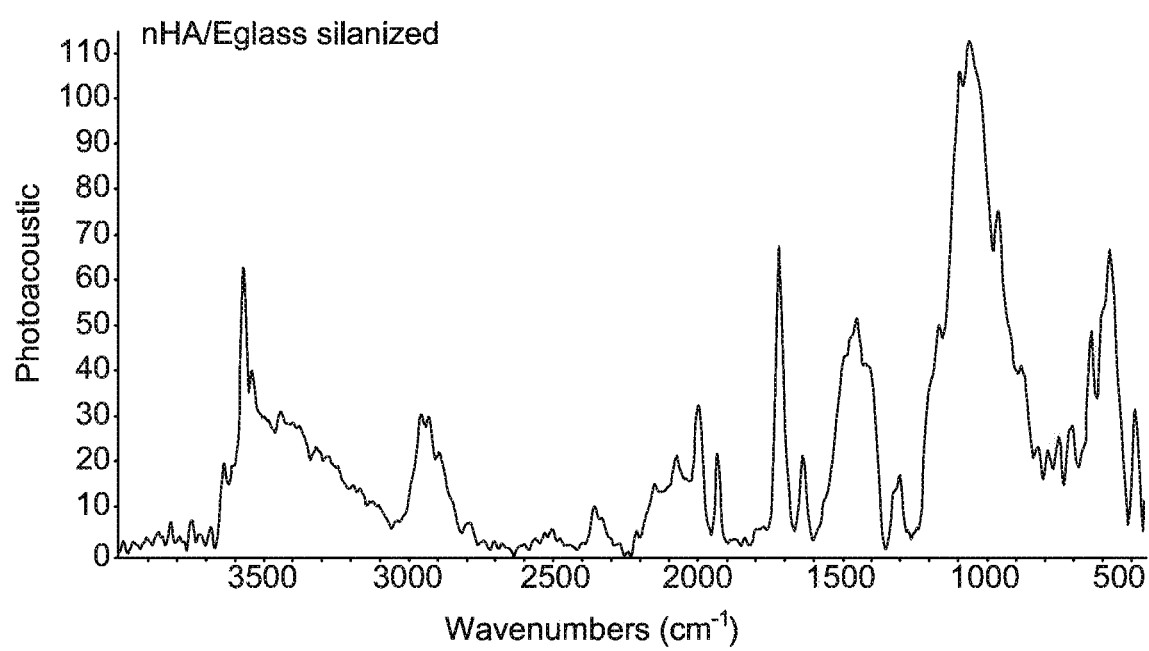
FIG. 8 is a FTIR spectrum of a fibrous filler prepared by silanizing the fibrous material nHA/E50.

Results Related to nHA/Eglass Based Dental Resin Composites
(i) Silanization of nHA/Eglass FIG. 8 showed the characteristic O—H stretching peak at 3570 cm$^{-1}$ and asymmetric and symmetric stretching peaks of C—H were observed at 2957 cm$^{-1}$ and 2831cm$^{-1}$, respectively. The characteristic peak of C=O was found at 1725 cm$^{-1}$. The carbonate absorption between 1350-1450 cm$^{-1}$ and a small peak at 1632 cm$^{-1}$ was attributed to isomeric group, Si—CH=CH—CH. A strong band (along with peaks) appeared between 3500-3300 cm$^{-1}$ was attributed to Si—C≡C and a weak peak appeared at 2040 cm$^{-1}$ corresponded to C≡C. Along with carbonate peak at 1450 cm$^{-1}$, it was noted that Si—phenyl peak also appeared in the same region. Similarly, siloxane (Si—O—Si) peaks appeared in the region 1130-1000 cm$^{-1}$, but this region may be assigned to strong phosphate group. The Si—CH$_3$ group appeared at 875 cm$^{-1}$.

(ii) Synthesis of nHA/E-Glass Based Restorations

Figure 9A:
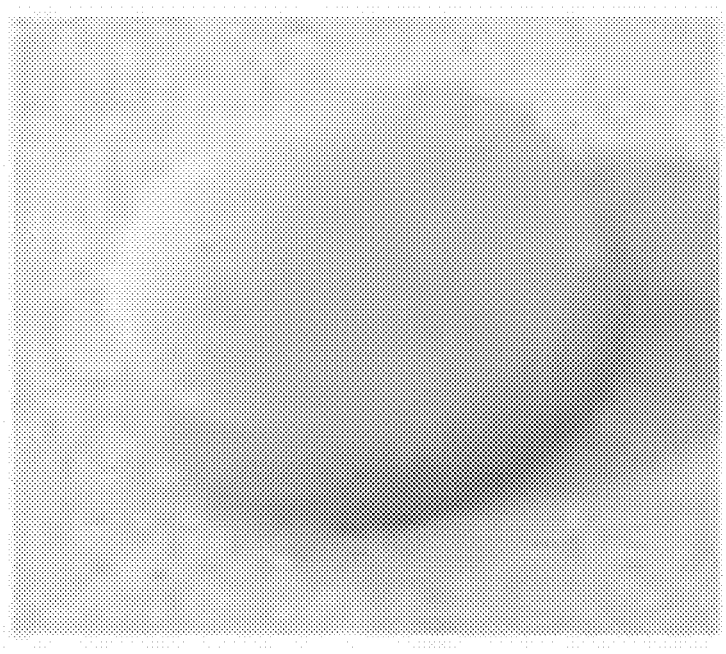
FIG. 9A is a picture of biomedical restoration of a cured resin composite containing about 60 wt % of the polymerizable monomer and about 40 wt % of a fibrous filler, each relative to a total weight of the resin composite (Exp-RBC 40).
Figure 9B:
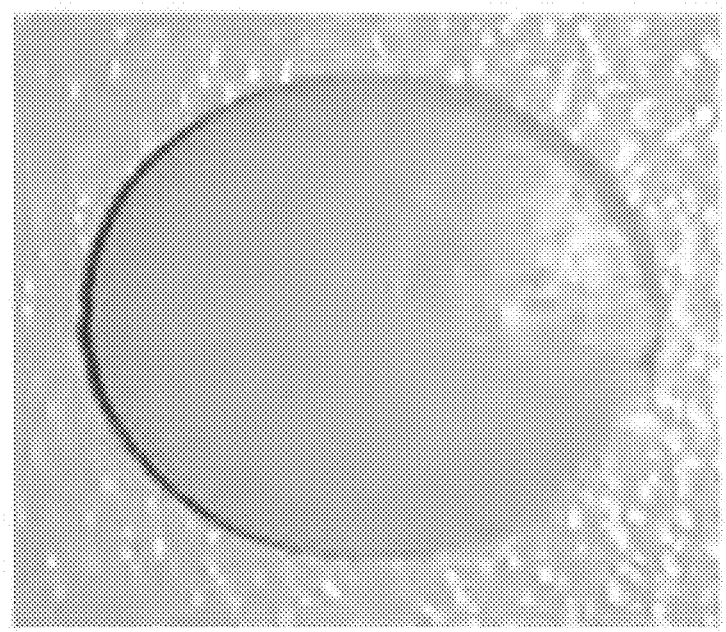
FIG. 9B is a picture of biomedical restoration of a cured resin composite containing about 40 wt % of the polymerizable monomer and about 60 wt % of a fibrous filler, each relative to a total weight of the resin composite (Exp-RBC 60).

The cured and polished forms of Exp-RBC composite discs are shown in FIGS. 9A and B. The surfaces of the restorations were shiny and smooth. However, color variations were noticed due to different compositions.

(iii) Fourier Transform Infrared Spectroscopy (FTIR)

Figure 10:
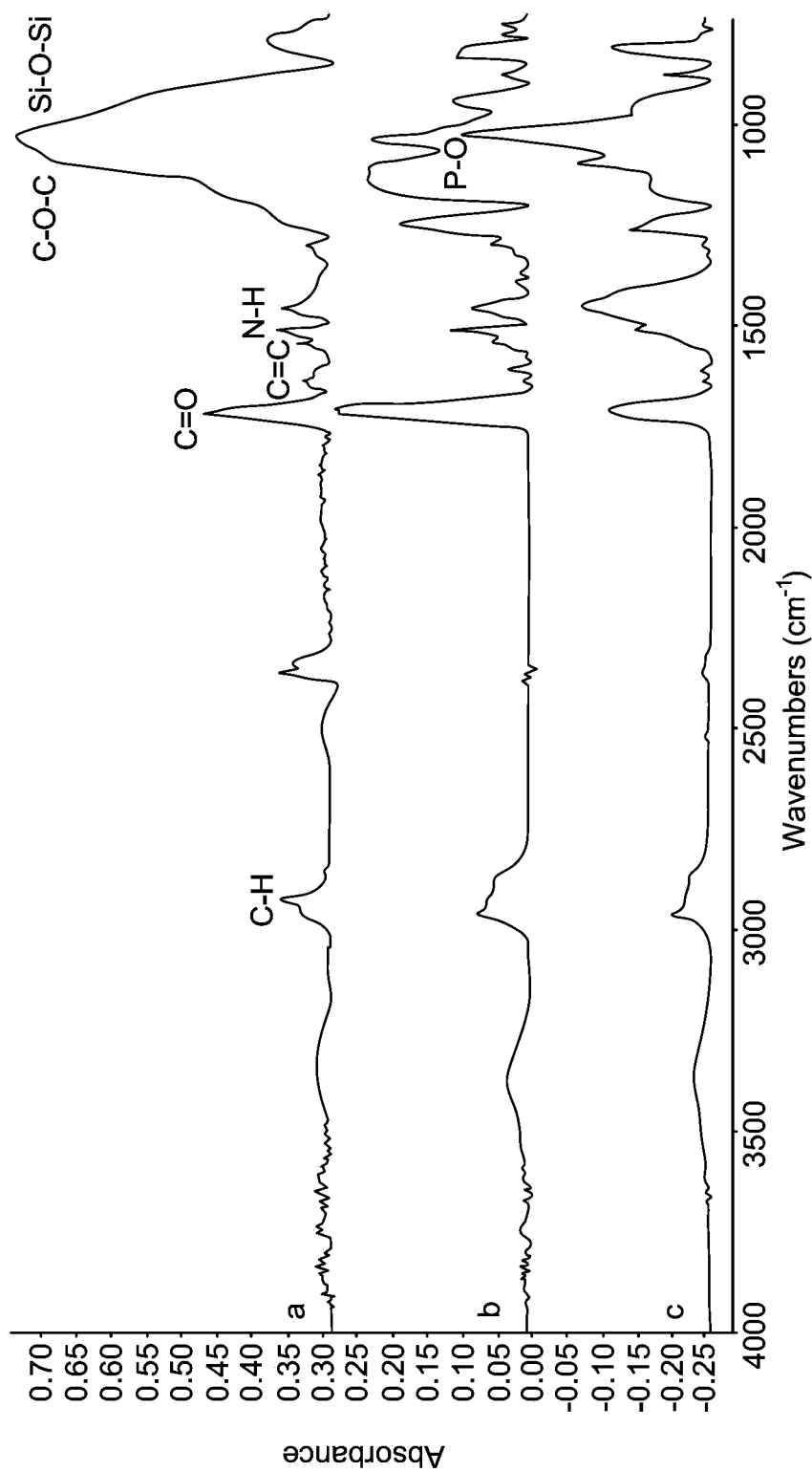
FIG. 10 is an overlay of FTIR spectra of cured forms of (a) a commercial composite (Filtek Z350, 3M ESPE), (b) a composite containing the polymerizable monomer only (CT-UF), and (c) the presently disclosed resin composite (Exp-RBC), respectively.

The FTIR spectrum for the commercial composite (Filtek Z350, 3M ESPE) and experimental dental composite materials correlates well with previsouly reported studies [Khan A, Ahmed Z, Edirisinghe M, Wong F, Rehman I. Preparation and characterization of a novel bioactive restorative composite based on covalently coupled polyurethane-nanohydroxyapatite fibres. Acta Biomaterialia 2008;4:1275-87; Lung C Y K, Sarfraz Z, Habib A, Khan AS, Matinlinna J P. Effect of silanization of hydroxyapatite fillers on physical and mechanical properties of a bis-GMA based resin composite. Journal of the mechanical behavior of biomedical materials 2016;54:283-94; and Khan A S, Khalid H, Sarfraz Z, Khan M, Iqbal J, Muhammad N, et al. Vibrational spectroscopy of selective dental restorative materials. Applied Spectroscopy Reviews 2016:1-34, each incorporated herein by reference in their entirety]. Representative spectra of control and experimental resin composite materials showing characteristic peaks of dimethacrylate resins may be found in FIG. 10. CT-UF has a highest DC of 82% after polymerization, which was followed by 71% DC of Exp-RBC 40, 65% DC of Exp-RBC 50, 56% DC of Exp-RBC 60, and 50% DC of the commercial composite.

Figure 11:
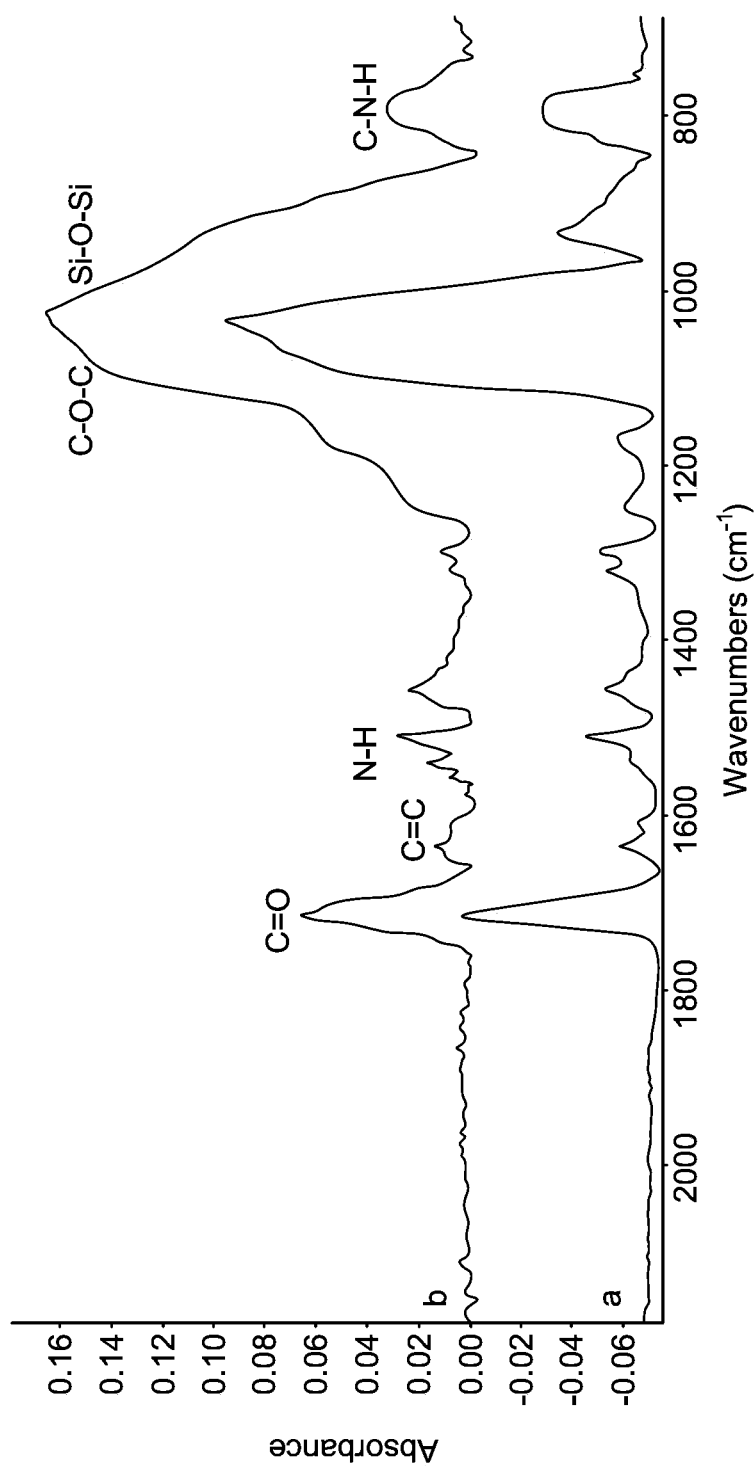
FIG. 11 is an overlay of FTIR spectra of the commercial composite (a) before and (b) after curing, respectively.

FTIR spectra having characteristic peaks of the commercial composite before and after curing is shown in FIG. 11. The peak at 1711 cm$^{-1}$ was assigned to carbonyl stretch in the resin polymer. At 1636 cm$^{-1}$ C=C stretching vibration of the methacrylate group was visible, while C=C in an aromatic benzene ring presented in resin matrix was observed at 1606 cm$^{-1}$. The N-H deformation stretching of urethane dimethacrylate (UDMA) appeared at 1509 cm$^{-1}$. A weak peak at 1034 cm$^{-1}$ showed asymmetric stretching of C—O—C and stretching vibration of Si—O due to silicates in the constituents [Younas B, Khan A S, Muzaffar D, Hussain I, Chaudhry A A, Rehman I U. In situ reaction kinetic analysis of dental restorative materials. The European Physical Journal Applied Physics 2013;64:30701, incorporated herein by reference in its entirety]. After curing, another IR spectrum was obtained where a significant decrease in peak intensities or peak heights was observed. The intensity of the peak at 1711 cm$^{-1}$ corresponding to free carbonyl group decreased, which suggested the consumption of free carbonyl groups during polymerization. The decreased intensities of peaks at 1636 cm$^{-1}$ and 1606 cm$^{-1}$, each corresponding to C=C group of the methacrylate group and aromatic ring of resins, were resulted from the conversion of C=C to C—C (degree of conversion). The peak intensity of N—H deformation of urethane dimethacrylate at 1509 cm$^{-1}$ was also lower after curing.

Figure 12:
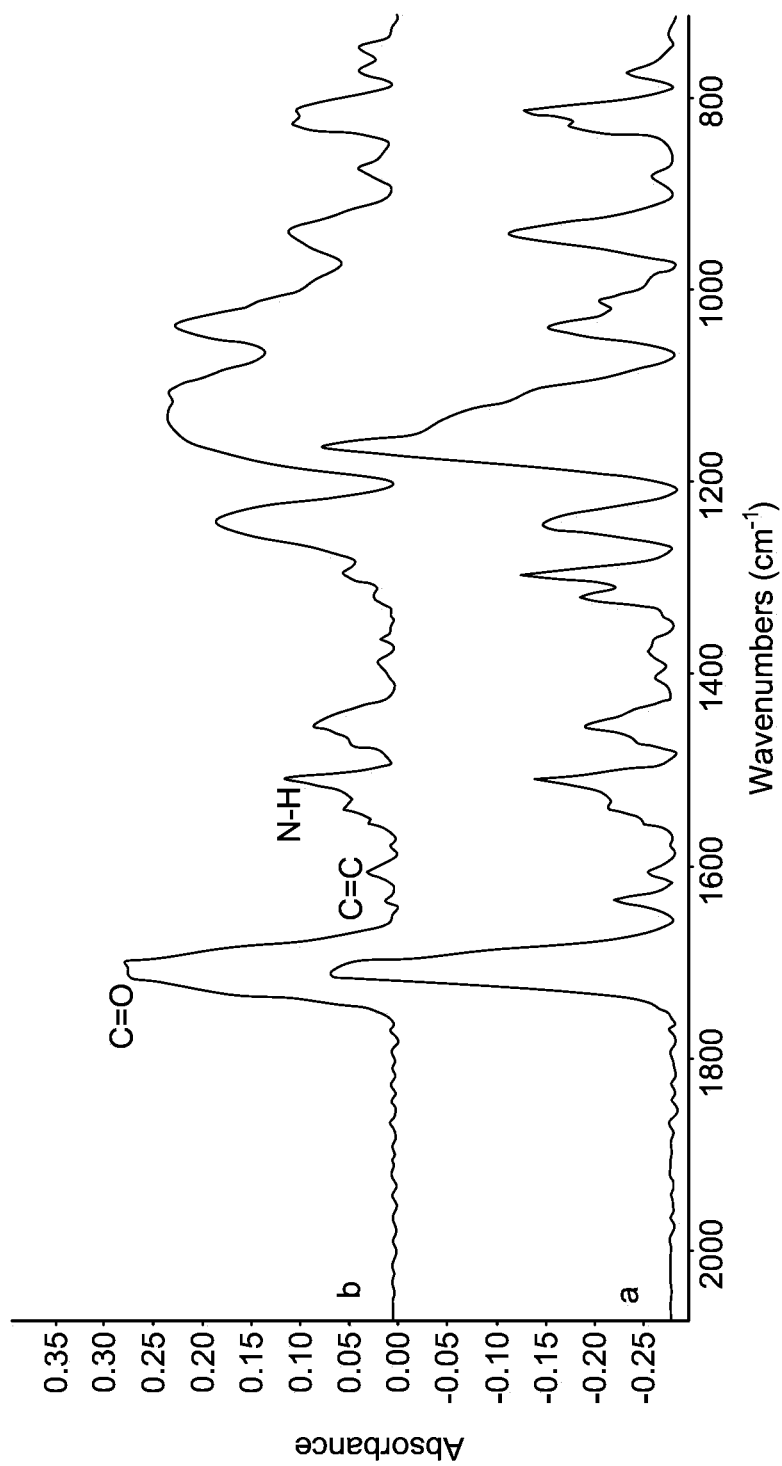
FIG. 12 is an overlay of FTIR spectra of the composite CT-UF (a) before and (b) after curing, respectively.

FTIR spectra having characteristic peaks of CT-UF before and after curing are shown in FIG. 12. The observed peaks of resin matrix were almost similar to those of the commercial composite. The peak at 1711 cm$^{-1}$ was assigned to carbonyl group in the resin polymer. The peak area around 1636 cm$^{-1}$ was attributed to methacrylate group. C=C in an aromatic ring of benzene presented in resin matrix was seen at 1606 cm$^{-1}$. N—H deformation stretching of urethane group appeared at 1509 cm$^{-1}$. After curing, the peak intensity at 1711 cm$^{-1}$ corresponding to free carbonyl group decreased. Similarly, decreasing intensities were observed for peaks around 1636 cm$^{-1}$ and 1606 cm$^{-1}$ which indicated the consumption of aliphatic and aromatic groups during polymerization.

Figure 13:
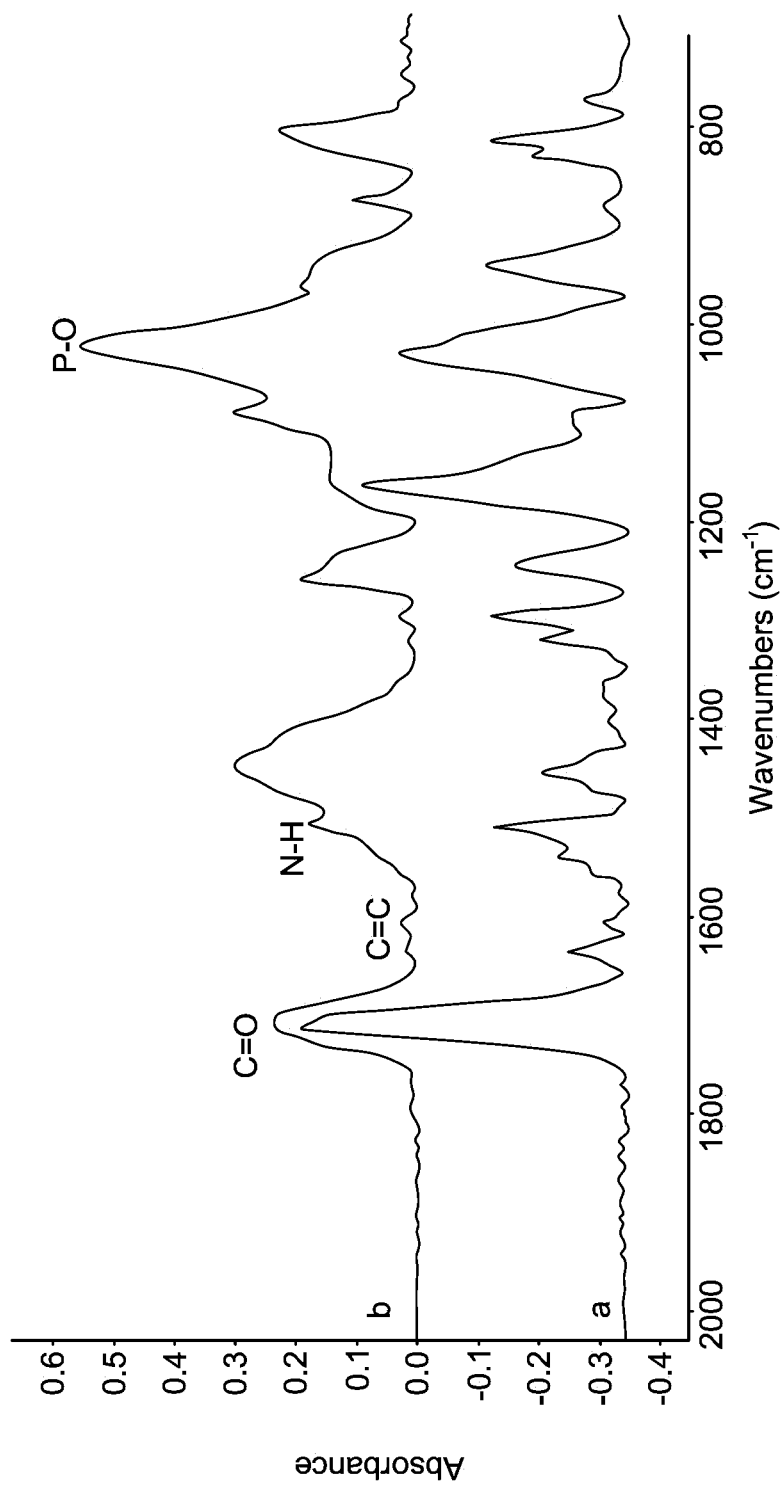
FIG. 13 is an overlay of FTIR spectra of the resin composite Exp-RBC 40 (a) before and (b) after curing, respectively.
Figure 14:
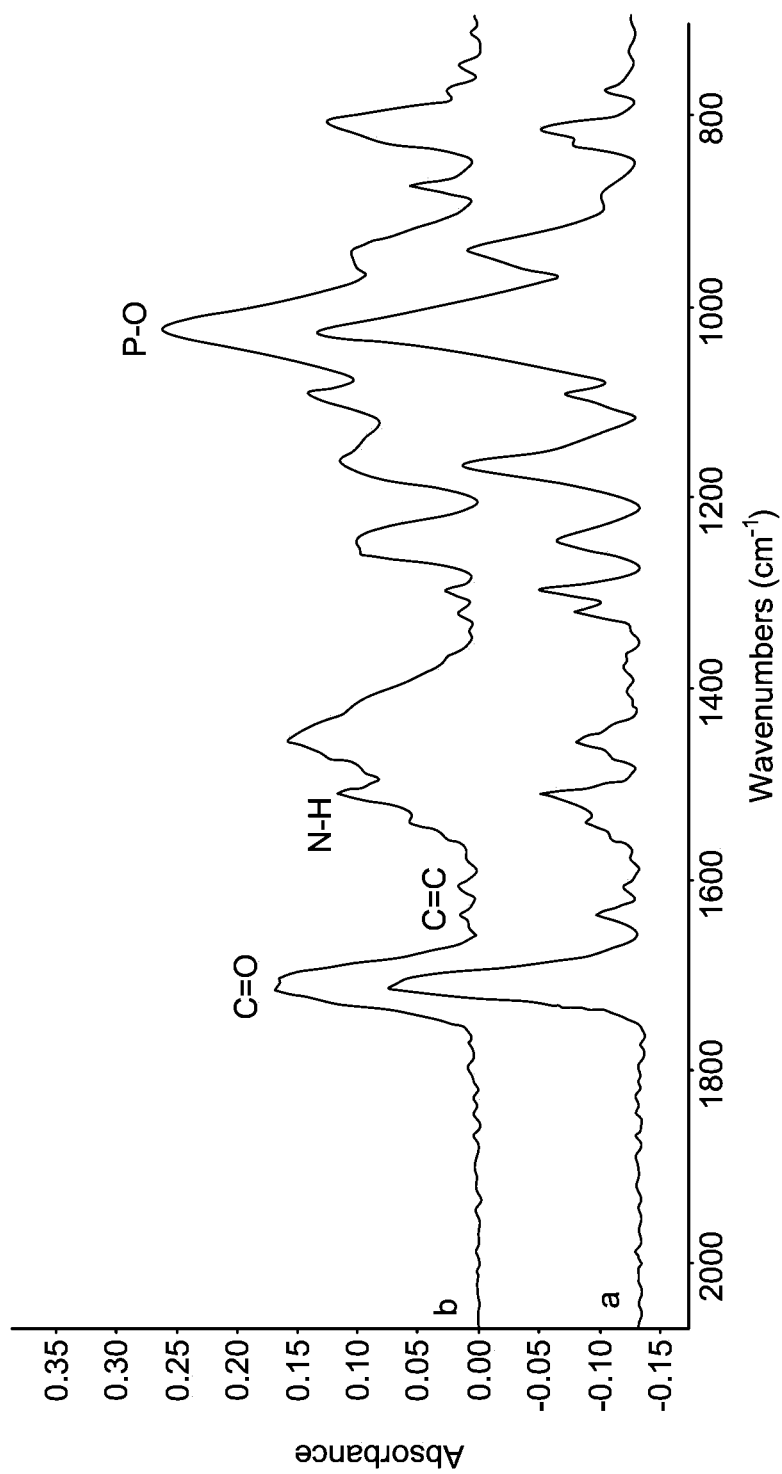
FIG. 14 is an overlay of FTIR spectra of a resin composite containing about 50 wt % of the polymerizable monomer and about 50 wt % of a fibrous filler, each relative to a total weight of the resin composite (Exp-RBC 50) before and after curing, respectively.
Figure 15:
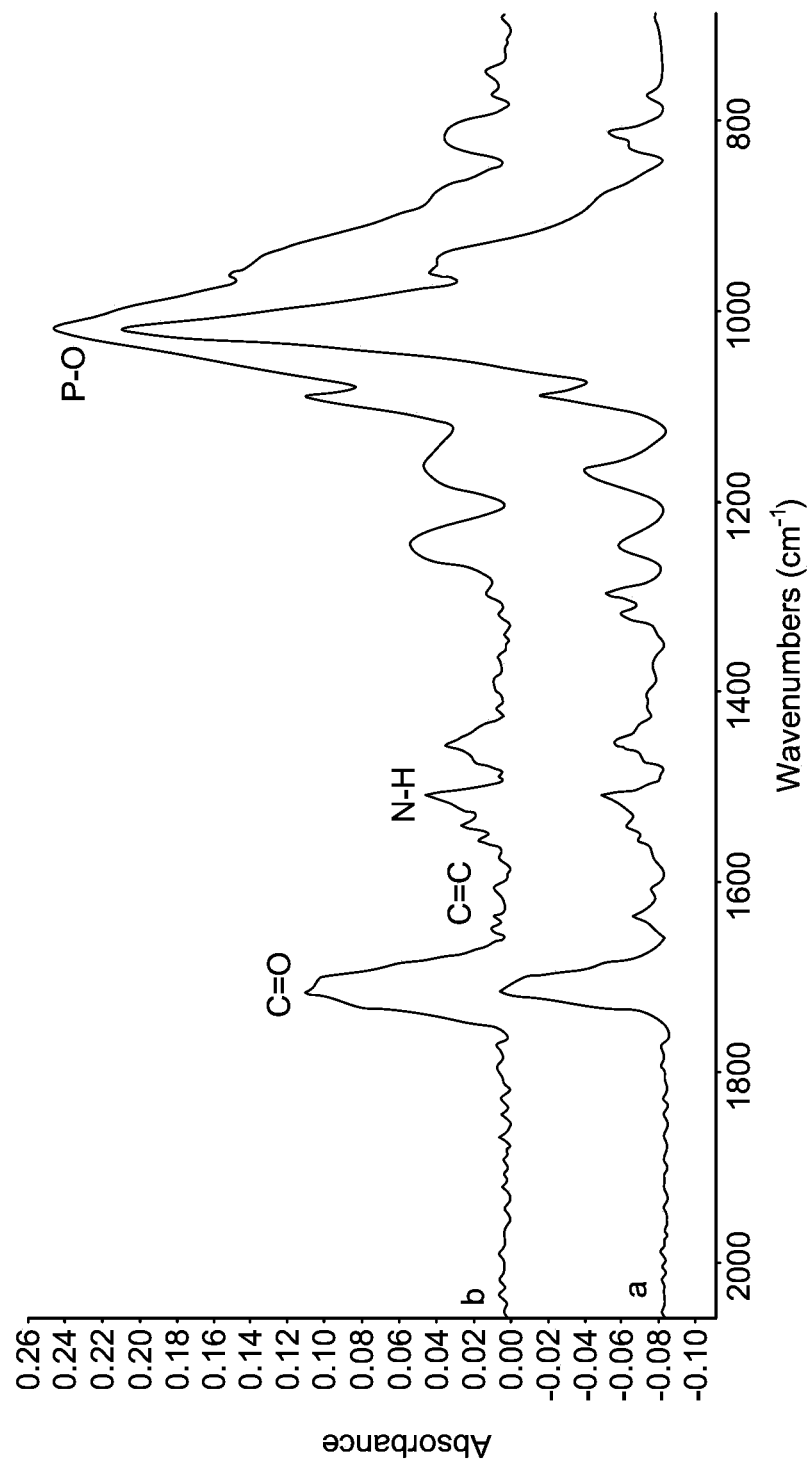
FIG. 15 is an overlay of FTIR spectra of the resin composite Exp-RBC 60 before and after curing, respectively.
Figure 16A:
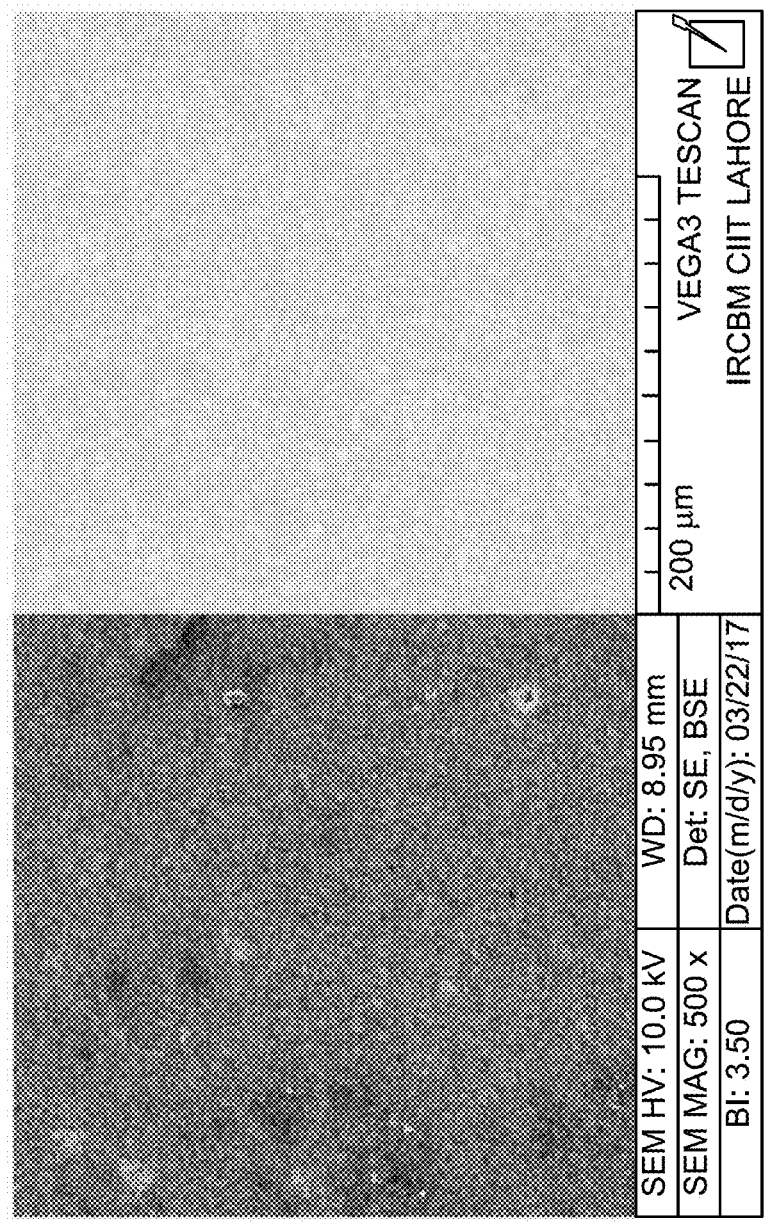
FIG. 16A shows SEM images of a cured form of the commercial composite.
Figure 16B:
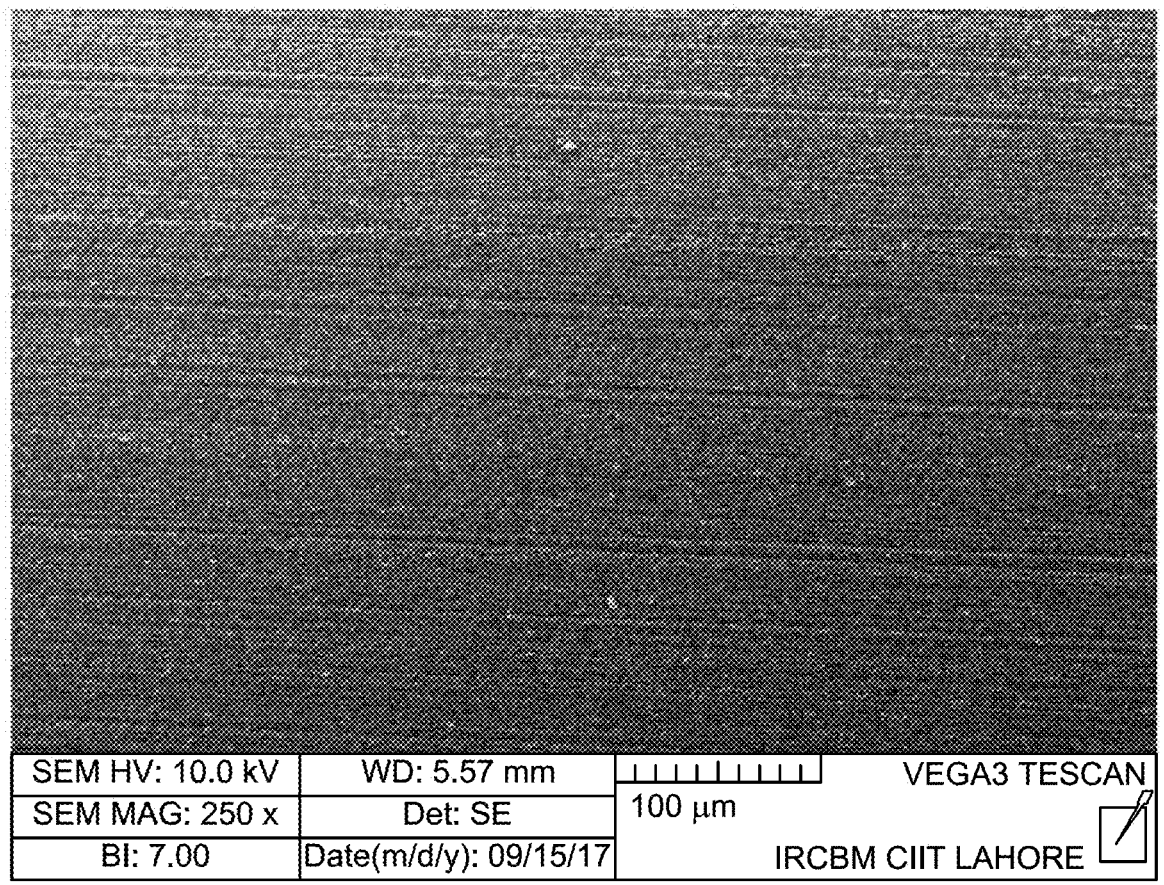
FIG. 16B is a SEM image of a cured form of the composite CT-UF.
Figure 16C:
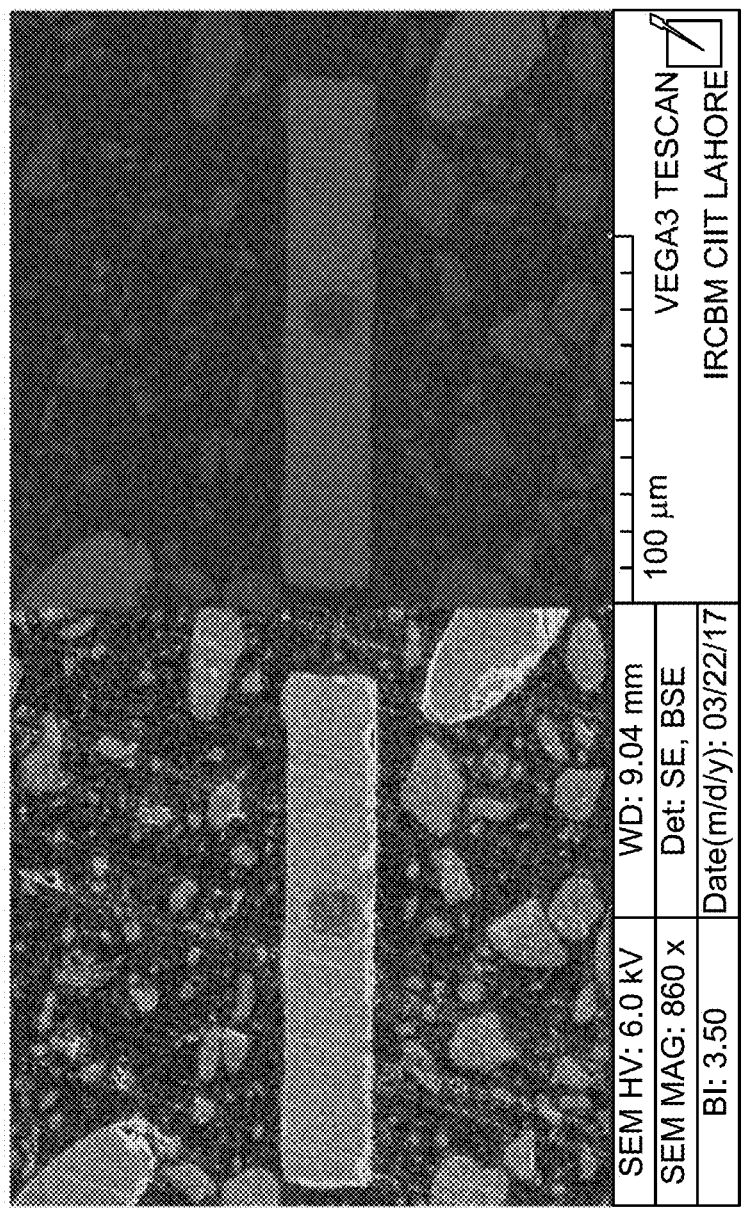
FIG. 16C shows SEM images of a cured form of the resin composite Exp-RBC 40.
Figure 16D:
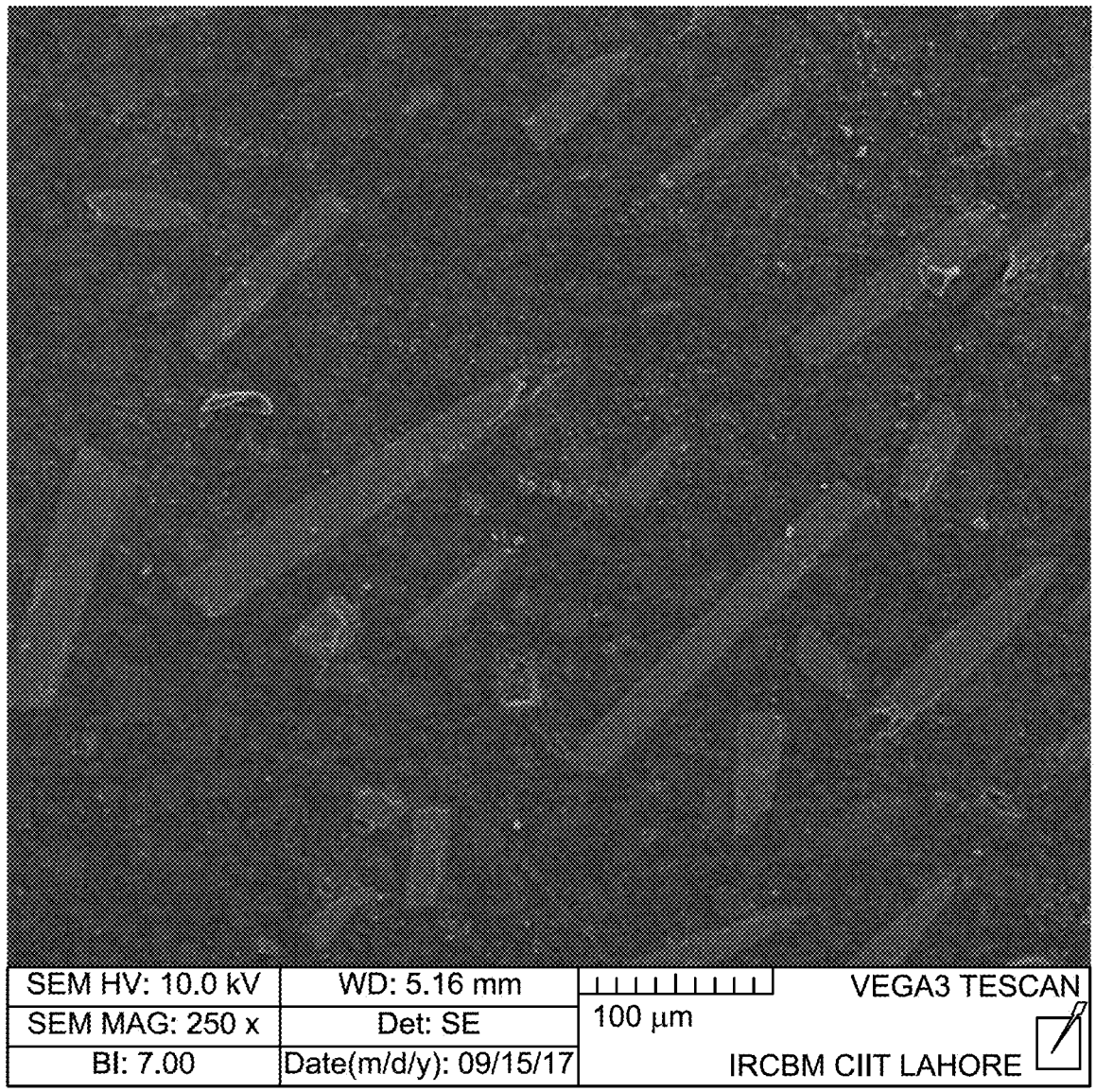
FIG. 16D is a SEM image of a cured form of the resin composite Exp-RBC 50.
Figure 16E:
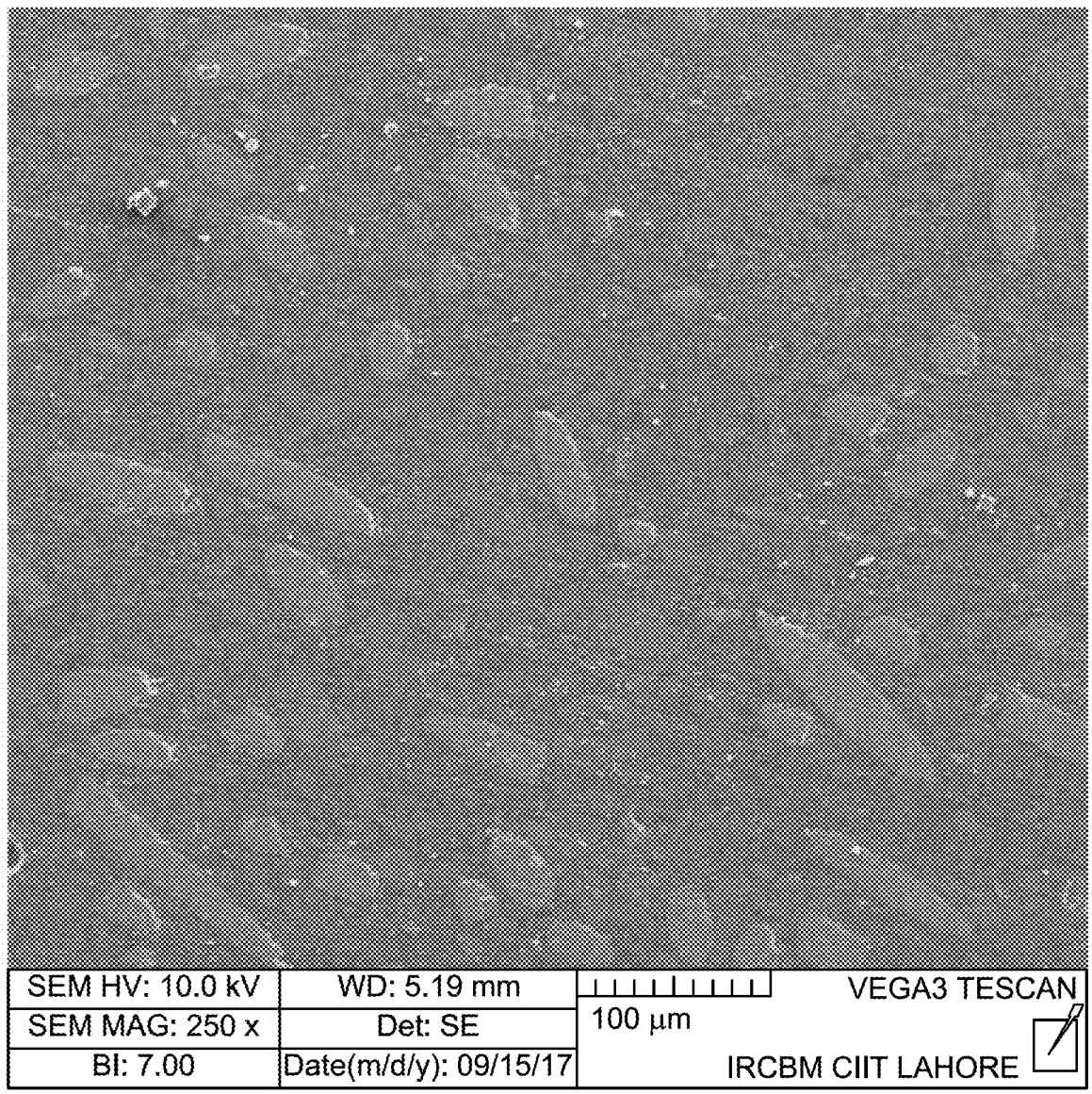
FIG. 16E is a SEM image of a cured form of the resin composite Exp-RBC 60.

Similar FTIR spectra (FIGS. 13-15) were observed for all restorations based on the resin composites disclosed herein. The primary differences amongst these spectra were peak height ratios of various functional groups. Before curing, the C=O group was observed at 1711 cm$^{-1}$ which was present in all resin monomers. The C=C methacrylate group vibration was observed at 1636 cm$^{-1}$ while 1606 cm$^{-1}$ was assigned to C=C peak in an aromatic benzene ring present in resin matrix. The N—H deformation stretching of urethane monomer was observed at 1509 cm$^{-1}$. There were characteristic phosphate vibrations of phosphate group present in all n-HA/E glass based restorations at around 1000 cm$^{-1}$. After curing, the peak intensity at 1711 cm$^{-1}$ corresponding to free carbonyl group decreased. Similarly, decreasing intensities were observed for peaks around 1636 and 1606 cm$^{-1}$ which suggested the consumption of these groups during polymerization.

(iv) Scanning Electron Microscope

The comparative SEM images of CT-UF, Exp-RBC 40, Exp-RBC 50 and Exp-RBC 60 depicting morphology and filler size are shown in FIGS. 16 A-E. These images showed that the sample surfaces were smooth and free of cracks.

It was observed that silica particles in the commercial composite had an average size around 5-20 nm and clusters of 0.6-1.4 μm in size. In the currently disclosed restorations, it was observed that E-glass fibers were present haphazardly. Most E-glass fibers were longitudinal in direction while some were oriented transversely. The average size of glass fibers was 150-220 μm. Particles of nHA were globular in shape with a diameter of around 35-150 nm. Homogeneous distribution of fillers could be seen in a continuous organic phase. CT-UF was purely resin based, thus no filler could be seen in SEM images.

(v) Hardness Testing

The comparative mean microhardness values of restorations of cured composite groups are shown in Table 6. The observed hardness was 61.89±3.75 for Exp-RBC 60, 58.84±1.07 for the commercial composite, 56.78±1.2 for Exp-RBC 50, 52.06±3.92 for Exp-RBC 40, and 34.95±0.69 for CT-UF. One way ANOVA revealed that there is a statistically significant difference between all groups with p value <0.05.

TABLE 6

Vickers microhardness values of restorations of corresponding cured resin composites
Vickers hardness results

| Groups | Mean ± SD values | P value |
|---|---|---|
| Commercial Composite | 58.84 ± 1.07 | |
| CT-UF | 34.95 ± 0.69 | |
| Exp-RBC 40 | 52.06 ± 3.92 | <0.05 |
| Exp-RBC 50 | 56.78 ± 1.2 | |
| Exp group D | 61.89 ± 3.75 | |

(vi) Push-Out Bond Strength

The mean push out bond strength values of each restoration of cured composite along with the standard deviations and percentage coefficient of variation collected at each time interval are tabulated in Table 7. Unfilled resin (CT-UF) showed low bond strength and statistically significant difference (p<0.05) was found compared to other groups. On day 1, 30 and 90, no statistical difference (p >0.05) was found among experimental composites (Exp-RBC 40, Exp-RBC 50, and Exp RBC 60) and commercial composite, however a statistical difference (p<0.05) was found on day 180.

Among all the experimental composites, Exp-RBC 60 had the highest bond strength to dentin. However, the differences found were not statistically significant (p >0.05). A significant increase in the bond strength of Exp-RBC 60 was observed after 180 days as compared to the bond strength tested on day 1, 30 and 90 days (p<0.05). Similarly a significant increase in the bond strength of Exp-RBC 50 was observed as compared to day 1, 30 and 90 (p<0.05). Exp-RBC 40 also yielded a greater push out bond strength to dentin as compared to day 1, 30 and 90 but the difference was statistically insignificant (p >0.05). Push out bond strength of Exp-RBC 60 and Exp-RBC 50 to dentin was significantly higher than the commercial composite (p<0.05).

TABLE 7

Push-out bond strength values of commercial and experimental resin composites

| Composites | Days | | | |
|---|---|---|---|---|
| | 1 | 30 | 90 | 180 |
| Exp-RBC 60 | 22.0 ± 5 (23%) | 20.9 ± 3.9 (19%) | 19.6 ± 4.8 (24%) | 49.9 ± 10.9 (22%) |
| Exp-RBC 50 | 21.5 ± 5 (23%) | 17.1 ± 5 (29%) | 17.1 ± 4.3 (25%) | 35.40 ± 8.1 (23%) |
| Exp-RBC 40 | 18.6 ± 3.6 (19%) | 16.2 ± 4.3 (25%) | 16.6 ± 4.8 (29%) | 26.57 ± 7.1 (27%) |
| CT-UF | 4.4 ± 1.7 (39%) | 4.4 ± 1.8 (41%) | 5.7 ± 2.4 (42%) | 5.59 ± 1.4 (25%) |
| Commercial | 24.9 ± 5.5 (22%) | 22 ± 5 (23%) | 22.0 ± 3.5 (16%) | 23.82 ± 6.6 (28%) |

Figure 17B:
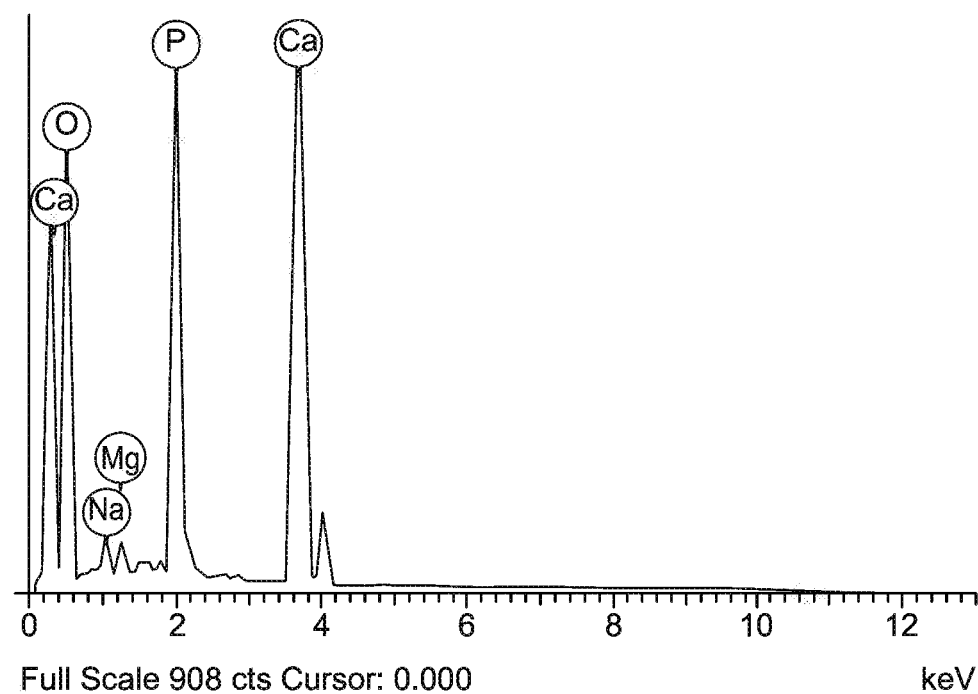
FIG. 17B is an energy dispersive X-ray spectroscopy (EDX, EDS) spectrum of the interface in FIG. 17A.
Figure 17C:
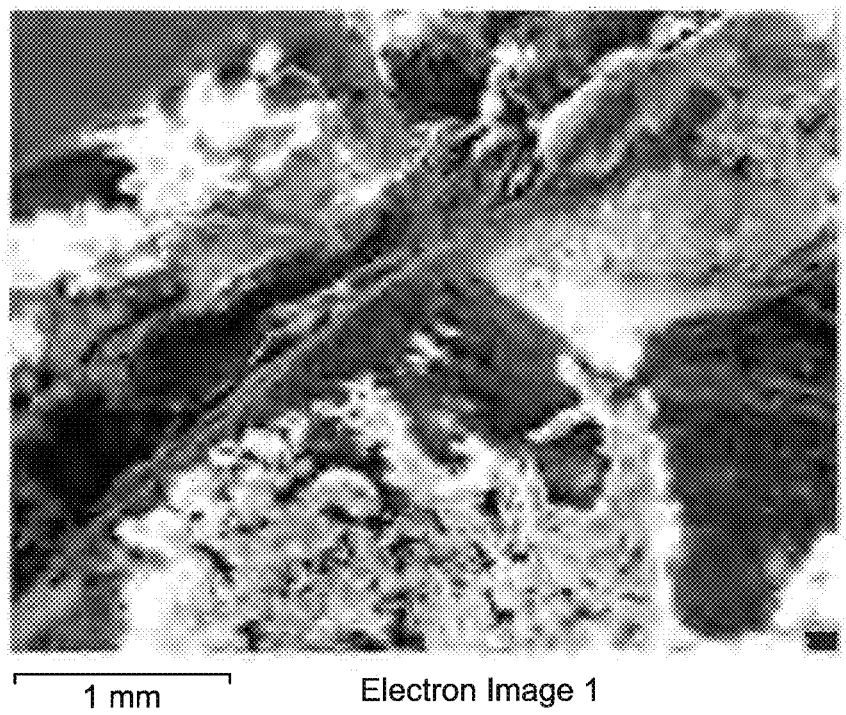
FIG. 17C is a SEM image of the interface at a different location appeared after push out test on the resin composite (Exp-RBC 60) to dentin.
Figure 17D:
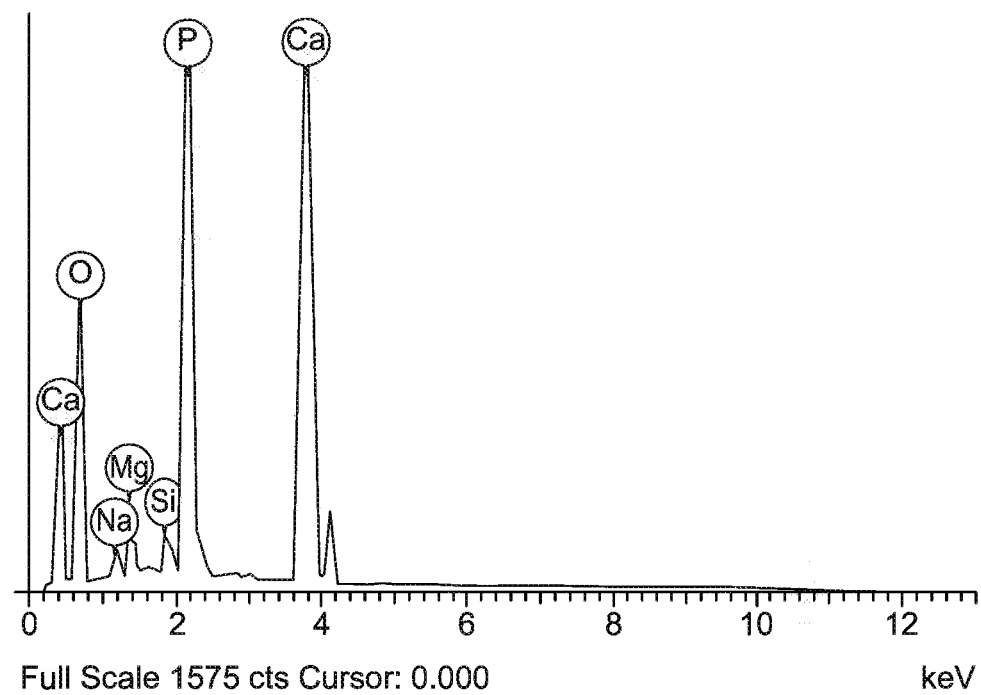
FIG. 17D is an energy dispersive X-ray spectroscopy (EDX, EDS) spectrum of the interface in FIG. 17C, showing the Si peak that confirms the release of ions from the resin composite.
Figure 17E:
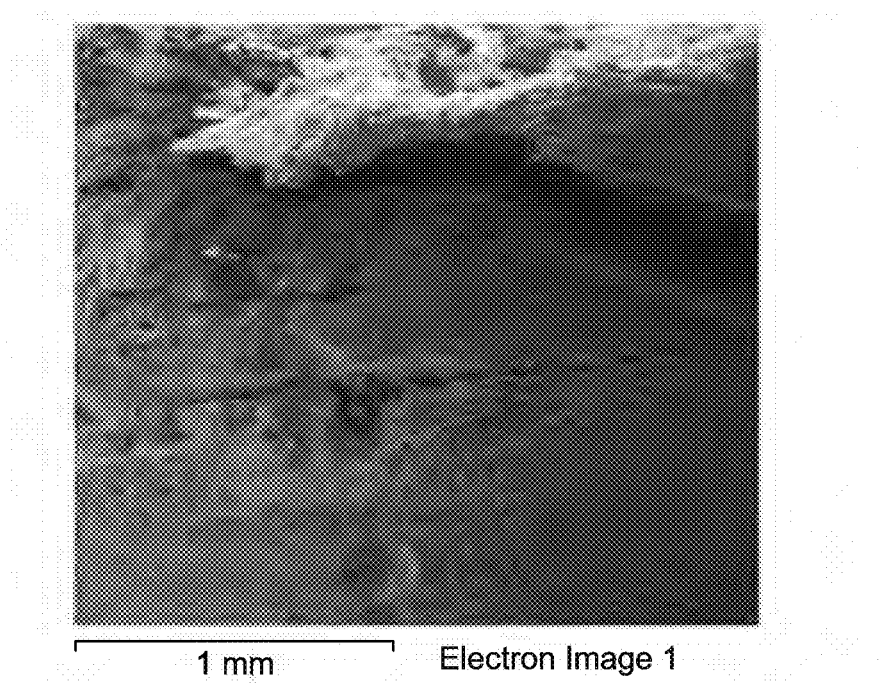
FIG. 17E is a SEM image of the outer surface of the resin composite (Exp-RBC 60) after push out test to dentin.
Figure 17F:
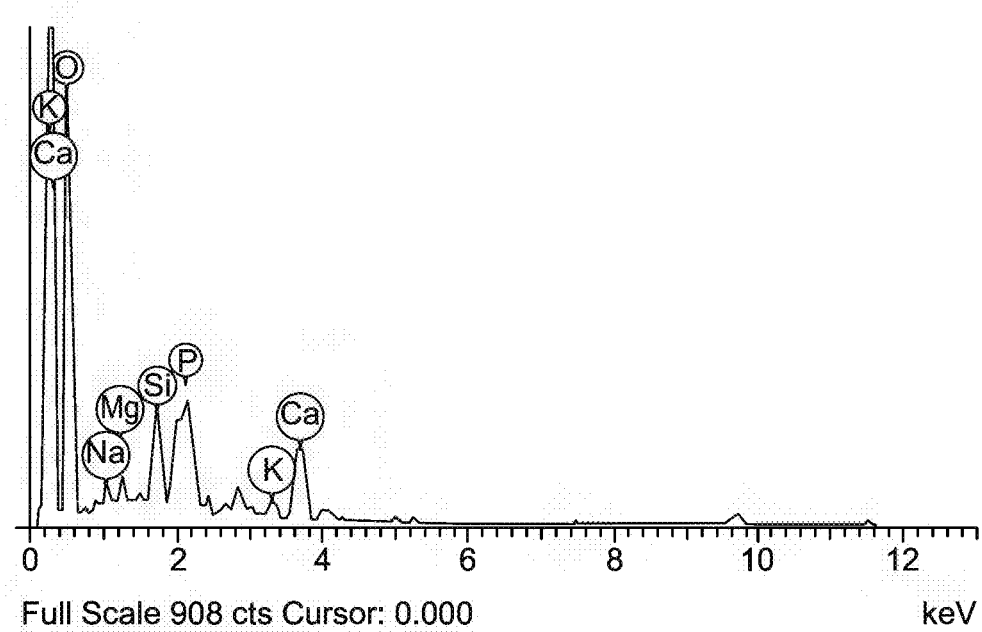
FIG. 17F is an energy dispersive X-ray spectroscopy (EDX, EDS) spectrum of the surface in FIG. 17E, showing the presence of Ca, P, and Si peaks.
Figure 17G:
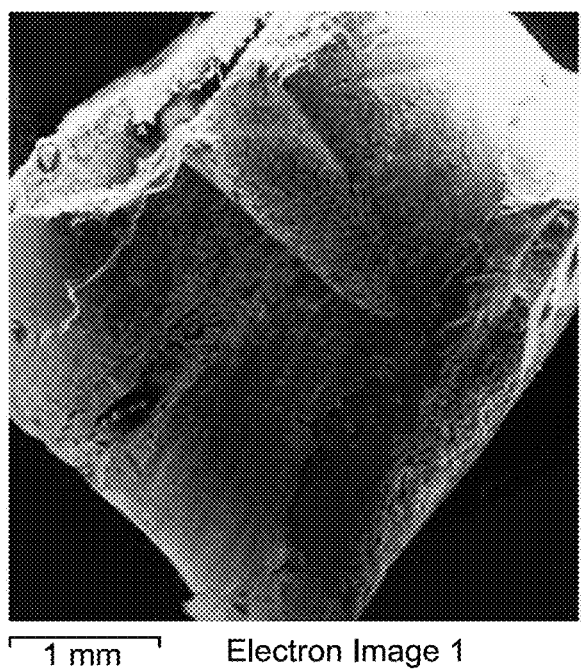
FIG. 17G is a SEM image of the outer and inner structures taken after push out test on the composite (Exp-RBC 60) after immersion in deionized water.
Figure 17H:
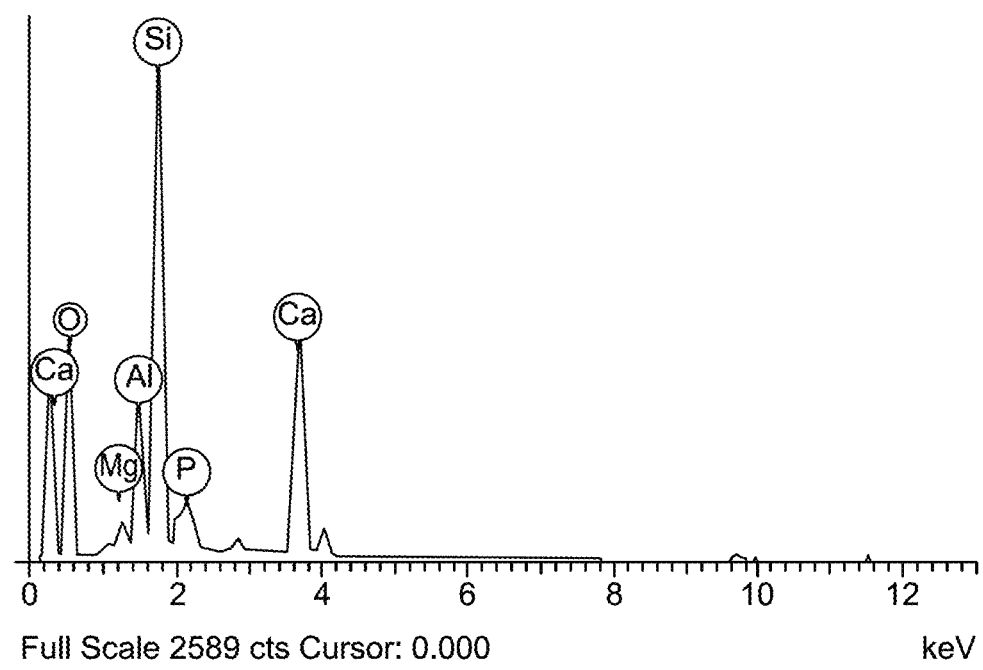
FIG. 17H is an energy dispersive X-ray spectroscopy (EDX, EDS) spectrum of the composite in FIG. 17G, showing the presence of Ca, P, and Si peaks.
Figure 17I:
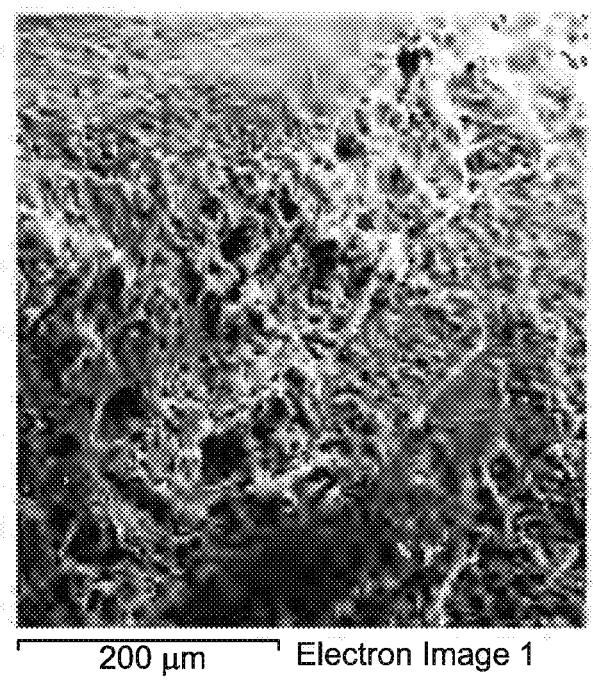
FIG. 17I is a SEM image of the interface appeared after push out test on the experimental composite (Exp-RBC 40) to dentin.
Figure 17J:
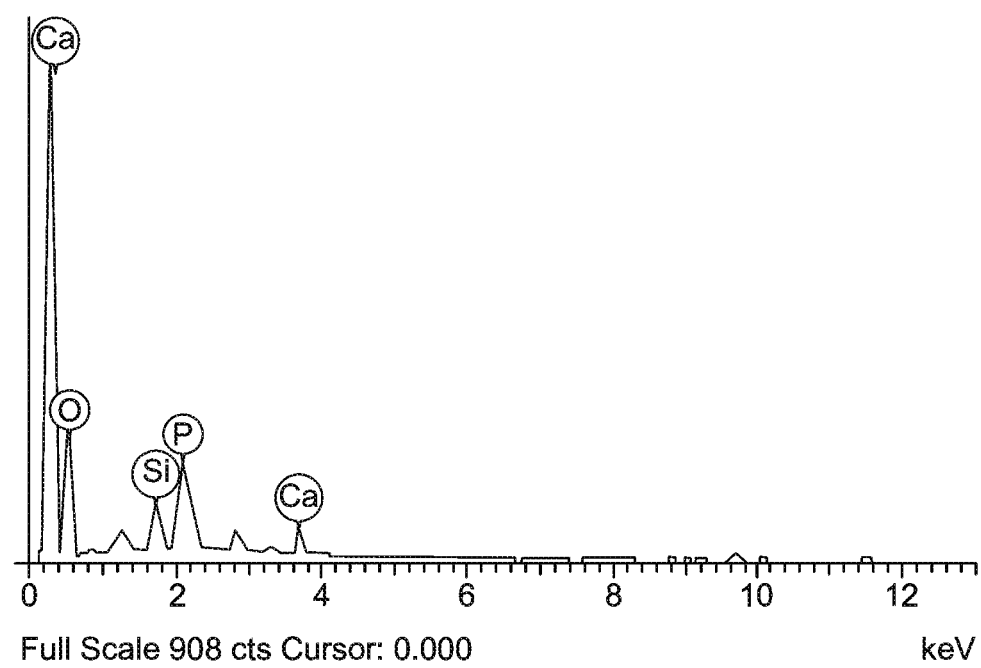
FIG. 17J is an energy dispersive X-ray spectroscopy (EDX, EDS) spectrum of the composite in FIG. 17I.

EDS analysis of the fractured interfaces revealed calcium and phosphorus peaks in the samples based on the experimental resin composites, indicating a high remineralization potential of these experimental composites (FIGS. 17B, D and F). The amount of calcium and phosphorus ion precipitation at the interface increased with increasing amount of nano HA in the experimental composites. Exp-RBC 60 containing the maximum amount of fillers (~60% by weight) had the highest percentage by weight of calcium and phosphorus at the interface.

EXAMPLE 5

Discussions Related to nHA/Eglass Based Resin Composites and Restorations

The experimental composite based on novel bioactive fibrous fillers have been successfully developed and their structural, morphological, physical and mechanical properties were evaluated.

Several structural characterizations of the composites disclosed herein are consistent with those previously reported [Khan A, Ahmed Z, Edirisinghe M, Wong F, Rehman I. Preparation and characterization of a novel bioactive restorative composite based on covalently coupled polyurethane–nanohydroxyapatite fibres. Acta Biomaterialia 2008;4:1275-87; Lung C Y K, Sarfraz Z, Habib A, Khan A S, Matinlinna J P. Effect of silanization of hydroxyapatite fillers on physical and mechanical properties of a bis-GMA based resin composite. Journal of the mechanical behavior of biomedical materials 2016;54:283-94; and Younas B, Khan A S, Muzaffar D, Hussain I, Chaudhry A A, Rehman I U. In situ reaction kinetic analysis of dental restorative materials. The European Physical Journal Applied Physics 2013;64:30701, each incorporated herein by reference in their entirety]. The characteristic peaks of all composites showed marked decrease in peak height after polymerization. This decrease in peak height could be due to consumption of functional groups. The degree of conversion showed the conversion of C=C to C—C after curing. It correlated well with the concentrations of organic matrix and inorganic material. For example, a higher concentration of organic matrix usually leads to a higher degree of conversion.

All composites showed free carbonyl stretch at 1711 $cm^{-1}$ which was consumed during polymerization. The stretching vibrations of C=C aliphatic group at 1636 $cm^{-1}$ and C=C present in aromatic benzene ring of bis-GMA at 1606 $cm^{-1}$ also showed marked decrease in height after curing, indicating the polymerization reaction of converting C=C to C—C. Similarly, the peak at 1509 $cm^{-1}$, representing the urethane linkage due to N—H deformation stretching, became prominent after curing. All experimental composites showed phosphate group peaks at around 1000-1050 $cm^{-1}$ which decreased in height and showed peak shifting to 1023-1030 $cm^{-1}$ after curing, which suggested the consumption of phosphate groups.

It is important that most of the monomers are converted into polymers during polymerization reaction to achieve long-term durability of dental composites. The physical and some mechanical properties of dental composites are directly influenced by the degree of conversion obtained during polymerization. The concentration of resin monomers had direct influence on the degree of conversion of composites. The results on commercial composite are in accordance with the previous studies, which showed the DC of Filtek Z350 ranged from 47-55%. However, shade to shade and different curing light affect the DC slightly [Froes-Salgado N R, Silva L M, Kawano Y, Francci C, Reis A, Loguercio A D. Composite pre-heating: effects on marginal adaptation, degree of conversion and mechanical properties. Dental materials, 2010;26:908-14, incorporated herein by reference in its entirety]. Previously, a study investigating DC of two nano-hybrid composites and one submicron-hybrid found DCs of 58.85% and 58.78% for nano-hybrid and 62.20% for submicron-hybrid, respectively, while the microhardness results were observed in reverse order. The results showed that an increase in filler concentration would increase the hardness but decrease DC [Marovic D, Panduric V, Tarle Z, Ristic M, Sariri K, Demoli N, et al. Degree of conversion and microhardness of dental composite resin materials. Journal of Molecular Structure 2013;1044:299-302, incorporated herein by reference in its entirety]. A large DC is desirable, although it often causes substantial polymerization shrinkage. It is revealed in the current disclosure that increasing concentration of filler contents in the resin composite would lead to enhanced micro-hardness of the restoration.

The hardness values of these experimental composites are comparable to those of commercial composites. Hardness values also depend on the concentration of fillers. Most commercial composites contain a large amount of filler at a concentration of 65-80%. In this disclosure, filler loading and the interaction between resin matrix and fillers markedly affected the surface hardness of experimental resin composites. The results showed that the surface hardness of the restoration disclosed herein increased significantly by increasing the filler loading, which was resulted from a greater hard phase in the resin matrix.

The fibers in all experimental groups were mostly oriented parallel to the direction of stress i.e. longitudinal. According to Krenchel's factor, reinforcing efficiency is the highest if fibers are arranged in the direction of stress, and reinforcing efficiency will be the lowest if fibers are placed in the direction perpendicular to the stress, which ultimately leads to transverse axis failure. Minimum length of fiber, known as critical fiber length, should be in the range of 750-900 um. Increasing the length of a fibrous filler usually makes the filler more wear resistant [Callaghan DJ, Vaziri A, Nayeb-Hashemi H. Effect of fiber volume fraction and length on the wear characteristics of glass fiber-reinforced dental composites. Dental materials, 2006;22:84-93, incorporated herein by reference in its entirety].

Silanized nHA/Eglass filler was incorporated in all experimental composites. Incorporation of silanized filler particles or fibers may improve the microhardness of the composite [Lung C Y K, Sarfraz Z, Habib A, Khan A S, Matinlinna J P. Effect of silanization of hydroxyapatite fillers on physical and mechanical properties of a bis-GMA based resin composite. Journal of the mechanical behavior of biomedical materials 2016;54:283-94; and Debnath S, Ranade R, Wunder S, McCool J, Boberick K, Baran G. Interface effects on mechanical properties of particle-reinforced composites. dental materials 2004;20:677-86, each incorporated herein by reference in their entirety]. The use of synthetic HA is important because it has hardness similar to that of human dentin [O'Brien W J. Dental materials and their selection: Quintessence Publ. Chicago; 1997; and Domingo C, Arcis R, López-Macipe A, Osorio R, Rodriguez-Clemente R, Murtra J, et al. Dental composites reinforced with hydroxyapatite: Mechanical behavior and absorption/elution characteristics. Journal of biomedical materials research 2001;56:297-305, each incorporated herein by reference in their entirety]. Previously conducted studies observed that nano-HA based dental composites had a microhardness value of about 55. Another study showed that a 65-70 VHN was achieved with 80% loading of HA in dental composites [Labella R, Braden M, Deb S. Novel hydroxyapatite-based dental composites. Biomaterials 1994; 15:1197-200, incorporated herein by reference in its entirety]. In addition, commercially available composites including Amelogen plus (Ultradent Plus) and Te-Econom plus (Ivoclar Vivadent) each had a reported VHN of 59.90 and 53.26 [Willems G, Lambrechts P, Braem M, Celis J P, Vanherle G. A classification of dental composites according to their morphological and mechanical characteristics. Dental materials, 1992;8:310-9, incorporated herein by reference in its entirety]. VHNs of nHA/E-glass based composites disclosed herein are even higher than those of the commercially available composites. Therefore, these experimental composites are expected to withstand masticatory forces in clinical applications.

SEM results revealed that all experimental composites contained E-glass fibers with an average size of 150-220 p.m and globular shaped nHA particles with an average size of 35-150 nm. The nano-particle sized hydroxyapatite is biologically important as it is chemically similar to the minerals present in enamel, dentin and bones. nHA also improves the polishability and mechanical properties due to its high surface area to volume ratio and structural uniformity [Zhu X, Eibl O, Berthold C, Scheideler L, Geis-Gerstorfer J. Structural characterization of nanocrystalline hydroxyapatite and adhesion of pre-osteoblast cells. Nanotechnology 2006;17:2711, incorporated herein by reference in its entirety]. In the experimental composites, some globules of nHA were firmly attached to the glass fibers while some are loosely embedded in the organic matrix. A degree of impregnation of filler/fiber used in dental applications affects properties of composites. During the synthesis of composites, the fibrous fillers were placed longitudinally as well as transversely. However, more fibers were oriented in a longitudinal direction. The orientation of E-glass fibers present in the resin matrix is critical in determining the mechanical and physical properties of the resin composite [Fonseca R B, Paula M S d, Favarão I N, Kasuya A V B, Almeida L N d, Mendes G A M, et al. Reinforcement of dental methacrylate with glass fiber after heated silane application. BioMed research international 2014;2014, incorporated herein by reference in its entirety]. Glass fibers having a multidirectional orientation offer better properties as compared to those having a unidirectional or longitudinal orientation [Malchev P G, de Vos G, Picken S J, Gotsis A D. Mechanical and fracture properties of ternary PE/PA6/GF composites. Composites Science and Technology 2010;70:734-42; and Shah V. Handbook of plastics testing technology. 1998, each incorporated herein by reference in their entirety]. In all control and experimental composites, the reinforcing agents were equally distributed. It was reported that resin matrix reinforced with randomly distributed short E-glass fibers possessed better mechanical properties [Garoushi S, Vallittu P K, Lassila L V. Use of short fiber-reinforced composite with semi-interpenetrating polymer network matrix in fixed partial dentures. Journal of dentistry 2007;35:403-8, incorporated herein by reference in its entirety]. Evenly distributed fibers within the resin improve wear resistance of the restoration. Fibers centered at one place would enhance the strength and quality of the restoration.

In order to predict the clinical outcome of a particular resin based composite, the strength of its adhesive joint should be evaluated by an appropriate bond strength test [Thomsen K B, Peutzfeldt A. Resin composites: strength of the bond to dentin versus mechanical properties. Clin Oral Investig 2007;11:45-9, incorporated herein by reference in its entirety]. In the current disclosure, push out test was used to measure the bond strength of the experimental composites to dentin. An advantage of push out test is its capability to evaluate the bond strength of a composite placed in a high C factor cavity. The cavity design in a push out test may subject the composite restoration to a large polymerization shrinkage stress [Chen W P, Chen Y Y, Huang S H, Lin C P. Limitations of push-out test in bond strength measurement. Journal of endodontics 2013;39:283-7, incorporated herein by reference in its entirety].

The experimental composites disclosed herein differed in terms of their concentrations by weight of the fillers incorporated in the polymer matrix. The experimental composites were each loaded with 60 wt %, 50 wt %, and 40 wt % of the fibrous filler. The fibrous filler used were nHA coated short randomly oriented E-glass fibers. The commercial composite was filled by zirconia and silica nanoparticles. E-glass fibers are made of aluminum borosilicate and may be an appropriate reinforcement agent for a methacrylate polymer matrix due to their high mechanical properties, low moisture absorption, chemical inertness, and high thermal stability (32). These short randomly oriented glass fibers may provide an isotropic reinforcement from many directions rather than a single direction, which is preferable when the direction of the highest stress is unknown. They may have better flexural strength and fracture toughness as compared to those of unidirectional and bidirectional fibers [Khan A S, Azam M T, Khan M, Mian S A, Rehman I U. An update on glass fiber dental restorative composites: A systematic review. Materials Science and Engineering: C 2015; 47:26-39, incorporated herein by reference in its entirety]. Preferably, short fibers in the current disclosure may be oriented randomly.

Nano-hydroxyapatite has found use in restorative dentistry because of its biocompatibility, bioactivity, radiopacity, and good hardness. There is a growing interest in applying nHA to dental composites for its ability to release calcium ions and potential benefit of remineralization. A variety of studies evaluating the physical and mechanical properties of hydroxyapatite based composites have been done. However, bond strength studies on these hydroxyapatite based composites are scarce. No commercial restorative material containing hydroxyapatite has been marketed yet.

The push out test results of the current disclosure indicated that the composite with a higher filler concentration would have a greater bond strength. The presence of filler particles provides stiffness to the resin matrix and thus increases the elastic modulus of the composite [Van Noort R, Noroozi S, Howard I, Cardew G. A critique of bond strength measurements. Journal of dentistry 1989;17:61-7, incorporated herein by reference in its entirety]. The amount of filler in the experimental composites was positively correlated with the respective dentin bond strength, with Exp-RBC60 having the greatest bond strength to dentin. A previous study also observed an increase in the concentration of nano-hydroxyapatite in the composite led to a significant increase ($p \leq 0.05$) in bond strength. Also, greater push out bond strength values were achieved when the samples were immersed in artificial saliva [Khan A, Wong F, McKay I, Whiley R, Rehman I. Structural, mechanical, and biocompatibility analyses of a novel dental restorative nanocomposite. Journal of Applied Polymer Science 2013;127:439-47, incorporated herein by reference in its entirety].

Most failures for dental composites are related to poor adhesive properties. There were no cohesive failures observed after storing all the samples in artificial saliva for 180 days, indicating no decrease in the mechanical strength. In a push out test, the test assembly is designed in a way that failure is forced to occur at the adhesive interface. The forces are directed parallel to the adhesive interface, hence majority of failures occurred were adhesive in nature [Frankenberger R, Kramer N, Oberschachtsiek H, Petschelt A. Dentin bond strength and marginal adaption after NaOCl pre-treatment. Operative dentistry 2000;25:40-5, incorporated herein by reference in its entirety]. Another reason for adhesive failures was related to the stress bearing ability of the experimental composites. Elastic modulus and flexural strength of a restorative increase as the filler content in the polymer matrix increases. Dentin has a flexural modulus of about 20 MPa. The weakest area is the adhesive interface where the point of stress concentration develops resulting in adhesive failure [Van Noort R, Noroozi S, Howard I, Cardew G. A critique of bond strength measurements. Journal of dentistry 1989;17:61-7, incorporated herein by reference in its entirety].

The amount of calcium and phosphorus ion precipitation at the interface increased with increasing amount of nano HA in the experimental composites, with Exp-RBC 60 having the greatest precipitation of calcium and phosphorus ion at the interface. Precipitation of calcium and phosphorus ion might be resulted from the presence of nano hydroxyapatite crystals as fillers in these composites. Compared to conventional materials, nanoparticles fillers provide superior physical properties partially because of their nanometer size, a large surface area, and capability of releasing high levels of ions at a low filler content [Melo M A, Guedes S F, Xu H H, Rodrigues L K. Nanotechnology-based restorative materials for dental caries management. Trends in biotechnology 2013;31:459-67, incorporated herein by reference in its entirety]. These ions can diffuse from the interior of the pre-saturated resin and create a high concentration of calcium and phosphorus ions at the surface, resulting in precipitation and deposition as apatite onto the dentin and strengthening the adhesive joint [Melo M A, Guedes S F, Xu H H, Rodrigues L K. Nanotechnology-based restorative materials for dental caries management. Trends in biotechnology 2013;31:459-67, incorporated herein by reference in its entirety]. Another reason for the calcium and phosphorus ion deposition at the interface may be related to dentinal proteins present in the decalcified matrix which have an affinity for $Ca^{2+}$ ions. Thus these proteins might serve as calcium accumulators and reservoirs for apatite crystallization, and play an important role in the deposition of calcified matrix at the adhesive interface, thereby strengthening the bonding to the tooth structure [Hoshi K, Ejiri S, Probst W, Seybold V, Kamino T, Yaguchi T, et al. Observation of human dentine by focused ion beam and energy-filtering transmission electron microscopy. Journal of microscopy 2001;201:44-9, incorporated herein by reference in its entirety].

The invention claimed is:

1. A method of preparing a fibrous filler comprising silanized glass fibers having an average diameter of 5-100 μm and an average length of 50-2,000 μm, bioactive particles comprising hydroxyapatite disposed on a surface of the silanized glass fibers, and a silane coating that coats at least a portion of a surface of the silanized glass fibers, bioactive particles, or both, wherein the silanized glass fibers are present in an amount of 15-65 wt% relative to a total weight of the fibrous filler,
the method comprising:
heating precursor glass fibers in an acidic solution to form acid activated glass fibers;
washing and drying the acid activated glass fibers to form surface activated glass fibers;
mixing the surface activated glass fibers with an aqueous solution comprising a Ca(II) salt and NH$_4$OH to form a first mixture;
mixing an aqueous solution of (NH$_4$)$_2$HPO$_4$ with the first mixture to form a second mixture;
microwave irradiating the second mixture to form a third mixture;
aging the third mixture to produce a crude fibrous filler; and
treating the crude fibrous filler with a silanization agent thereby forming the fibrous filler.

2. The method of claim 1, wherein the precursor glass fibers are E-glass fibers.

3. The method of claim 1, wherein the bioactive particles have an average particle size of 5-500 nm.

4. The method of claim 1, wherein the bioactive particles further comprise fluorapatite, amorphous calcium phosphate, or both.

5. The method of claim 1, further comprising:
forming a resin composite comprising a polymerizable monomer; a polymerization initiator system; and the fibrous filler by mixing the fibrous filler with a liquid mixture comprising the polymerizable monomer and the polymerization initiator system.

6. The method of claim 5, wherein the fibrous filler is present in the resin composite in an amount ranging from 25 wt% to 75 wt% relative to a total weight of the resin composite.

7. The method of claim 5, wherein the polymerizable monomer is at least one selected from the group consisting of a methacrylate monomer, an acrylate monomer, an epoxy monomer, and a vinyl monomer.

8. The method of claim 7, wherein the polymerizable monomer is a methacrylate monomer.

9. The method of claim 8, wherein the methacrylate monomer is at least one selected from the group consisting of bisphenol A-glycidyl methacrylate (bis-GMA), urethane dimethacrylate (UDMA), and triethylene glycol dimethacrylate (TEGDMA).

10. The method of claim 9, wherein the methacrylate monomer is a mixture of bisphenol A-glycidyl methacrylate (bis-GMA), urethane dimethacrylate (UDMA), and triethylene glycol dimethacrylate (TEGDMA).

11. The method of claim 10, wherein a weight ratio of bisphenol A-glycidyl methacrylate (bis-GMA) to urethane dimethacrylate (UDMA) ranges from 2:1 to 1:2, and a weight ratio of bisphenol A-glycidyl methacrylate (bis-GMA) to triethylene glycol dimethacrylate (TEGDMA) ranges from 3:1 to 1:1.

12. The method of claim 5, wherein the polymerization initiator system comprises a free radical initiator.

13. The method of claim 5, wherein the polymerization initiator system consists of camphorquinone and ethyl 4-(dimethylamino)benzoate.

14. The method of claim 1, wherein the Ca(II) salt is calcium(II) nitrate.

15. The method of claim 1, wherein the first mixture and the second mixture each have a pH of 9-11.

16. The method of claim 1, wherein microwave irradiating the second mixture is performed at 500-2000 W for 1-30 minutes.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Mur OP-F Primer

<400> SEQUENCE: 1
tctgatgaga ccgtcactgc                                              20

<210> SEQ ID NO 2
<211> LENGTH: 20
<212> TYPE: DNA
<213> ORGANISM: Artificial Sequence
<220> FEATURE:
<223> OTHER INFORMATION: Mur OP-R Primer

<400> SEQUENCE: 2
aggtcctcat ctgtggcatc                                              20

<210> SEQ ID NO 3
<211> LENGTH: 20
<212> TYPE: DNA
<213> ORGANISM: Artificial Sequence
<220> FEATURE:
<223> OTHER INFORMATION: Mur-Col-1a1-F Primer

<400> SEQUENCE: 3
gagaggtgaa caaggtcccg                                              20

<210> SEQ ID NO 4
<211> LENGTH: 20
<212> TYPE: DNA
<213> ORGANISM: Artificial Sequence
<220> FEATURE:
<223> OTHER INFORMATION: Mur-Col-1a1-R Primer

<400> SEQUENCE: 4
```

```
aaacctctct cgcctcttgc                                              20

<210> SEQ ID NO 5
<211> LENGTH: 20
<212> TYPE: DNA
<213> ORGANISM: Artificial Sequence
<220> FEATURE:
<223> OTHER INFORMATION: Mur GAPDH-F Primer

<400> SEQUENCE: 5
aaggtcatcc cagagctgaa                                              20

<210> SEQ ID NO 6
<211> LENGTH: 20
<212> TYPE: DNA
<213> ORGANISM: Artificial Sequence
<220> FEATURE:
<223> OTHER INFORMATION: Mur GAPDH-R Primer

<400> SEQUENCE: 6
ctgcttcacc accttcttga                                              20
```